United States Patent
Arnaud

(10) Patent No.: US 10,850,117 B2
(45) Date of Patent: Dec. 1, 2020

(54) SONOLUMINESCENT BIOPHYSICAL OSCILLATION TECHNIQUES (SBOT) AND METHOD TO IMPROVE HEALTH

(71) Applicant: Chantal Arnaud, Brooklyn, NY (US)

(72) Inventor: Chantal Arnaud, Brooklyn, NY (US)

(*) Notice: Subject to any disclaimer, the term of this patent is extended or adjusted under 35 U.S.C. 154(b) by 0 days.

(21) Appl. No.: 16/849,852

(22) Filed: Apr. 15, 2020

(65) Prior Publication Data
US 2020/0330791 A1 Oct. 22, 2020

Related U.S. Application Data

(60) Provisional application No. 63/009,912, filed on Apr. 14, 2020, provisional application No. 62/834,690, filed on Apr. 16, 2019.

(51) Int. Cl.
*A61N 5/06* (2006.01)
*A61N 7/00* (2006.01)
(Continued)

(52) U.S. Cl.
CPC ......... *A61N 5/0622* (2013.01); *A61N 5/0616* (2013.01); *A61N 7/00* (2013.01);
(Continued)

(58) Field of Classification Search
CPC .............. A61N 5/0622; A61N 7/00; A61N 2007/0039; A61N 2005/0663; A61M 21/00–02
See application file for complete search history.

(56) References Cited

U.S. PATENT DOCUMENTS 5,441,495 A 8/1995 Liboff et al.
6,122,550 A 9/2000 Kozhemiakin et al.
(Continued)

FOREIGN PATENT DOCUMENTS

GB 28978 7/1913
WO 2009/076250 A1 6/2009
(Continued)

OTHER PUBLICATIONS

Milne, R., Sorgnard, R. Quantum Theory Underpins Electromagnetic Therapies for Pain Management. Practical Pain Management. vol. 13. Issue 1. http://www.practicalpainmanagement.com.
(Continued)

*Primary Examiner* — Thaddeus B Cox
(74) *Attorney, Agent, or Firm* — ePatentManager; Guerry L. Grune

(57) ABSTRACT

One or more devices, systems, and methods are described which together provide sonoluminescence biophysical oscillation technique(s) (SBOT(s)) that improve debilitated states of health for individuals comprising; biophysical oscillations that initiate, sustain, and/or control one or more sound emitting devices including speakers capable of providing harmonic and subharmonic sound and including music and/or individual musical notes that provide sound tracsons and one or more light emission devices including projectors that provide light wave emission traclums which are capable of imparting color changes, wherein tracsons and traclums provide auditory and visual stimuli that result in energy changes that create acoustic and tracson/traclum excitations. The tracson/traclum excitations are applied in an external manner to one or more bodies of humans and in some cases could be applied to animals.

26 Claims, 72 Drawing Sheets

(51) Int. Cl.
 *A61M 21/02* (2006.01)
 *A61M 21/00* (2006.01)
(52) U.S. Cl.
 CPC ..... *A61M 21/02* (2013.01); *A61M 2021/0027* (2013.01); *A61M 2021/0044* (2013.01); *A61N 2005/0626* (2013.01); *A61N 2005/0663* (2013.01); *A61N 2007/0039* (2013.01)

(56) References Cited

U.S. PATENT DOCUMENTS

| | | |
|---|---|---|
| 7,081,083 B2 | 7/2006 | Ardizzone |
| 7,418,108 B2 | 8/2008 | Oser |
| 7,500,956 B1 | 3/2009 | Wilk |
| 7,981,064 B2 | 7/2011 | Oser et al. |
| 8,057,408 B2 | 11/2011 | Cain et al. |
| 8,617,089 B2 | 12/2013 | Oser et al. |
| 8,761,417 B2 | 7/2014 | Oser et al. |
| 2007/0141179 A1 | 6/2007 | Wiegand et al. |
| 2014/0107525 A1 | 4/2014 | Tass |
| 2018/0328917 A1 | 11/2018 | Ilan |

FOREIGN PATENT DOCUMENTS

| | | |
|---|---|---|
| WO | 2014006596 A1 | 1/2014 |
| WO | 2018160749 A1 | 9/2018 |

OTHER PUBLICATIONS

Crum, L. Resource Paper: Sonoluminescence. The Journal of the Acoustical Society of America 138, 2181 (2015); doi: 10.1121/1.4929687.

Brenner, M., Higenfeldt, S., Lohse, D. Single-bubble sonoluminescence. Reviews of Modern Physics, vol. 74, No. 2. Apr. 2002.

Margulis, M. Sonoluminescence. Physics—Uspekhi 43 (3) p. 259-282. 2000.

Yasui, K. , Tuziuti, T., Sivakumar, M. & Iida, Y. Sonoluminescence, Applied Spectroscopy Reviews, 39:3, 399-436, 2004. DOI: 10.1081/ASR-200030202.

Putterman, S. and Weninger, K. Sonoluminescence: How Bubbles Turn Sound into Light. Annu. Rev. Fluid Mech. 2000.32:445-476.

Jung, D., International Search Report. Korean Intellectual Property Office. ISA/KIPO. Form PCT/ISA/210. Box A-C, dated Aug. 26, 2020, Daejeon, Rebublic of Korea.

Jung, D., Written Opinion of the International Searching Authority. Korean Intellectual Property Office. ISA/KIPO. Form PCT/IS/237, p. 3-6, dated Aug. 26, 2020, Daejeon, Rebublic of Korea.

MICROSOUND/MICROLIGHT PARTICLES /TRACSONS/TRACLUMS DURING SBOTS

ADVANCED TECHNOLOGY/SOUND-LIGHT DEVICES/DIGITAL INDUSTRY/HANDICAP TOOLS

DETAILED SBOT PROCESS DESCRIBING MICROSSOUND/MICROLIGHT PARTICLES/ TRACSONS/TRACLUMS

NO WAVE CYCLES: NO-GENERATING CYCLE (LEFT) AND INACTIVE CYCLE (RIGHT)

1

NO-GENERATING CYCLE: ACTIVE PHASE FORMATION OF HEME-NO COMPLEX

AT TRACSON STIMULUS INDUCTION FROM BACKWARD MASKING SOUND EFFECT IN MUSIC NO BINDS ON PORPHYRINS OF HEME UNIT GROUPS AT CITRATE PHASE INDUCTION IN TCA CYCLE THROUGH ITS INTERACTION WITH CITRULINE, ONE OF THE KEY INTERMEDIATES IN THE BIOSYNTHESIS OF ARGINE

2

PHASE SHIFT OF NO FORMATION INITIAL PHASE IN CITRATE PHASE OF TCA CYCLE TO ITS DECAY IN ELECTRON TRANSPORT CHAIN IN CYTOCHROMES

3

INACTIVE CYCLE INDUCTION DURING THE DECAY OF A HEME NO COMPLEX WHERE AT INDUCTION OF TRACTION STIMULUS FROM FORWARD MASKING SOUND EFFECT NOS MOLECULE INTERACTS WITH CYTOCHROMES PORPHYRINS AND THEIR FERRIC SULFUR CENTERS WHICH DEPEND FROM OXIDATIVE PHOSPHORYLATION OR FROM SUBSTRATE LEVEL PHOSPHORYLATION INDUCTION

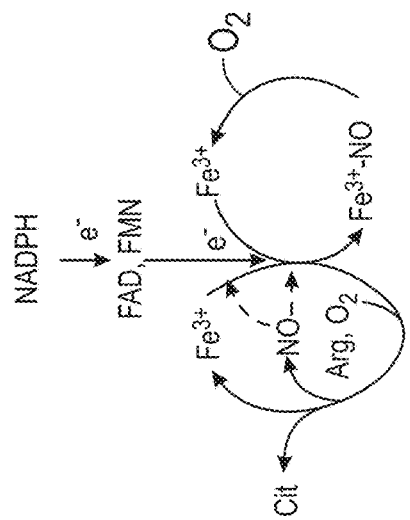

FIG. 6C

COLOR SHIFT DURING SBOTS

APPLIED SONOLUMINESCENT BIO-OSCILLATIONS

| 1 | 2 | 3 | 4 | 5 | 6 | 7 |
|---|---|---|---|---|---|---|
| TRACSON STIMULI INDUCTION COMING FROM THEIR INTEGRATION IN SELECTED MUSIC COMPOSITION FOR THE PARTICIPANT IN APPLIED SONOLUMINESCENT APPLICATION. | AIR MOLECULES MIXED WITH SOUND MOLECULES TARGETING EXTERNAL EAR MIETUS AND NOSTRIL EVERY 5-10 MS FROM SELECTED MUSIC WAVE INDUCTION FOR THE PARTICIPANT IN APPLIED SONOLUMINESCENT BIOOSCILLATIONS. | MIDDLE EAR SOUND VIBRATION STIMULI LEAD TO A PRESSURE AT THE COCHLEA ABOUT 22 TIMES THE PRESSURE THAT THE SOUND WAVE HAS AT THE EAR DRUM, SO WITH A STRENGTH OF 1.3 POWER UNIT COMING FROM THE OSSICLES IN THE TYMPANIC CAVITY WHICH MECHANICALLY CONVERT THE SOUND | INNER EAR SOUND VIBRATION STIMULI IN RELATIONSHIP WITH NO HEME COMPLEX 2 STEPS CYCLE INDUCTION AT EACH FORWARD TRACSON STIMULUS INDUCTION WHICH REPRESENTS FORWARD MASKING SOUND EFFECT INDUCTION 1.2 S BEFORE INDUCTION OF SOUND TRACK FROM SELECTED MUSIC | SINGLE AND MULTIPLE OUTER HAIR CELLS SOUND RESONANCE STIMULI IN RELATIONSHIP WITH SONOLUMINESCENT BIOOSCILLATIONS INDUCTION AND THE RELEASE OF SOUND ENERGY WHICH SPREADS TO THE PARTICIPANT'S WHOLE BODY PARTS. | COCHLEAR NUCLEI STIMULI WHEN SOUND FREQUENCY SIGNALS REACH SUPRA-OLIVARY NUCLEI →STAPIS PLATE AND FACIAL NERVE REFLEX CONTROL | COLLICULUS NUCLEI STIMULI →GENICULATE BODY STIMULI →PRIMARY AUDITORY REFLEX |

FIG. 9A

| A | B | C | D | E | F | G | H |
|---|---|---|---|---|---|---|---|
| | | VIBRATIONS IN THE EARDRUM INTO AMPLIFIED PRESSURE WAVES IN THE FLUID OF THE COCHLEA (OR INNER EAR) WITH A LEVER ARM FACTOR OF 1.3, AND SO THEN THERE IS THE COMBINED TRANSFER SOUND VIBRATION SIGNALS PROCESSING IN MIDDLE EAR FOLLOW BY THE INDUCTION OF SOUND FREQUENCY RESPONSE IN INNER EAR HAIR CELLS | COMPOSITION FOR THE LISTENER FOLLOW BY BACKWARD TRACSON INDUCTION WHICH REPRESENTS BACKWARD MASKING SOUND EFFECT INDUCTION AND THIS PROCESS OCCURS IN A REPETITIVE ALTERNATED FASHION INTERMITTENTLY AT 5-10 S INTERVALS DURING APPLIED SONOLUMINESCENT BIOOSCILLATIONS. | | | |

FIG. 9B

APPLIED SONOLUMINESCENT BIO-OSCILLATIONS

| 1 | 2 | 3 | 4 | 5 |
|---|---|---|---|---|
| MIDDLE EAR CAVITY SOUND HARMONICS INDUCTION FOLLOW BY SUBHARMONIC SOUND ACCUMULATION INDUCTION ON 6 TRASCON SITES FROM EACH TRASCON STIMULUS INDUCTION FROM 2 SUBSEQUENT 4 SOUND ROTATIONS INDUCTION SEPARATED BY 1 MINUTE INTERVAL OF REGULAR MUSIC DIFFUSION OVER APPROXIMATELY 10 MINUTES FOR EACH PHASE OF SOUND ROTATIONS (1 TO 5 WITH PHASE 6 REPRESENTING | MIDDLE EAR HARMONIC SOUNDS VIBRATE IN MIDDLE EAR CAVITY. | INNER EAR SOUND (COCHLEA) SOUND TRANSDUCTION AT THE ONSET OF DISCHARGE RELEASE OF HARMONIC VIBRATION (VIBRATION FROM THE MIDDLE EAR CAVITY) >DISCHARGE OF ACETYLCHOLINE OVER 5 S->WHICH FOLLOWS STAPES PLATE ACTIVATION AND THEN THERE IS A DISCHARGE OF NITRIC OXIDE OVER 2 SECONDS IN COCHLEAR SYSTEM | ACTIVATION OF SOUND SUBHARMONICS ACCUMULATION SITES CALLED TRACSON SITES SEQUENTIALLY AT EACH TRACSON INDUCTION FIRST ON 5 SUBSEQUENT SPECIFIC SITES IN PARA-VERTEBRAL SYMPATHETIC GANGLION CHAIN FOLLOW THEN BY 1 STEADY PREDOMINANT CORTICAL TRACSON SITE IN SPECIFIC LOBE IN OCCIPITAL CORTEX VERSUS FRONTAL CORTEX BY REPETITIVE ALTERNATION | RELEASE OF SOUND ENERGY FROM SOUND CAVITATION BUBBLES COMING FROM SENSITIVE MICRO SOUND MOLECULES INDUCTION FIRST IN CEREBROSPINAL FLUID IN CENTRAL CANAL FOLLOW BY 4 TH. VENTRICLE, THEN BY THIRD VENTRICLE, THEN BY 2 LATERAL VENTRICLES OVER 30 S-> FOLLOW BY TRANSITION OF SOUND VIBRATION SPREADING TO |

FIG. 10A

APPLIED SONOLUMINESCENT BIO-OSCILLATIONS

| 1 | 2 | 3 | 4 | 5 | 6 |
|---|---|---|---|---|---|
| LATENT HARMONIC SOUND TRACKS INDUCTION FROM 6 TRACSON SITES INDUCTION WHICH GENERATE SONOLUMINESCENT BIO-OSCILLATIONS OVER APPROXIMATELY 10 MINUTES BY THE USE OF TRACSON STIMULI (FORWARD-BACKWARD SOUND MASKING EFFECTS WHICH ARE INTEGRATED IN THE SELECTED MUSIC COMPOSITION) FROM 2 MINUTES OF SUBSEQUENT | 8 ALTERNATED LATENT HARMONIC SOUND PATHWAYS INDUCTION WHICH GENERATE SONOLUMINESCENT BIO-OSCILLATIONS OVER ~10 MINUTES. >LATENT SOUND HARMONIC (SUBHARMONICS) -LUMINESCENT CHROMOPHORES OSCILLATORY ALTERNATOR INDUCTION IN RELATIONSHIP WITH PREDOMINANT BRAINWAVE MODE INDUCTION | INDUCTION OF SENSITIVE VERY LOW SOUND FREQUENCY GROUPS IN MULTIPLE 3 UNITS OUTER HAIR CELLS IN BASILAR MEMBRANE IN ASSOCIATION WITH MICRO SOUND MOLECULE BUBBLES INDUCTION IN CEREBROSPINAL FLUID SEQUENTIALLY IN CENTRAL CANAL, IV VENTRICLE, III VENTRICLES, 2 LATERAL VENTRICLES | SIGNALS STIMULI COMING FROM SENSITIVE VERY LOW FREQUENCY SOUNDS CAPTURED BY BRAIN RHYTHM AND THERE IS INDUCTION OF STEADY PREDOMINANT BRAIN RHYTHM IN SPECIFIC LOBE BY REPETITIVE ALTERNATION INTERMITTENTLY OVER ~ 10 MINUTES IN ASSOCIATION WITH SENSITIVE LIGHT MOLECULES INDUCTION WHICH REPRESENT CHROMOPHORES | THERE IS INDUCTION OF SIGNALS STIMULI COMING FROM SENSITIVE VERY LOW FREQUENCY SOUNDS IN ASSOCIATION WITH PHOTON ENERGY RELEASE FROM HUMAN EUKARYOTIC CELLS AND THIS LEADS TO INDUCTION OF PREDOMINANT STEADY BRAINWAVE MODE IN OCCIPITAL VERSUS FRONTAL AND THE INDUCTION OF SOUND VIBRATION SIGNALS STIMULI ORIGINATING FROM FEET EXTREMITIES | DELIVERY ACTION TO CENTRAL PROCESS AND PERIPHERY OF SOUND VIBRATION SIGNALS STIMULI IN ASSOCIATION WITH 1.5 S TRANSITION THROUGH TOES FOLLOWS BY 1.5 S TRANSITION THROUGH FINGERS IN RELATIONSHIP WITH TRANSITION OF 1.5 S FOR EACH SPECIFIC SITE IN CEREBRAL CORTEX TO TRANSFER FROM ONE PREDOMINANT OCCIPITAL SITE OVER 1.5 S VERSUS |

FIG. 11A

| A | B | C | D | E | F | G |
|---|---|---|---|---|---|---|
| 4 SOUND ROTATIONS INDUCTION BY MINUTE SEPARATED BY 1 MINUTE INTERVAL OF REGULAR MUSIC COMPOSITION OVER ~10 MINUTES AND EACH SOUND ROTATION OCCURS EVERY 15 S WHICH LEADS TO SOUND PROPAGATION BY QUARTER TURN AROUND LISTENER'S HEAD. | IN SPECIFIC LOBE IN CEREBRAL CORTEX IN OCCIPITAL CORTEX VERSUS FRONTAL CORTEX ALTERNATELY OVER ~10 MINUTES. | FOLLOW BY SOUND ENERGY RELEASE FROM DIFFERENT SEGMENTS LEVEL OF SPINAL CORD IN ASSOCIATION WITH 6 TRACSON SITES ACTIVATION WHICH ALLOW THE SPREADING OF SOUND VIBRATIONS ALL OVER THE PARTICIPANT'S BODY PARTS ->TRANSITIONAL INDUCTION OF 3 PREDOMINANT AFFECT MODES WITH OVER ~14 POTENTIAL PRIMARY + SECONDARY AFFECTIVE REACTIONS. | IN RETINA PLEXUS AND WHICH FOLLOW BY THE RELEASE OF PHOTON ENERGY FROM EUKARYOTIC CELLS IN HUMAN BODY TISSUES WHICH TRANSFER TO SONOLUMINESCENT BIO-OSCILLATIONS-> THOSE SIGNALS STIMULI COMING FROM SENSITIVE VERY LOW FREQUENCY SOUND CAPTURED BY BRAIN RHYTHM ALLOW SOUND VIBRATIONS TO SPREAD ALL OVER LISTENER'S BODY. | ORIGINATING FROM FEET EXTREMITIES LEADS TO THE INDUCTION OF THE BRAINWAVE MODE IN ONE SPECIFIC SITE IN CEREBRAL CORTEX. | FOLLOWS BY SOUND VIBRATION SIGNALS STIMULI COMING FROM THE EXTREMITIES OF HANDS WHICH LEADS TO THE TRANSITION OF THE BRAINWAVE MODE FROM ONE SPECIFIC SITE TO ANOTHER SPECIFIC SITE IN CEREBRAL CORTEX. | ONE OTHER PREDOMINANT FRONTAL SITE OVER 1.5 S BY REPETITIVE ALTERNATION INTERMITTENTLY. |

FIG. 11B

| TRACSONS-CHROMOPHORES STIMULI IN E1>E2>E3 PHASE TRANSITIONS DURING 5 PHASES OF SONOLUMINESCENT BIO-OSCILLATIONS WITH EITHER USE OF HEADPHONE OR SPEAKERS |
|---|

① BI-AURICULAR CRESCENDO — THE INTEGRATION OF TRACSONS-CHOMOPHORES STIMULI IN SELECTED MUSIC/LIGHT-COLOR-OPTIONAL IMAGE IN E1>E2>E3 LEADS TO 4 SOUND-LIGHT ROTATIONS / MINUTE OVER 2 MINUTES AROUND THE HUMAN HEAD SEPARATED BY 1 MINUTE OF REGULAR MUSIC DIFFUSION/REGULAR LIGHT-COLOR-OPTIONAL IMAGE PROJECTION WITHOUT THE INTEGRATION OF TRACSONS/CHROMOPHORES STIMULI BY INTERMITTENT REPETITIVE ALTERNATION FOR EACH OF THE 5 PHASES OF SONOLUMINESCENT BIO-OSCILLATIONS WHICH LASTS OVER~ 10 MINUTES

② GETTING USED TO THE BI-AURICULAR TRACSONS/ CHROMOPHORES SIGNALING

③ 1 SOUND-LIGHT ROTATION /MINUTE

④ 2 SOUND-LIGHT ROTATIONS /MINUTE (A)

(B) 4 SOUND-LIGHT ROTATIONS / MINUTE OVER 2 MINUTES — REGULAR MUSIC DIFFUSION /MINUTE (C) 4 SOUND-LIGHT ROTATIONS/MINUTE DURING 2 MINUTES (D) (AM) USE OF SPEAKERS FOR MUSIC DIFFUSION IN THE AUDIOVISUAL ROOM
*(RM) USE OF HEAD PHONE FOR MUSIC DIFFUSION IN RIGHT/LEFT HUMAN EAR DURING 4 SOUND-LIGHT ROTATIONS/MINUTE DURING 2 MINUTES BY REPETITIVE ALTERNATION WITH 1 MINUTE OF REGULAR MUSIC DIFFUSION THROUGH BOTH HUMAN EARS OVER ~10 MINUTES FOR EACH PHASE OF SONOLUMINESCENT BIO-OSCILLATIONS IN THE AUDIOVISUAL ROOM

FIG. 13A

SPACE TIME EVENTS CHANGES OF BIOPHYSICAL SONOLUMINESCENT OSCILLATIONS IN S1>S2>S3 DURING SBOTS ON HUMAN BODY

CHARGE/DISCHARGE OF TRACSONS/TRACLUMS DURING SBOTS

SOUND/LIGHT ANALGESIA CALLED TRACSONS/TRACLUMS ANALGESIA

FIG. 23B

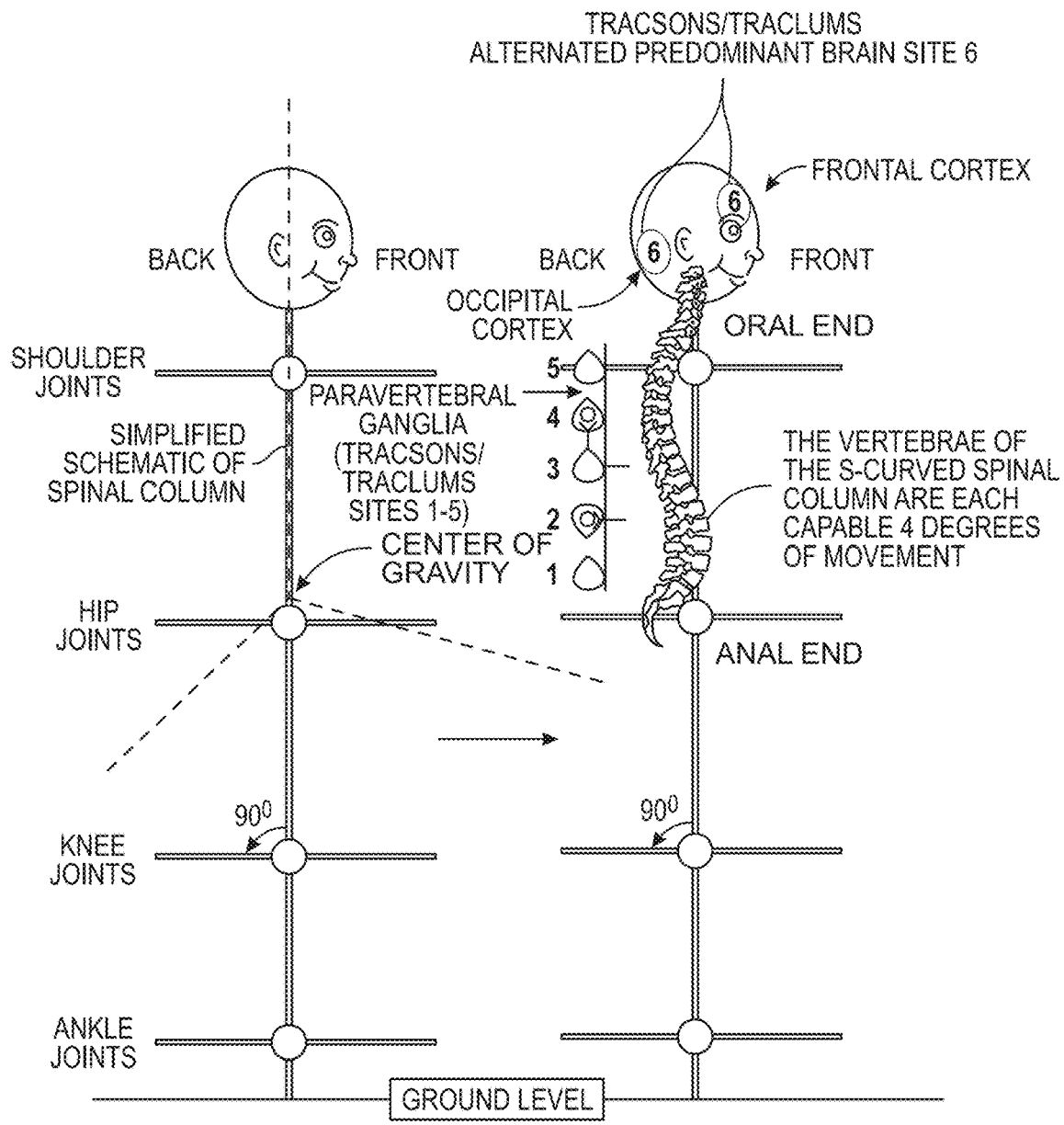

| A | EQUILIBRIUM POSITION OF THE HUMAN BODY FROM HEAD TO TOE (SIDE VIEW) |
| B | SUCCESSIVE SONOLUMEN WAVE FORMS SW1 › SW2 › SW3 |

SW1(1)* SW1 BACKWARD /FORWARD RING PULSING EXPANSIONS TOWARD ORAL/ANAL END OF THE HUMAN BODY SIMULTANEOUSLY IN LONGITUDINAL/TRANSVERSAL PLAN (3D)

SW2(2)* SW2 INTERCROSSING WAVE FORMS IN BETWEEN S1-S3 FORMING FROM OPEN RING-ENDS TO CLOSE-CONICAL TUBULAR ENDS

SW3(3)* SW3 BACKWARD/FORWARD TUBULAR PULSING ELONGATIONS TOWARD ORAL/ANAL END OF THE HUMAN BODY SIMULTANEOUSLY IN LONGITUDINAL/ HORIZONTAL PLAN (3D)

FIG. 24A

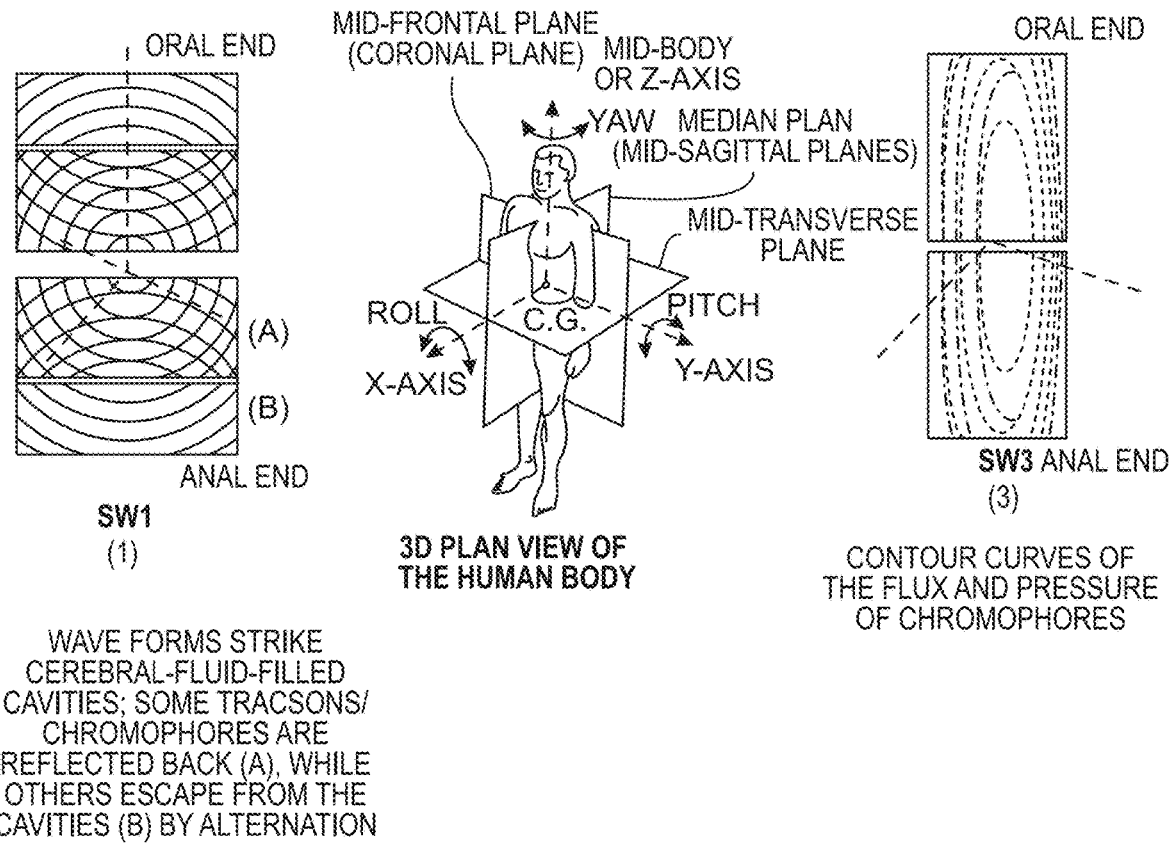
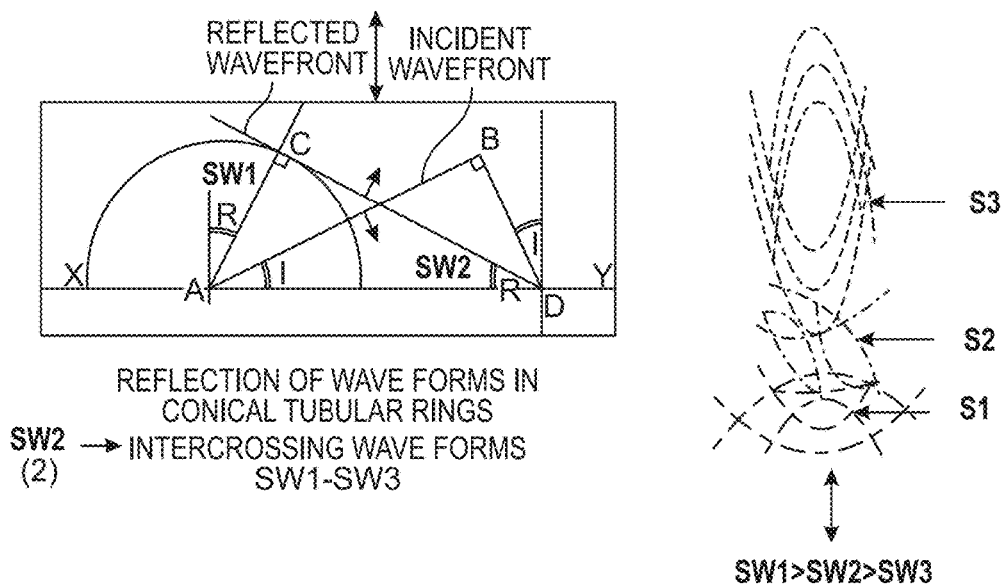
FIG. 24B

EQUILIBRIUM POSITION OF THE HUMAN BODY FROM HEAD TO TOE (SIDE VIEW)

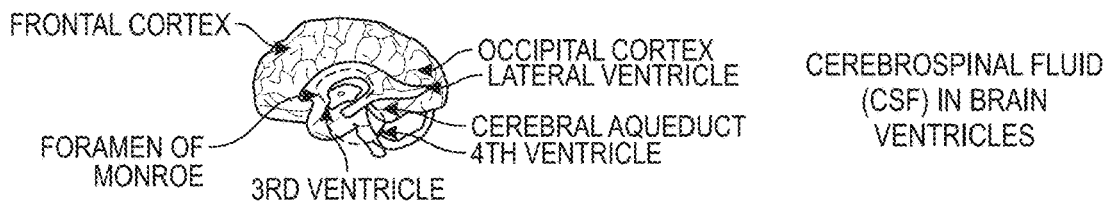
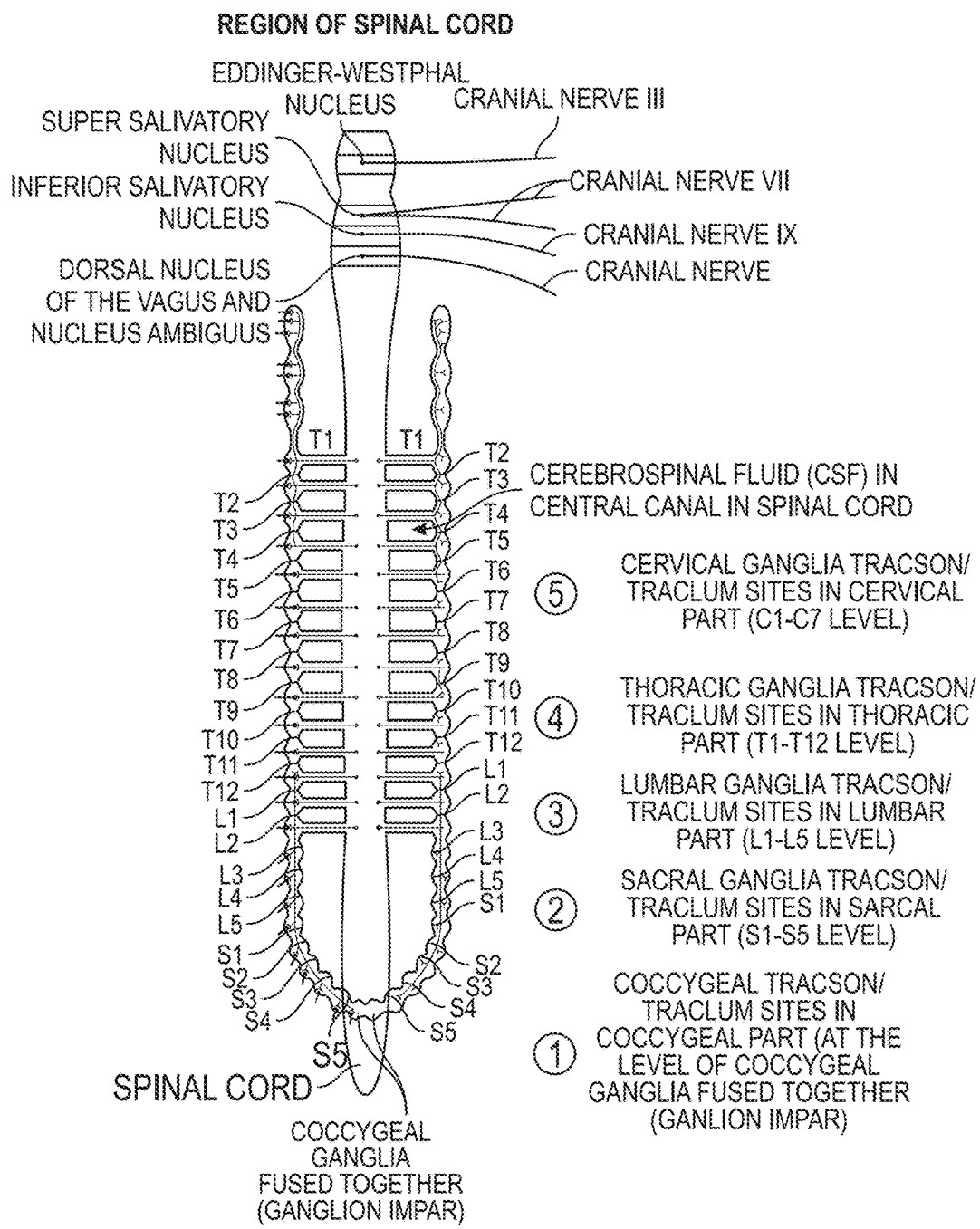
FIG. 27

```
┌─────────────────────────────────────────────────────────────────────┐
│ CHANGES IN PREDOMINANT BRAIN WAVE MODE IN OCCIPITAL/FRONTAL CORTEX-REVERSE │
│ DURING SBOTS/IN NEURAL PLASTICITY BY REGULATING ENDORPHINS BINDING TO │
│ U-OPIOID RECEPTORS SUCH AS BETA ENDORPHINS THAT ACT AS A MORPHINE PUMP │
│ LIKE EFFECTS TO MODULATE PAIN SENSATIONS                            │
└─────────────────────────────────────────────────────────────────────┘
                                    │
┌─────────────────────────────────────────────────────────────────────┐
│ CHANGES IN ENDOGENOUS CANNABINOID SYSTEM (ECS) MODULATOR OF SYNAPTIC │
│ NEUROTRANSMITTER RELEASE IN RESPONSE TO STRESS                      │
└─────────────────────────────────────────────────────────────────────┘
                                    │
┌─────────────────────────────────────────────────────────────────────┐
│ CHANGES IN                                                          │
│ 1. ENDOGENOUS CANNABINOID LIGANDS (LIPID MEDIATORS AS ENDOGENOUS LIPID-BASED │
│ RETROGRADE NEUROTRANSMITTERS THAT BIND TO AND ACTIVATE CANNABINOID  │
│ RECEPTORS/LIGANDS DEGRADATION PATHWAYS                              │
│ 2. CANNABINOID RECEPTORS (CANNABINOID PROTEINS RECEPTORS)           │
│ 3. ENZYMES FOR SYNTHESIS/DEGRADATION OF ENDOGENOUS CANNABINOIDS     │
└─────────────────────────────────────────────────────────────────────┘
                                    │
┌─────────────────────────────────────────────────────────────────────┐
│ CHANGES IN                                                          │
│ 1. AEA ENDOGENEOUS LIGAND ANANDMIDE/FABPs FATTY ACID BINDING PROTEINS/FAAH │
│ DEGRADATION LIGAND/CB1R CANNABINOID RECEPTOR IN MOST HUMAN BRAIN/PNS/NAPE │
│ OLEOYLETHANOLAMINE OEA TWO CANNABINOID TRANSPORTER ENZYMES          │
│ 2. 2-AG ENDOGENEOUS LIGAND 2-ARACHIDONOYLOLYCEROL/MAGL DEGRADATION  │
│ LIGAND/CB2R CANNABINOID RECEPTOR EXPRESSED IN IMMUNE CELL, MICROGLIA │
│ 3. NON CB1F/NON CB2R CANNABINOID RECEPTORS EXPRESSED IN ENDOTHELIAL CELLS, │
│ MICROGLIA IN CNS                                                    │
│ 4. CHANGES IN GPR18/GPR55/GPR119 ORPHAN RECEPTORS                   │
│ 5. PALMITOYLETHONALAMIDE PEA FATTY AMINE RELATED TO AEA, BINDING TO │
│ RECEPTORS : PPAR-αR PEROXISOME PROLIFERATOR-ACTIVATED RECEPTORS AS GENETIC │
│ SENSOR FOR FATS/LIGAND-ACTIVATED TRANSCRIPTION FACTORS/REGULATING GENES │
│ INVOLVED IN CARBOHYDRATES/LIPOPROTEIN METABOLISM/TRPV1R/GPR55R      │
│ 6. OLEOYLETHANOLAMIDE OEA MONOUNSATURATED ANALOGUE OF AEA BINDING TO │
│ RECEPTORS PPAR-αr/GPR119R                                           │
│ 7. ADDITIONAL ENDOGENOUS CANNABINOID SUBSTANCE SUCH AS              │
│ N-ARACHIDONYLDOPAMINE NADA, VIRODHAMINE, NOLADINE ETHER             │
│ 8. HEAT SHOCK PROTEINS HSPS SUCH AS HSP70 BINDING TO FATTY ACID BINDING │
│ PROTEIN FABPR RECEPTORS/HSP90 BINDING TO CB2R INTERACTIONS BY INTERMITTENT │
│ ALTERNATIONS CYCLES WITH CHANGES IN SHSPS (ALPHA BETA CRYSTALLIN) IN │
│ RESPONSE TO CHANGES IN HUMAN ADAPTATION TO LIGHT/DARKNESS/CANGES BY │
│ INTERMITTENT ALTERNATIONS OF PREDOMINANT PROTON H+ (HIGHER ALERTNESS) │
│ /VASOPRESSIN (LOWER ALERTNESS) CHANNEL CYCLES ON BRAIN TISSUES WITH SOME │
│ OTHERS SUCH AS AQ4/TRPV1 DURING VARIOUS RELAXATIO9N STATES OF SBOTS FIVE │
│ PHASES/CHANGES IN HSP60/HSF1 HEAT SHOCK FACTOR 1 PRIMARY MEDIATOR OF │
│ TRANSCRIPTIONAL RESPONSES TO PROTEOTOXIC STRESS WITH IMPORTANT ROLES IN │
│ NON STRESS REGULATION SUCH AS DEVELOPMENT AND METABOLISM LEAD TO CHANGES │
│ BY INTERMITTENT ALTERNATIONS IN CYCLES(MT/IF INTERMEDIARY FILAMENTS)/ │
│ (MICROFILAMENTS MF/IF) DURING SBOTS SEQUENCING CHANGES IN S1>S2>S3I WHICH │
│ LEAD TO CHANGES IN DEGENERATION/REGENERATION OF ALL HUMAN BODY TISSUES │
│ INCLUDING CNS/PNS DURING SBOTS                                      │
└─────────────────────────────────────────────────────────────────────┘
```

CHANGES IN ENDOGENEOUS CANNABINOID SYSTEM DURING SBOTS LEAD TO
REGENERATION OF HUMAN BODY TISSUES INCLUDING CNS/PNS

FIG. 28

THERE ARE CHANGES IN BONE MARROW (BLOOD FORMING SYSTEM)/BLOOD AND THE SYSTEM THAT FORMS IT, KNOWN AS THE HEMATOPOIETIC SYSTEM, CONSISTING OF MANY CELL TYPES WITH SPECIALIZED FUNCTIONS SUCH AS RED BLOOD CELLS (ERYTHROCYTES) CARRYING OXYGEN FROM TISSUES, PLATELETS (DERIVED FROM MEGAKARYOCYTES), HELPING PREVENT BLEEDING. GRANULOCYTES (NEUTROPHILS, BASOPHILS AND EOSINOPHILS) AND MACROPHAGES (COLLECTIVELY KNOWN AS MYELOID CELLS) HELPING WITH LOW IMMUNITY, B-LYMPHOCYTES, T-LYMPHOCYTES, WHICH CAN DIRECTLY KILL OR ISOLATE BY CELLS RECOGNIZED AS FOREIGN TO THE BODY, INCLUDING MANY DEGENERATIVE CELLS. FROM HEMATOPOIETIC STEM CELLS AND THEIR CAPACITIES FOR SELF-RENEWAL OR DIFFERENTIATION, AND FROM EARLY PROGENITOR CELLS AND THEIR CAPACITIES FOR PROLIFERATION AND MULTI LINEAGE DIFFERENTIATION, AND THEY ARE INVOLVED IN TISSUES/BONE REMODELING/REMOVAL OF DEAD CELLS.

AT PREDOMINANT CYCLES CHANNELS OF TRPV1 ON HUMAN BRAIN TISSUES UNDER STRESSED CELLS IN ASSOCIATION WITH CHANGES IN MICRO SOUND PARTICLES MOVING SEQUENTIALLY IN SPECIFIC CSF FILLED CAVITIES/MICROLIGHT PARTICLES ON HB PORPHYRINS/BNDF /COLD SHOCK PROTEIN PREVENTING SYNONUCLEIN ALPHA INCLUSION BODIES/FAT INTAKE METABOLISM/ORIGIN REPLICATION DNA IN HUMAN EUKARYOTIC CELLS IN ASSOCIATION WITH CHANGES IN BONE MARROW MATRIX/HEMATOPOIETIC SYSTEM AT HF-1-ALPHA (HYPOXIA TRANSCRIPTOR FACTOR) WHICH REGULATES OSTEOBLASTS- MEDIATED BONE RESORPTION ROLE OF ANGIOPOIETIN LIKE-4 INVOLVED WITH CHANGES IN BONE REPAIR/REGENARATION FOLLOW BY AT PREDOMINANT AQ4 CHANNEL CYCLE ON HUMAN BRAIN TISSUES AND CHANGES IN CA++ HOMEOSTASIS BY KIDNEYS/CHANGES IN MICRO SOUND PARTICLES ON PORPHYRINS RED BLOOD CELLS /MICROLIGHT PARTICLES ON HYDROPHOBIC PATCHES ON RED BLOOD CELLS MEMBRANES IN RELATIONSHIP TO COMPLEX 1 ACTIVATION IN HUMAN EUKARYOTIC CELLS UNDER STRESS/CHANGES IN ORIGIN TRANSCRIPTION DNA/LONG NON CODING RNAS/MRNA EXPRESSION IN RESPONSE TO CHANGES IN OSTEOGENIC DIFFERENTIATION OF HUMAN BONE MARROW MESENCHYMAL STEM CELL INVOLVED IN THE OSTEOGENIC DIFFERENTIATION OF BONE MARROW AND ADIPOSE-DERIVED MESENCHYMAL STEM CELLS IN RESPONSE TO CHANGES IN ADIPOCYTES MARROW TRPV1R UNDER STRESS INVOLVED WITH BONE REGENERATION AND REPAIR AND THEIR ARE CHANGES IN KEY SIGNALS OF HEMATOPOIETIC STEM CELL (HSC) ABILITY TO SELF-RENEW AND CHANGES IN SIGNALING IN ANGIOPOIETIN 1 IN OSTEOBLASTS INVOLVED IN BONE FORMATION COMPONENT IN ASSOCIATION WITH CHANGES IN ENVIRONMENT OF HSCS SELF RENEWAL TO TIE-2 RECEPTORS ON HSCS WHICH REGULATE STEM CELL QUIESCENCE (THE LACK OF CELL DIVISION) LINKED TO PHENOMENON OF TISSUE-DERIVATIVE ALTERNATE REGENERATIVE SIGNALS REFERRED TO AS QUOT;TRANSDIFFERENTIATION QUOT (CHANGEABLE HSCS PLASTICITY) AND CHANGES FIBROBLAST GROWTH FACTOR 2 (FGF2) TRANSFORMING PLATELET-DERIVED GROWTH FACTOR IN RESPONSE TO TRANSFORMING GROWTH FACTOR-BETA (TGF BETA) SUCH AS TGF BETA WITHIN HYPOXIA CONDITION AND CHANGES IN Ig G4 AND CHANGES IN DISK CELL WHICH ACTIVE EXTRACELLULAR MATRIX HOMEOSTASIS BY SEVERAL CYTOKINES AND VASCULAR ENDOTHELIAL GROWTH FACTOR (VGEF) ACTING IN AN AUTOCRINE AND PARACRINE FASHION, WITHIN INTERVERTEBRAL DISC (IVD) WITH LIMITED REGENERATIVE POTENTIAL AND DISC DEGENERATION (LOWER BACK/NECK) IN ASSOCIATION WITH CHANGES IN BLOOD FLOW (BLOOD CIRCULATION) NEARBY L4 AND NEARBY C4 IN RESPONSE TO CHANGES IN TRANSITIONS OF MICRO SOUND PARTICLES IN TRANSITION III VENTRICLES/2 LATERAL VENTRICLES AT TRPV1 R /HF-1 ALPHA UNDER STRESSED CELLS AND CHANGES IN TRANSFORMING GROWTH FACTOR INCLUDING TGF BETA 1 (GROWTH AND DIFFERENTIAL FACTOR) AND CHANGES IN HSPS SELF-RENEWAL INCLUDING INTESTINAL HEMATOPOIETIC STEM CELLS AT PREDOMINANT AQ4 AND SO CHANGES IN CEREBRAL BLOOD FLOW AND METABOLISM AT AQ4 CHANNEL ON HUMAN BRAIN TISSUES. NOW ANGIOPOIETIN -LIKE 4 IN RESPONSE TO CHANGES IN ADIPOSE DERIVED HIF-1 ALPHA AND PPAR GAMMA INDUCED GENE AND Gi9 ORPHAN RECEPTOR? AT TRPV1 CHANNEL UNDER STRESS AS AN ENDOCRINE AND AUTOCRINE PARACRINE REGULATOR OF LIPID METABOLISM (INVOLVED IN ADIPOSITY, CARTILAGE DEGRADATION, ANGIOGENESIS, MUSCULOSKELETAL DEGENERATION, OSTEOLYTIC MUSCULOSKELETAL DEGENERATION) AND SO BONE REMODELING BY INTERMITTENT ALTERNATION WITH ANGIOPOIETIN-1 RECEPTOR (VASCULAR ENDOTHELIAL GROWTH FACTOR (VEGF), BASIC FIBROBLAST GROWTH FACTOR ANG-1 AT TIE 2 RECEPTORS ON HSCS WHICH DISTINGUISHES MULTIPLE DIFFERENTIATE CAPABILITY WITHIN HYPOXIC CONDITION

SBOT & THE HEMATOPOETIC SYSTEM

FIG. 29A

NOW VEGF (HYPOXIA-INDUCED VASCULAR ENDOTHELIAL GROWTH FACTOR) INDUCES ENDOTHELIAL CELL PROLIFERATION AND ANGIOGENESIS AND THERE ARE ANG-1 AT TIE 2 RECEPTORS ON HSCS WHICH DISTINGUISHES MULTIPLE DIFFERENTIATE CAPABILITY WITHIN HYPOXIC CONDITION IN RESPONSE TO CHANGES IN VASCULARIZATION MEDIATED BY MESENCHYMAL STEM CELLS FROM BONE MARROW AND ADIPOSE TISSUE AT PREDOMINANT TRPV1 CHANNEL CYCLES BY CHANGES IN LEPTIN, LIPID BETA-OXIDATE ADIPOCYTE DIFFERENTIATION AND APOPTOSIS AT PREDOMINANT AQ 4 CHANNEL CYCLES, INVOLVED WITH CHANGES IN THE ADIPOSE MICROVASCULATURE MAINTAINED BY THE INTERPLAY BETWEEN POSITIVE AND NEGATIVE SIGNALS MEDIATED BY FACTORS INCLUDING ANG-1 (+) INDUCING ANGIOPOIETIN 1 EXPRESSION AND ANG-2 (-) INDUCING ANGIOPOIETIN 2 EXPRESSION

AT CHANGES IN CA++ HOMEOSTASIS BY KIDNEYS AND CHANGES IN TYROSINE AND OREXINERGIC PATHWAYS IN RELATIONSHIP TO CHANGES IN PREDOMINANT BRAIN WAVE MODE IN SPECIFIC LOBE IN HUMAN CEREBRAL CORTEX DURING SBOTS AT PREDOMINANT AQ4 CHANNEL BY INTERMITTENT ALTERNATION WITH PREDOMINANT VASOPRESSIN CHANNEL CYCLES ON BRAIN TISSUES UNDER NON STRESSED CELLS. SO ANG-1-ANG-2 BIND TO RECEPTOR TIE 2 PRESENT IN HEMATOPOIETIC STEM/PRECURSOR CELLS AND THERE ARE ANG-1 RECEPTOR AGONIST, EXPRESSED IN MANY TISSUES AND ANG-2 RECEPTOR ANTAGONIST WHOSE EXPRESSION IS LIMITED TO SITES OF VASCULAR REMODELING (LEPTIN-INDUCED LOSS OF THE ADIPOSE VASCULATURE)

SBOT & VASCULAR REMODELING

FIG. 29B

SO VASCULAR ENDOTHELIAL CELL GROWTH FACTORS (VEGF) TARGET ENDOTHELIAL CELLS SPECIFIC GROWTH FACTOR ANGIOPOIETIN WHICH INVOLVES ENDOTHELIAL CELLS, HEMATOPOIETIC CELLS AND EMBRYONIC PRECURSORS REQUIRED FOR WOUND HEALING PREVENT VASCULAR LEAKAGE IN RETINA BY CHANGES IN ENDOTHELIAL CELL SURVIVAL WITH ANG-1, IN BLOOD FORMATION AND VASCULAR ENDOTHELIAL FUNCTION UNDER STRESS AND NON STRESS CELL, AND THOSE SPECIFIC GROWTH FACTOR ANGIOPOIETIN ARE EXPRESSED PREDOMINANTLY ON TIE 2 RECEPTORS OF HSCS AND SO ANGIOPOIETIN LIKE 4 TRANSMEMBRANE PROTEIN KINASES SERVES AS SIGNALING RECEPTORS FOR A VARIETY OF POLYPEPTIDES LIGANDS, ELICITING SUCH DIVERSE RESPONSE AS CELL SURVIVAL, PROLIFERATION AND DIFFERENTIATION FOR MANY CELL TISSUES AND TISSUES IN RELATIONSHIP TO RECEPTOR TYROSINE KINASE (RTKS) WHICH HAVE THE ABILITY TO INTERACT WITH DIFFERENT LIGANDS AND ALWAYS ACTIVATING VARIOUS CELLULAR RESPONSE (RTK TYROSINE KINASE WITH IMMUNOGLOBIN AND EPIDERMAL GROWTH FACTOR HOMOLOGY DOMAINS)

SO THERE ARE OSTEOBLAST-SPECIFIC ANG-1 EXPRESSION INVOLVED IN BONE MASS (ALPHA TYPE (COLLAGEN) INVOLVED WITH BONE FORMATION )

TIE 2 IN VASCULAR ENDOTHELIAL CELL (VEGF) SIGNALING FOR ANGIOGENESIS AND SO FORMATION OF NEW VASCULATURE BY EMBRYONIC PRECURSORS FROM DE NOVO FORMATION INCREASE OF BLOOD VESSELS/INCREASE OF ALKALINE-PHOSPHATASE ACTIVITY, A MARKER OF OSTEOBLAST ACTIVATION LINKED TO CA++ HOMEOSTASIS IN KIDNEYS AND MOST RECENT EXPOSURE TO THE HUMAN BODY TO SUNSHINE/UV LIGHT

AND THERE IS ANGIOPOIETIN -LIKE PROTEIN 3 /CYTOKINE IN ASSOCIATION WITH HUMAN HEMATOPOIETIC STEM CELL THAT ADHERE TO BONE MARROW OSTEOBLASTS.

CA++ IONS ENHANCE MINERALIZATION AS WELL AS ANG EXPRESSION IN OSTEOBLASTS AND CONNEXIN 43, MAJOR MARKER OF CELL-CELL INTERACTION, WHERE AS ANG-2 RELATED TO INTEGRIN BETA 1, MAJOR MARKER OF CELL-MATRIX INTERACTION LOCAL CONCENTRATION REGULATES CELL MORPHOLOGY THROUGH THE CELL-CELL OR CELL-MATRIX INTERACTIONS TO THE ALTERATION OF ANG-1 EXPRESSION IN OSTEOBLASTS TRIGGERED AT PREDOMINANT AQ4 ON HUMAN BRAIN TISSUES IN ASSOCIATION WITH CHANGES IN CA++ HOMEOSTASIS BY THE KIDNEYS AND CONCERNED BY THE OSTEOGENIC DIFFERENTIATION OR REPRODUCTION OF HSCS NICHE ENVIRONMENT.

SBOT & OSTEOGENIC PROCESSES

FIG. 30A

THE CHANGES IN THE MAJOR COMPONENT INVOLVED IN BONE FORMATION COMPONENT OF ENVIRONMENT SELF RENEWAL OF HSCS AND SO THE PHENOMENON OF TISSUE-DERIVATIVE REGENERATIVE SIGNALS ALTERNATE REFERRED AS QUOTE: TRANSDIFFERENTIATION, QUOTE IN STEM CELLS TRANSPLANTATION IN HUMAN/ANIMAL BODY FROM CHANGEABLE HSPS PLASTICITY AND SO CHANGES IN THE CYCLES OF HEMATOPOIETIC STEM CELLS (HSCS) SELF RENEWAL OR DIFFERENTIATION BY INTERMITTENT ALTERNATION WITH PROGENITORS CELLS(PROLIFERATION AND DIFFERENTIATION) AND SO THERE ARE CHANGES IN THE CYCLES OF HEMATOPOIETIC STEM CELLS (HSCS) SELF RENEWAL OR DIFFERENTIATION BY INTERMITTENT ALTERNATION WITH PROGENITORS CELLS (PROLIFERATION AND DIFFERENTIATION)) IN RELATIONSHIP TO CHANGES IN THE EXPRESSION OF TELOMERASE, THE DNA REGION AT THE END OF THE CHROMOSOME THAT PROTECTS THEM FROM ACCUMULATING DAMAGE DUE TO DNA REPLICATION IN ASSOCIATION WITH ORIGIN TRANSCRIPTION DNA CHANGES AT PREDOMINANT AQ 4 CHANNEL CYCLES ON HUMAN BRAIN TISSUES UNDER STRESSED CELLS IN ASSOCIATION WITH CHANGES IN SIGNALING IN ANGIOPOIETIN ON OSTEOBLASTS INVOLVED IN BONE FORMATION COMPONENT OF NICHE ENVIRONMENT OF HEMATOPOIETIC STEM CELLS (HSCS) SELF RENEWAL IN RELATIONSHIP TO TIE 2 RECEPTORS ON HSCS WHICH REGULATE STEM CELL QUIESCENCE IN RESPONSE TO CHANGES DURING SBOTS OF INTERACTIONS OF MICROTUBULES (MT) BY INTERMITTENT ALTERNATION WITH INTERMEDIARY FILAMENTS (IF) AT S1 AND SO CHANGES IN MICROTUBULES (MT) TREAD MILLING AND 2 MOTOR PROTEINS DYNEINS/KINESINS BY ALTERNATION WITH BACKWARD/ FORWARD CIRCULAR STRETCHING OF RUN KISS INTERMEDIARY FILAMENTS (IF) IN ASSOCIATION WITH CONIC PULSING HELICES CIRCULAR STRETCHING WITHIN BACKWARD/FORWARD MOVEMENT AT S1.

SBOT & OSTEOGENIC PROCESSES (CONTINUED)

FIG. 30B

SBOT & TISSUE/ORGAN REGENERATION

CHANGES IN CHANNELS CYCLES: TRPV1/PROTON (H+)/AQ 4/VASOPRESSIN ON HUMAN BRAIN TISSUES DURING SBOTS

SONOLUMINESCENT BIOPHYSICAL OSCILLATION TECHNIQUES (SBOT) AND METHOD TO IMPROVE HEALTH

PRIORITY

This application is a nonprovisional conversion of and claims priority under US 35 USC 119 from Provisional Application No. 63/009,912, entitled "Sonoluminescent Biophysical Oscillation Technique (SBOT) and Method to Improve Health" and filed Apr. 14, 2020.

This application is a nonprovisional conversion of and claims priority under US 35 USC 119 from Provisional Application No. 62/834,690, entitled "Sonoluminescent Bio-Oscillation Technique (SBOT) and Method to Improve Human Health" and filed Apr. 16, 2019.

The above mentioned applications are hereby incorporated by reference in their entirety.

BACKGROUND

Field of Invention

The present disclosure describes the use of sonoluminescence oscillations techniques (SBOTs) that together with associated equipment/instruments and associated techniques have been developed over the course of time to positively change often debilitating states of human health on an individual basis. More specifically, the use of the equipment, instruments, and associated techniques are tailored on an individual basis for participants that require considerable improvement of their mental and physical abilities. This includes the need for pain management, overcoming severe handicaps including lack of conventional motor skills, and in some cases correcting overall general malaise that has resulted in departure from health and emotional stability. Often these individuals are in such a poor state of health for which the treatment by conventional medicine and medical techniques results in limited or no success. Many of the individuals who are submitted to the application of sonoluminescent biophysical oscillation techniques (SBOTs) and associated methods are desperate for finding a solution for their debilitated states of health. These biophysical oscillations are created by the use of sonoluminescence and have been found to provide considerable health value to those in need of major improvement for various ailments, including those conditions associated with degenerative tissues.

The present disclosure describes and is instructive regarding how to accomplish the SBOT(s) for regeneration of any tissue in the human body and especially for those individuals who are weakened or exist in a fragile constitution/deficient genetic predisposition/degenerative condition or in any other state of health influenced by over-stressed conditions. These include but are not limited to atrophied tissues and post trauma factors. The SBO techniques have been found to relieve symptoms associated with major accidents or deep frustration, emotional and/or physical abuses as well as health problems or weak health conditions, traumatic experiences or other issues that cause stress responses within any of the more than 75 trillion human cells. The use of necessary instruments and devices required for SBOT is herewithin provided for multiple individuals with the same or similar conditions.

Discussion of the Art

Sonoluminescence is a phenomenon that occurs when a small gas bubble is acoustically suspended and periodically driven in a liquid solution at ultrasonic frequencies, resulting in bubble collapse, cavitation, and light emission. The thermal energy released from the bubble collapse is so great that it can cause weak light emission. The mechanism of the actual light emission remains uncertain, but some of the current theories (some of which are included here within) are categorized as either thermal or electrical processes, including electromagnetic radiation, Bremsstrahlung radiations, argon rectification and hot spots. Some researchers are beginning to favor thermal process explanations as temperature differences have consistently been observed with the use of different methods of spectral analysis techniques to determine the actual science involved.

The SBOT includes the use of a lattice or network that induces free wavelength forms by alternating intermittent applications that appear at each inducement of tracsons/traclums on 6 human body sites associated with the central nervous system structure that utilizes the human exposure to specific auditory and visual stimuli in the environment by implementing multiple devices. These devices and corresponding treatment represent the manifestation of responses to the sonoluminescence biophysical oscillations (SBOT) resulting from the use of alternating intermittent application of massless particle duality obtained from tracsons/traclums at a ground or base energy level state. These are then applied to the 6 sites in a three-dimensional mode to the participants.

BRIEF DESCRIPTION OF THE DRAWINGS

FIG. 6C is a schematic of the nitrous oxide (NO) generating wave cycle (left side of the diagram) and inactive cycle (right side of the diagram) associated with the sonoluminescent biophysical oscillations (SBOTs) state of health improvements.

FIG. 9A and FIG. 9B provide a vertical flow chart that describes the step-by-step process for using applied sonoluminescent biophysical oscillations with tracsons causing stimuli due to selected music compositions resulting in colliculus nuclei stimuli and primary auditory reflexes.

FIGS. 10A and 10B provide a vertical flow chart that describes the step-by-step process for using applied sonoluminescent biophysical oscillations with middle ear cavity sound harmonics and subharmonics by using rotations and intermittent applications that include movement around the individual's head to induce the necessary human health state improvements for individuals undergoing SBOT applications.

FIG. 11A and FIG. 11B provide a vertical flow chart that describes the step-by-step process for using applied sonoluminescent biophysical oscillations with latent harmonic sound tracks, also known as tracsons that provide sonoluminescent biophysical oscillations which extend around and above the individuals head in a 3D plane to induce the necessary changes for individuals undergoing SBOT.

FIG. 13A is a schematic that describes how and why the stimuli of tracsons and associated chromophores in E1>E2>E3 energy transitions during 5 phases of sonoluminescent biophysical oscillations using sound are provided.

FIGS. 23A and 23B provide sound/light analgesia, referred to as tracson/traclum analgesia.

FIG. 24A is a schematic that shows how tracsons/traclums activate different sites within various health states.

FIG. 24B is a schematic that show how the waves forms and the tracsons/traclums are used to provide the capabilities for SBOTs to induce an improvement in the overall health of the participant.

FIG. 27 is a further description of the information provided for FIG. 26 with the addition of the correspondent features of the human brain.

FIG. 28 provides changes in the endogenous cannabinoid system during SBOTs and how the technique leads to the regeneration of human body tissues including CNS/PNS.

FIGS. 29A and B describe SBOTs and the hematopoietic system and one result of vascular regeneration.

FIGS. 30A and 30B describe SBOT and resulting osteogenic abilities.

DETAILED DESCRIPTION

Figure 1:
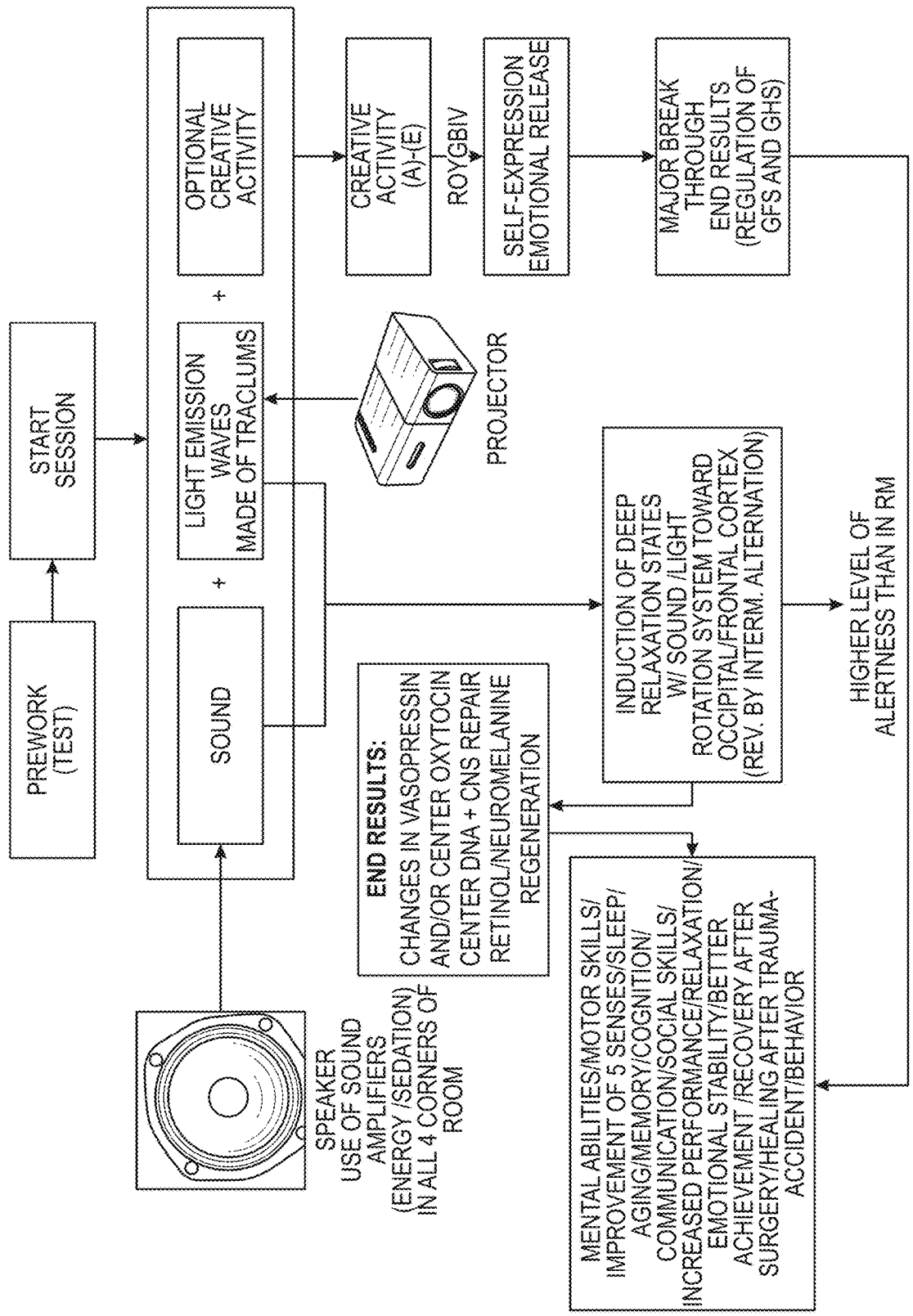
FIG. 1 is a schematic that provides a process flow chart for one or more SBOT applications (sessions) and the improvement of human body that initially has diminished capabilities in any tissue or organ function, including debilitating human conditions.

In the present disclosure, the Figures described above and provided herewithin are predominantly schematics and flow charts that detail methodology, equipment, or processes with specifics regarding the portions of SBOTs that are more fully described below. In some instances where the Figures are not self-explanatory, further information is provided below.

The Tracsons

The tracsons represent intermediate sounds that are integrated into the melody of selected musical compositions for the listener/participant in an audiovisual room over a period of 5 seconds. The tracsons are used in order to simplify the ability to target providing 4 to 10 notes per period of approximately 2 to 3 minute intervals over a length of time that is approximately 15 minutes.

The tracsons, when they are integrated in between 2 notes of music, allow for modification of the frequency of intervals by changing the intensity of the second sound resonance that the listener perceives during a period of latency between two notes of the music. The intensity of this second sound resonance is transformed based upon the first sound resonance which becomes partially perceived by the listener between 2 notes of the music and which is generated in a precise fashion by using fundamentals played in the musical composition according to 2 tones with pitch that is prolonged in relation to a fundamental note using a regular rhythm from selected musical compositions. This can also be provided to achieve prolonged periods of one to two (2) tones with pitch compared to a fundamental note linked to the octave in a variably pitched musical sequence. These second evolutive sound resonances (corresponding to pure sonorities) are dependent on the state of arousal or the state of relaxation of the participant that is induced by the music during the applications of the SBOTs (sonoluminescent biophysical oscillations). This is as a consequence to the first sound resonances partially perceived by the listener of the initial musical selection resulting from the sliding of notes (separated by micro-tones in relationship to the octave) between 2 fundamental notes separated by 1 or 2 tones (with pitch) as a function of the musical pitch.

This then leads to a new arrangement of sound resonance of sequential and/or linear notes. In fact, the musical effect of intermediary sound produced by the integration of tracsons in the musical composition comes from a group of notes related to a new arrangement of the sound resonance of notes that depends on whether each note has a certain degree of consonance with the preceding and/or following notes. This determination is made by the ability to discern proper respective pitch associated with the frequency of vibration for each of the tracsons.

As each note is either higher or lower in pitch than the other in the musical composition, the movement from one note to another usually involves either ascending or descending notes along the musical scale, and therefore the notes are provided in a new arrangement of sound resonances to provide for the proper use of the tracsons.

Types of Tracsons

The impact of the listener's sound resonance perception can be slowed down and then increased or accelerated to create a different effect on the participant. In this manner more emphatic integration of tracsons and the intensity of the ultimately produced tracsons associated with the melodic lines that can be achieved allows for changes in the interval frequency in between the notes and the tracsons. This will influence the manner in which a played note in between the 2 notes during integration of enhanced tracsons resonate starting from a fast prolongation in between 2 notes from the nearby side of the note to another note (or in reverse order), can be achieved. As a result, in addition, a heavy glide-like transition from applied energetic tracson types provide a gentle oscillation between the 2 notes. (This means that this mechanism leads to an activation increase that potentially target single unit hair cells in the basilar membrane of the cochlear system in inner ear). These tracsons generate high frequencies sound resonance stimuli on the basilar membrane and then there is a diminution of the accumulation of a threshold of tracsons which are captured on sonoluminescent biophysical oscillations. This leads to a decrease of the relaxation level and an augmentation and an increase in awareness of the participant.

When the listeners/participants have a deep-seated emotional instability for a long period of time, they will need tracsons captured very vastly and very rapidly on their sonoluminescent pathways from sedative tracsons integrated in music which allow new arrangements of associated emotions. This is especially necessary at the time release of unconscious elements by diminishing several emotional peaks and this will lead to resetting emotional balance.

When listeners goes through a temporary and acute emotional crisis, they overreact emotionally with intensity, and will need tracsons captured in lesser amounts and at a slower pace on the sonoluminescent pathways from energetic tracsons integrated in music which allows the listener through the increase of their awareness to readjust the intensity of the peak emotional feelings which disturbs many associated emotions and they will recover their emotional balance.

The amount of captured tracsons on sonoluminescent biophysical oscillations synchronize with the activation of the gut motility. In addition, the activation of the mesenteric plexus in the gut lining and the pre-vertebral sympathetic plexus activation in association with the fat absorption in the lacteal villi of the small intestine occurs. Also the induction of the lipid metabolism in the gut coupled with the induction of the listener's mode of affect (this means their subjective experienced feelings and their transition during the applications of the sonoluminescent biophysical oscillations) causes an adjustment of the flow and the elongation of the sonoluminescent biophysical oscillations in relation with the type of tracsons which are integrated in the selected music composition.

The Traclums

There is a need to understand how to apply sound wavelength frequencies with color wavelength frequencies on the human body to properly apply the SBOT(s). During the applications of the sonoluminescent biophysical oscillations on the human body, there is an induction of gravitational sonoluminescent biophysical oscillations wavelength forms within a space-time continuum that generates sound wavelength frequencies with color wavelength frequencies by intermittent repetitive alternated pulsing waves provided during the propagation of tracsons/traclums (as particles or waves) at the speed of light which are captured by the human body in response to the participant's exposure to an environment made of sound/music and light combined with colors and eventually images as provided in the audiovisual room. The techniques require that the exposures are provided with precision to produce powerful visual and auditory stimuli resonating on the body during the applications of the sonoluminescent biophysical oscillations. The resulting effects of those applications contribute to provide a reset of the neural plasticity, and improvement of basal physiological conditions in degenerative human bodies that require SBOT(s). This is obtained by inducing changes in the maintenance of the genome, the mature neurons, and the up-regulation of the pain pathways.

To apply the active SBOT methodology it is necessary to establish a protocol for the selection of light combined with colors in the audiovisual room. This is performed in association with sound-music and images through the projection of a slide show or a short movie on a screen in the audiovisual room.

The selection of music with the associated integrated tracsons and the effects on the participant follow exactly the same basic rules that is used for the music selection protocol described above. These are referred to as alternating sound rotations which, for example, include the choice of music and the integration of the tracsons (energetic or sedative type) that exist in between 2 notes in the melodic lines. In this case it is necessary to include complementary modifications for matching sound-images together in the slide show. As stated above, the typical SBOT has 5 phases including an additional phase 6 which is a "phase out" that is not always necessary. This is because the threshold level of the relaxation state which is reached during applied active SBOT may not induce the lowest level of the participant's alertness such as the type induced in sound analgesia/anesthesia during applied receptive methodology. It is known that similar wavelength frequencies of sound/light are captured by the participant's brain rhythm during the process of alternating sound rotation during applied receptive sonoluminescent biophysical oscillations. Therefore active methodologies differ slightly from the receptive methodologies because of an emphasis on the use of images and the projection of these images on the screen in the audiovisual room. However, at the same time both methodologies can be employed in a similar manner. The protocol of selectivity for sound-music combined with light and colors in the audiovisual room follow the same rules and similar wavelength frequencies of sound/light captured by the participant's brain rhythm. This generates an ability to provide e same dominant brainwave rhythm in the occipital cortex versus that of the frontal cortex and to reverse this process over approximately 10 minute durations applied for each of the 5 phases of sonoluminescent biophysical oscillations last over approximately 45-60 minutes per session.

It is also instructive to understand how image selection works.

The images for the short movie or the slide show, which are projected on the screen of the audiovisual room, are chosen from data that is stored in one or more photo libraries with all the categories of images having themes. These libraries are stored on hard drive and can be stored in the cloud for storage and retrieval as needed on demand. The content of the images selected for projection of the images in the slide show or short movie are abstract or real representations including background, textures and colors, symbols, numbers, letter(s), landscape, animals (birds, marine life, pets), people (communication, people, metaphors. faces), art and architectures (modern building, home, landmarks), nature (and their subcategory), travel, technology, objects, illustration, icons, footages and video clips in HD and in 4K, creative drawings or paintings, etc. For SBOT applications essentially any handpicked image from the participant's preferences of their image choices as well as from images that they self-produce at some point during the SBOT sessions (often by the use of an iPad or I-phone through digital technology in association with some simple basic computer program) are deemed a good starting point. Often the participants design their own graphics, drawing, paintings, illustrations, or in a more classical standard way of self-creativity by actual hand-drawing, painting, use of hand-made slides, modeling (by using clay or other safe materials) and/or music making in association with eventually some performance including a spontaneous free form of movement.

An additional set of options includes to provide, in the audiovisual room, shades and reflections of silhouettes from the participant projected onto the walls in the room, on the screen (Chinese numbers for instance). This provides another dimension to the audiovisual environmental space which provides for basic color projectors with various color filters that augments and enhances these effects. Once the images are created and selected they can be customized for the participant and eventually the possibility exists for some other additional participant's self-creativity to provide expression through free spontaneous form of movement, simple musical production through free form of rhythms or beats by using various musical instruments. It is also possible to include association with the use of intermediary objects such as chair, balloons, scarfs, etc.

It is necessary to understand that the tracsons interact with chromatophores (that are part of the traclums) on sonoluminescent biophysical oscillations pathways by alternating intermittent repetitions of the SBOT techniques over approximately 10 minutes during each phase of sonoluminescent biophysical oscillation applications.

Therefore there exists a capture and release of chromatophores on the sonoluminescent biophysical oscillations pathways by alternating intermittent repetitions with tracsons that depend upon the participant(s)'s sensitivity and response to color wavelength frequencies from exposure to the audiovisual environment in the audiovisual room. At the same time the participant(s) is a listener(s) and spectator in the audiovisual room and the environment is made of sound, music and light combined with colors in association with images coming from the projection of a slide show or short movie on the screen during the active SBOT application.

There is an integration of 5-10 traclums created (either sedative or energetic), in between 2 images during transitions of the slide show/short movie in the range of every 5-7 seconds over a time period of approximately 1-2 minutes. This includes alternating intermittent repetitions over approximately 10 minutes for each phase of sonoluminescent bio-oscillations so in the same way and at the same time this can be accomplished as was for the use of tracsons described above. In the case of the traclums, it is different than for the integration of the tracsons in between 2 notes in the melodic lines of the selected music compositions. Here the integration of the traclums in between 2 image transitions of the slide show or short movie which is projected on the audiovisual room screen, generates change in the induced transitions in between the 2 images. In this manner, various effects produced using these transitions in between 2 images by alternating intermittent repetitions over approximately 10 minutes allows for the participant to respond to the these traclum stimuli which are integrated in between the 2 images transitioning and the associated effects on the participant. Induction of chromatophores on sonoluminescent biophysical oscillations pathways at the 6 tracson accumulation sites accomplished by alternating intermittent repetitions that interact with tracsons at their intersections sites with the 6 tracson accumulations sites ultimately provide induced changes. This projection and selection of sound-music tracks-images/sequences for video clips in association with light and colors in the audiovisual room leads to creating an environment within the audiovisual room. Subsequently, the selected projected slide shows/short movie are projected onto the screen in the audiovisual room. This leads to changes in the participant's sensitivities with response to colored wavelengths.

By the use of various combinations of edited photos and video programs which complement each other and which allow the integration of traclums in between two images/2 video clips transitions in the selected slide show/short movie (which represent images/video motion graphics which interact with various music editing programs which also complement each other) that allows for the integration of tracsons in between 2 notes in selected music composition, there is the creation of a finalized music selection with tracsons in association with the images/video clips (or footage) selection producing traclums and associated effects. Therefore, the combination of tracsons and traclums are utilized for the applications of sonoluminescent biophysical oscillations in their active mode which provides for a more complete applied active SBOT methodology.

When the energetic traclums are integrated between two image transitions or two video loop transitions over the time line of editing the program, the images/video loops ripple rapidly and strongly (with high intensity) from either the upfront portion of the shown images/video loops sequences or the end portion to induce changes in between 2 image transitions of the slide show/short movie. Induction of changes in transition of intervals in between 2 image transitions of the slide show/short movie by integration of the energetic traclums provides a certain effect and affect to and on the participant. From the changes in the transition intervals in between 2 image transitions of the slide show/short movie there is also the possibility of introducing a still period of two images/video clips followed by a quick apparent change transition interval in between 2 image transitions that occurs over a latency period of time. The response in between the two images/video clips transitions occurs over approximately 10 minutes for each phase of an applied SBOT. Here there are sonoluminescent biophysical oscillations along with the integration of energetic traclums and the participant bonds quickly and strongly with the 2 images/2 video clips transitions. In other words, the participant usually responds with an intense emotional reaction and response at the sight of this transition. The transition of emotional expression fits the transition of subjective experiential feelings in the present mode (a mode associated with the existing time while the participant is undergoing SBOT) as the participant is directed toward a final mode (a mode that exists post SBOT application). Using this technique and in this manner, the participant can better process any recent negative effects regarding difficult or frustrating life events and deal better with any acute crisis regarding recent emotional states. This combined approach with dynamic tracsons/traclums and their either energetic and/or sedative nature allows the recipient/participant/patient to shift to better management of more recent emotional difficulties with a response that provides more emotional balance based upon the change of emotional states that are administered by use of the SBOT resulting in the need to recover emotional balance.

In the case where sedative chromatophores are required, they are integrated in between two images, transitions or two video loop transitions over the time required for editing the initial SBOT program selected for the individual participant. In this case, images/video loops ripple progressively from the upfront portion of the shown images/video loop sequences to the end portion of the sequences in order to induce changes in between 2 image transitions of the slide show/short movie. Induction of changes in transition intervals in between 2 image transitions of the slide show/short movie that occurs due to integration of energetic traclums provides a certain effect and affect to and on the participant. From the changes in the transition intervals in between 2 image transitions of the slide show/short movie there is also the possibility of introducing a still period of two images/video clips followed by a quick apparent transitional change of the interval in between 2 image transitions that occurs over a time period of latency that is a latency period.

Over approximately 10 minutes for each phase of SBOT where integration of sedative traclums and their effects and induced transition change intervals in between the 2 images as they transition (two images/2 video clips) allows for the participant to bond more slowly and more weakly with the 2 images/2 video clips transitions. In other words, the participant usually responds with a weaker emotional reaction and response at the sight of this transition. The transition of emotional expression fits the transition of subjective experiential feelings in the present mode as the participant is directed toward a final mode. Using this technique and in this manner, the participant can better process any long term (those from the not recent past including emotional drama that occurred in the DNA in utero development) up to present negative effects regarding difficult or frustrating life events and deal better with any acute crisis regarding past emotional states. This combined approach of tracsons/traclums allows the recipient/participant/patient to shift to a better management of repetitive accumulation of trauma or complex situations of life under a lot of stress due to further complications involving a long standing emotional instability.

Summarizing, it is necessary to first select the sequences used in the audio visual room regarding images, photos, and video clips deemed desirable for editing the initial program followed by selection of the background and texture for the photos and associated themes to customize the process for participant.

Next color selection is performed in order to adjust for color corresponding with temperature to fix the images and their layers. This helps to arrange the photos or the footage of videos so that they are easily viewed in the best light and so that it is possible to increase the effects of the color wavelength frequencies in the audiovisual environment. Through this process of editing color correction or colorimetry it is possible to modify the degree of fluorescence (tendency toward blue-greenish-purple color) or of phosphorescence (tendency toward red-orange-greenish-yellow color).

Current technology possesses photo and video editing programs with a color window to make color changes as desired and allows for simplifying the task of color correction. In addition to the color correction palette which is similar to a wheel of colors, there is second color correction which represents more advanced editing tools utilizing an RGB parade monitor, waveforms monitor and vector scope. This provides images or footage to perfect and amplify the effects of color wavelength frequencies for the participant in the audiovisual room during the active SBOT applications. The waveform monitor is a visual wave that represents the brightness in the image and video clip, and provides some engineering values so that it is possible to maximize the details in the images/video clips. In this manner one can fix visual details of the images/video clips. By implementing the use of the waveform monitor to adjust the brightness in the images/video clips, it is also possible to modify the visual stimuli caused by the audiovisual environment. This targets the participant's response to light/darkness adaptation and to the irradiance of light though opacity/transparency of the images. It is also possible to apply these techniques on selected images/video clips in between 2 images/2 video clip transitions providing integration of chromatophores during the development of the individualized program to suit the participant.

It is useful to note that the RGB parade is similar to the waveform monitor but utilizes different groups to select which hue of color is necessary and with what degree of intensity. This allows for selection regarding the manner in which fluorescence and the phosphorescence of the images/videos loops back to the chromatophore program under development. The RGB parade provides an equal amount of red, green, and blue, and yields equal amounts of colors in a video image. This allows one to determine how much of an amount of blue or yellow or green should be added to the images or videos.

The vector scope shows these colors and the center of the vector represents completely unsaturated (less intense) colors as well as white and black colors. As these editing tools have advanced due to digital technology, editing tools for secondary color correction for intensity and brightness has also advanced. For the purpose of applying SBOT it is important to know how to sonoluminescent biophysical oscillations modulate reflection of colors through phosphorescence/fluorescence as well as how the irradiance of light and its refractive light forms through opacity/transparency. This is especially important to control in between 2 traclums with images/2 video clip transitions where there the integration of traclums in the slide show/short movie is projected onto the screen of the audiovisual room as the participant witnesses these transitions.

In applying this technique it is possible to add or tint the images/video clips and their associated transitions where there are integration of traclums with more blue/green or more red/green associated with more transparency or opacity, as needed. This allows for inducing changes in the participant's sensitivity and associated responses to color wavelength frequencies in the audiovisual environment during the active applications of the sonoluminescent biophysical oscillations.

Introduction to SOBT's Phase Transitions

It is also important to note that the slide show/short movie projected in the audiovisual room must be capable of conveying a relaxing atmosphere and an environment of beauty with colors, In this case as the images/video clips eventually become pronounced (more red or more blue, more opaque or more transparent) it becomes more likely to perfect the phase 1-2 transitions of sonoluminescent biophysical oscillations applications. Also, as selection of the first abstract images/footage is performed it becomes less important to perform initial color correction. For the next phase transitions—phases 3-4 and phases 4-5, the level of the participant's alertness fluctuates and the participant experiences alternating repetitive intermittent introspection/retrospection through the induced changes linked to the transitions of subjective feelings experienced (during the present) which will influence progression toward the final mode within the audiovisual environment. Changes in the participant's response to colored wavelength frequencies in association with the luminescence effect from the refraction of light with those colors as well as associated color concentration gradients and the tones of those colors and color gradients all must be measured. The color tones of the color palette through fluorescence/phosphorescence and radiance provides color concentration gradients for shading. In addition, the brightness or darkness through opacity/transparency is provided in response to the participant's exposure to light and colors combined with the sound-music in the audiovisual environment.

Therefore it is necessary to adjust the creative part of the images/videos through the intensity of color vibrancy in order to decide which color should be selected and/or the details needed to amplify or eliminate in order to provide the most comprehensive and effective slide show/short movie.

It is also necessary to select motion effects through advanced editing tools which involve key framing that allow for the integration of chromatophores and the effects in between 2 images/2 video clip transitions. With animation of the key framing concepts it is possible to add track matte effects which provide the ability to isolate the visibility of a shape image. Adding key frames to the videos allows for creating image movements (animation) for the media elements of the audiovisual environment.

Key frames provide an ability to adjust a variety of parameters such as themes, common position, scale and rotation. It is necessary to employ two key frames when animating videos, images or even text or symbols. This allows for transformation and transitions providing the desired effects in between 2 images/2 video clips.

Once the additional editing tools are selected including for example transformational effects in association with key framing it is possible to adjust the nature of the traclums effects (sedative or energetic in nature) that are integrated in between 2 images/2 video clips transitions which facilitate the transition of the participant's subjective experiential feelings during the application of SBOT(s).

In one example it is possible to apply transitions that fade to black which symbolizes completion of the transition or that could also represents a passage of time.

Another possibility is to fade to white which represents the end of something different and also represent a passage of times, a continued action, or changes tone scene transitioning to another scene. This could include creation of a composition where the same images match or edit-out certain images or photos, etc. that allows for fading the scene in or out as determined during the course of the SBOT. In other instances it might be desirable to induce an abrupt transition (from a quiet serene setting to intense setting or vice versa). There are also times when it is desirable to provide an element of suspense to induce changes in the transitions of the experiential feelings experienced by the participant in the audiovisual room in association with the key framing effects.

Another set of advanced editing tools can be used to amplify the effects on the SBOT participant using a similar program selection throughout the sessions of active sonoluminescent biophysical oscillations to provide progressively transformable programs but at the same time preserve the basic visual and auditory stimuli in the audiovisual environment. The goal is to introduce new effects while maintaining the effects already provided for the original or earlier transitions.

In some cases it is possible to sort through layers of photos and images by providing several "loops" on video tracks (meaning the same sequential series being looped through multiple times) The images can include pre-compositions for masking some of the layers that provides a certain transparency or opacity to the images. Several techniques can be used to superimpose images by multi camera editing allowing for transfer of sequences of image/video montages on several tracks.

Next it is necessary to drop the zone where you apply the image masking in addition to providing specific signal effects for the motion slide show/video graphics. This is too performed in order to integrate these effects to provide the proper traclums effects. In this manner it is possible to keep the original transparency/opacity of original photos or video footage or even original creative drawings/paintings/art works provided by the participant. By selecting the participant's art work this may encourage a more positive outcome in the active applications of the SBOT.

Testing the receptivity of the participant is founded on similar criteria established for the test of music receptivity. In its simplest form the test allows for supplying the images/footages reflecting light and colors that are selected to replace the selection of music compositions in the music receptivity test.

The initial step for selection of images/photos/video clips and creating the slide show/short movie theme is the primarily concern. Images may represent abstract figures, geometric designs, symbols, numbers, letters, plain colors, landscapes, animals, nature, people and faces, festivals, holidays, etc. Therefore it is necessary to build sequences within sequential themes for each of the series of images/footages in order to provide the proper slide show/short movie to be projected on the screen in the audiovisual room. It is important to preserve the identical themes to induce steady entrainment of the participant's brain rhythm. Eventually slight modifications by using steady visual and auditory stimuli coming from the created audiovisual environment made of sound-music-light-colors and images can be made. These modifications are dependent on the earlier chosen selection of programs involving images/music and the resultant chromatophores/tracsons effects over the 5 phases of active sonoluminescent biophysical oscillations application that last approximately 45-60 minutes. These themes throughout the sessions at the rhythm of 1 to 3 times per week over at least 3 months and are provided to the participant within the respective medical and educational facilities capable of handling the SBOT.

During the applied active methodology of the SBOTs transition phase 1-2 image sequences represent abstract images that are normally not bright and/or shady images in order to avoid overstimulation from intermittent repetitive alternated traclums stimuli. If the participant(s) are especially vulnerable individuals with mental and physical handicaps then this portion of the therapy can be adjusted by changing the transparency and the opacity of the light in combination with colors in the audiovisual room.

The second set of images/footage sequencing at transition phases 2-3 contains another theme for the images/video clips selected for the slide show/short movie. These images/clips are projected on the screen in the audiovisual room and include images of nature such as flowers, landscapes, animals, under sea pictures, and allow for the mixing of colors combined with the surrounding light. The effects within the spatial audiovisual environment are selected and provided so that the participant(s) can respond to various color wavelength frequencies and also to their fluorescent/phosphorescent tendencies. This allows for the participants to progressively respond to the blended color with light-music-sound and so that the respective chromatophores/tracsons produced in the audiovisual environment are effective.

For the transition phases 4-5 of sonoluminescent biophysical oscillations SBOTs the applied active methodology requires more complex images/footages that amplify the participant(s) response and sensitivity to either dominant blue/tinted green color wavelength or dominant red/tinted green wavelength in response to intermittent alternating repetitions under non stress cells states of porphyrins pigment activation in red blood cells providing human sensitivity in response to predominant green color wavelength/fluorescent Flavin activation in cellular transport chain providing human sensitivity response to predominant blue color wavelength/phosphorescent porphyrins on cytochrome C in cellular transport chain in human body tissues providing human sensitivity response to predominant red color wavelength, all in relationship with complex interactions with retina, retinol, also known as Vitamin A, retinal, all Vitamin A-based light sensors for vision and most recent exposure of the listener to sunlight and UV light. This association with the changes in the induced channels on the participant(s) brain tissues provides induced changes in its neuroplasticity in response to induced changes in the SBOT generated dominant brain rhythm. This brain rhythm is created by the effective induction of tracsons/chromatophores on the participant(s) during the projection of the slide show/short movie on the screen in the audiovisual room. In phase transitions 4-5 there is considerable emphasis on the contrast of color tones with respect to various color palettes and shades.

Brightness or shadows in the light and the associated images/footages selection must convey powerful experiential subjective emotional feelings of beauty, peace, comfort/security to finalize the phase transition toward what the participant(s) require to recover balance and emotional stability.

In addition the music/images selection protocol is established in response to the test of music/color receptivity in association with the participant's anamnesis performed by the medical team/educational staff within their facilities. This allows for the evaluation of the participant(s)'s responses to light/colors/sound/music within their daily life and daily environment. The most effective tools for health improvement have been provided when it is also possible to understand most everything regarding the participant's life experiences. If the participant is incapacitated and cannot provide this, the input of the medical and educational assistance team and close family and/or friends who know the participant'(s) history and environment is a better substitute than not having any data.

As previously stated, it is possible for the participant to use manual technology of creating their own hand made slides, pictures by drawing, painting, modeling clay, by using ink, paints, pencils, color pen, charcoal pens, etc. It is also possible top allow for the use of digital technology through iPhone/iPad, etc. to design pictures or take photos or create short videos that can be integrated at some point into an original slide show/short movie during the sessions if the participant and the SBOT administrator determines this to be useful to improve the mental and/or physical states of handicapped persons.

In some cases 3-point lighting features of original photos and video clips that provide dimension to photos or footage such as key exposures, described as points of shadow can be provided by the participant. This may also include providing light with back edges that cause separation with the background and which help determine the quality of light in the picture. Often the response by the participant to light/darkness adaptation stimuli is enhanced in this way. The method by which light is "bounced" involves a picture or video that is created and provides a certain glow or highlight in the picture, drawing, painting, or illustration that creates "chemophores" of light. These can also be recreated in the audiovisual room when the participant becomes creative themselves and provide artwork that is eventually projected onto the screen. The highlight or shadow or a bit of glow adds vibrance to the self-created images or videos. In this manner the participant along with the SBOT facilitator fills the audiovisual environment with some of their creative work. This is often accomplished by designing it as a pre made portion of the intended overall program with additional selected sound-music/light combinations and colors and eventual images supplied by the participant.

The participant eventually uses this creative portion for the slide show including some preferred music selection to aid in advancing to a more advanced SBOT program using repetitive alternating intermittent sessions with the standard program previously selected. It is also possible that to add this in addition to the "standard" SBOT program allowing the participant to be able to express the transitions of their subjective feelings much better through their creative art work. Over time, this can also be exhibited by the participant in combination with spontaneous free form movements in response to viewing the slide show as well as the variations of the rhythm of the music. This may ultimately lead the participant to moving more freely and expressing their emotional states along with the beat of the music provided as intermittent alternating repetitions of the SBOT(s) along with the glow of the light and its colors.

Accessories such as color projectors with color filters are often added to the audiovisual room to enhance the effects of color wavelength frequencies that provide improved response of the participant. These are easily adjustable and send more light combined with colors into the environmental space of the audiovisual room. In this manner, the participant can experience the reflection of their silhouette on the screen and through their associated movements in combination with the projection of the slide show/short movie on the screen they essentially become part of the slide show in that they internally begin to "feel" the sound, art, music, etc. that has been either preprogrammed or dynamically programmed during the SBOT sessions. This goal, when accomplished, leads to increased self-identity and improve in communication skills.

There are also (intermediary with respect to the SBOTs) objects that may be introduced into the audiovisual room including chairs, pillows, canes, wheelchairs, etc. to allow the most handicapped participants with more severe limitations from past accidents to participate in sessions. Other objects including scarfs that reflect colors when accompanied by an induced form of movement for the participant can be very beneficial. In addition, canes and light balloons can be utilized during the sessions to further improve the communication of the participants. It has been determined that in these cases the participants more easily release their frustrations and/or fears so that they can better interact with other participants in the audiovisual room. It has been observed that the confines of the audiovisual rooms are also important for allowing freedom of movement for instance The SBOTs can be modified in order to provide for utilization in medical institutions such as clinics, rehabilitation centers, nursing homes, social institutions, health care facilities, etc. In fact, the SBOTs are useful and can employed where-ever and when-ever individuals struggle with physical/mental handicaps. The SBOTs have been proven to assist with changing and/or strengthening the central nervous system and the overall basal physiological conditions of tissues. The responses include improvements in genetic defects, trauma caused by accidents, etc., and have been used in institutions for children or adults with special needs, mental facilities including psychiatric hospitals, birthing centers, and other hospital facilities. The SBOTs have been found to contribute to better management of pain from sound analgesia and have been shown to alleviate and even eliminate pain which normally occurs during surgery allowing for the use of minimal chemical anesthetics and/or analgesics. The SBOTs have also been shown to accelerate recovery after surgery or from intense medical treatments. The response to SBOT has also resulted in better emotional as a complementary approach to conventional medical treatment.

Detailed Summary of SBOTs—What the Techniques are and how they Work

To avoid any confusion throughout the remainder of this disclosure and particularly in the Figures, SBOTs are based upon the use of bio-sonoluminescent oscillations that are synonymous with biophysical oscillations.

Figure 2:
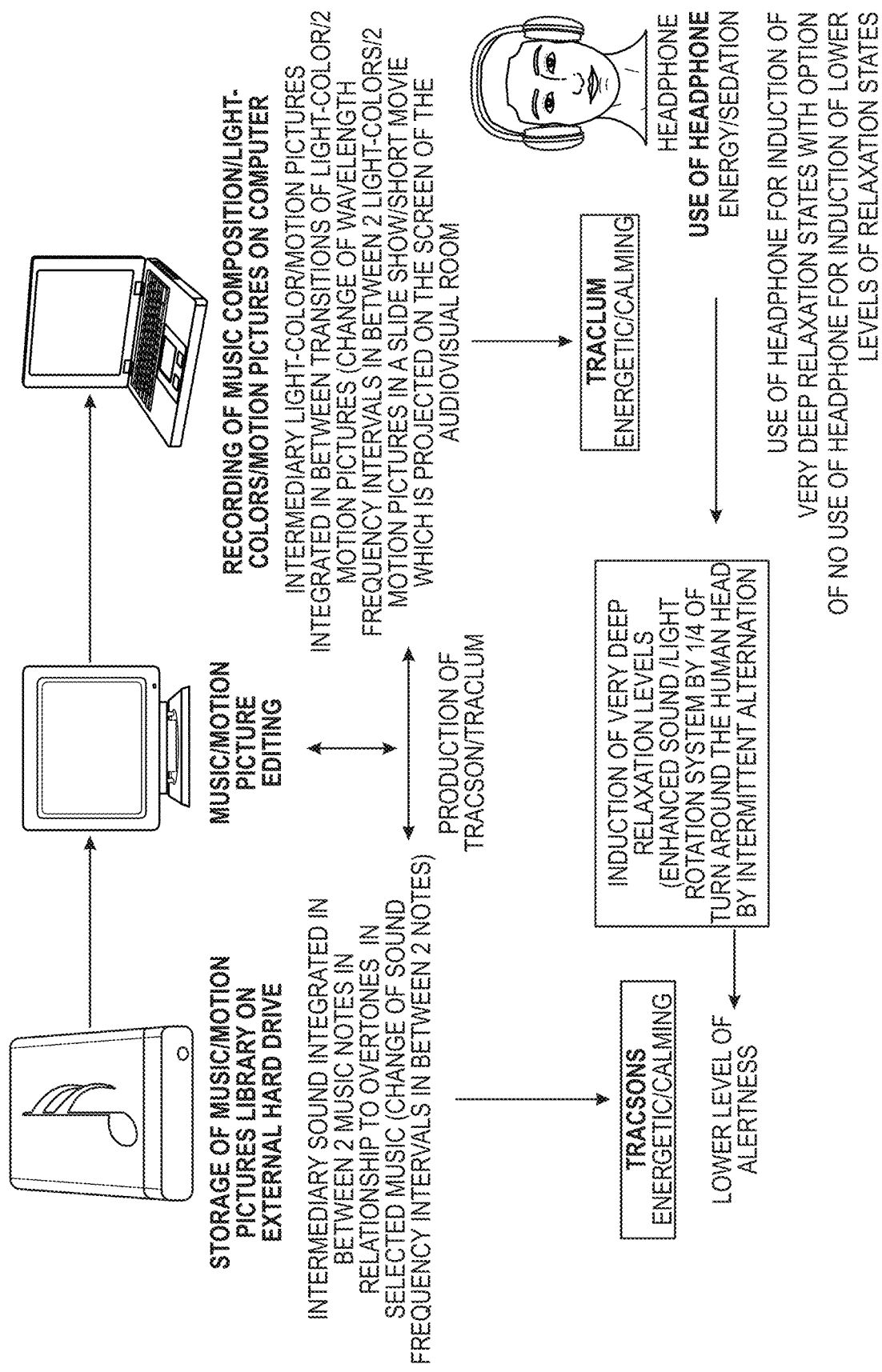
FIG. 2 is a schematic that provides a process flow for the induction of deep relaxation levels using enhanced sound and light rotations as well as intermittent SBOT applications for health improvement or to resolve health problems.
Figure 3:
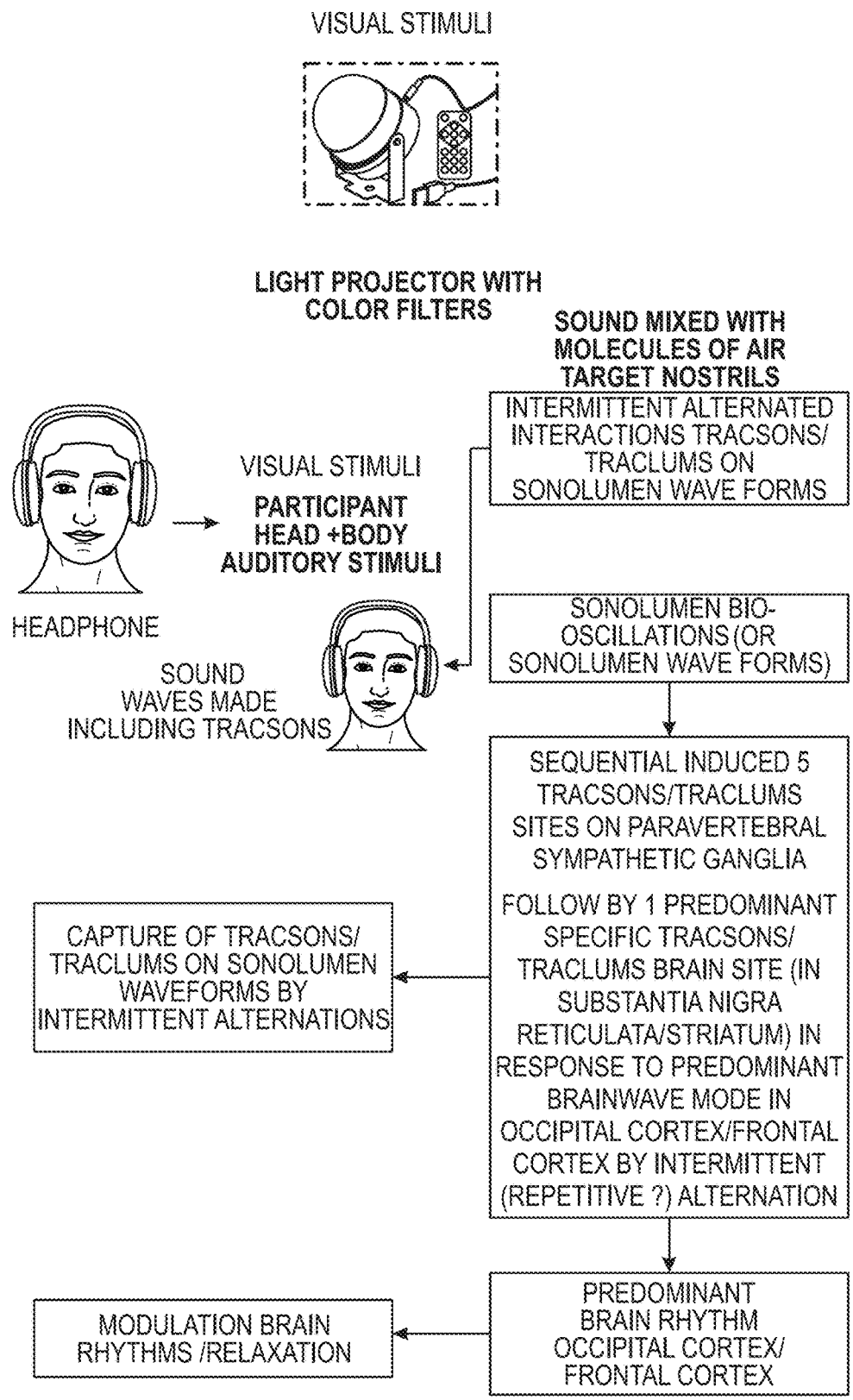
FIG. 3 is schematic indicating the general approach to produce visual stimuli associated with the SBOT and is a general approach for how to balance individuals in need of underactive and overactive brain activity. This schematic is geared toward stimulation of brain rhythm using the occipital and frontal cortices.
Figure 4A:
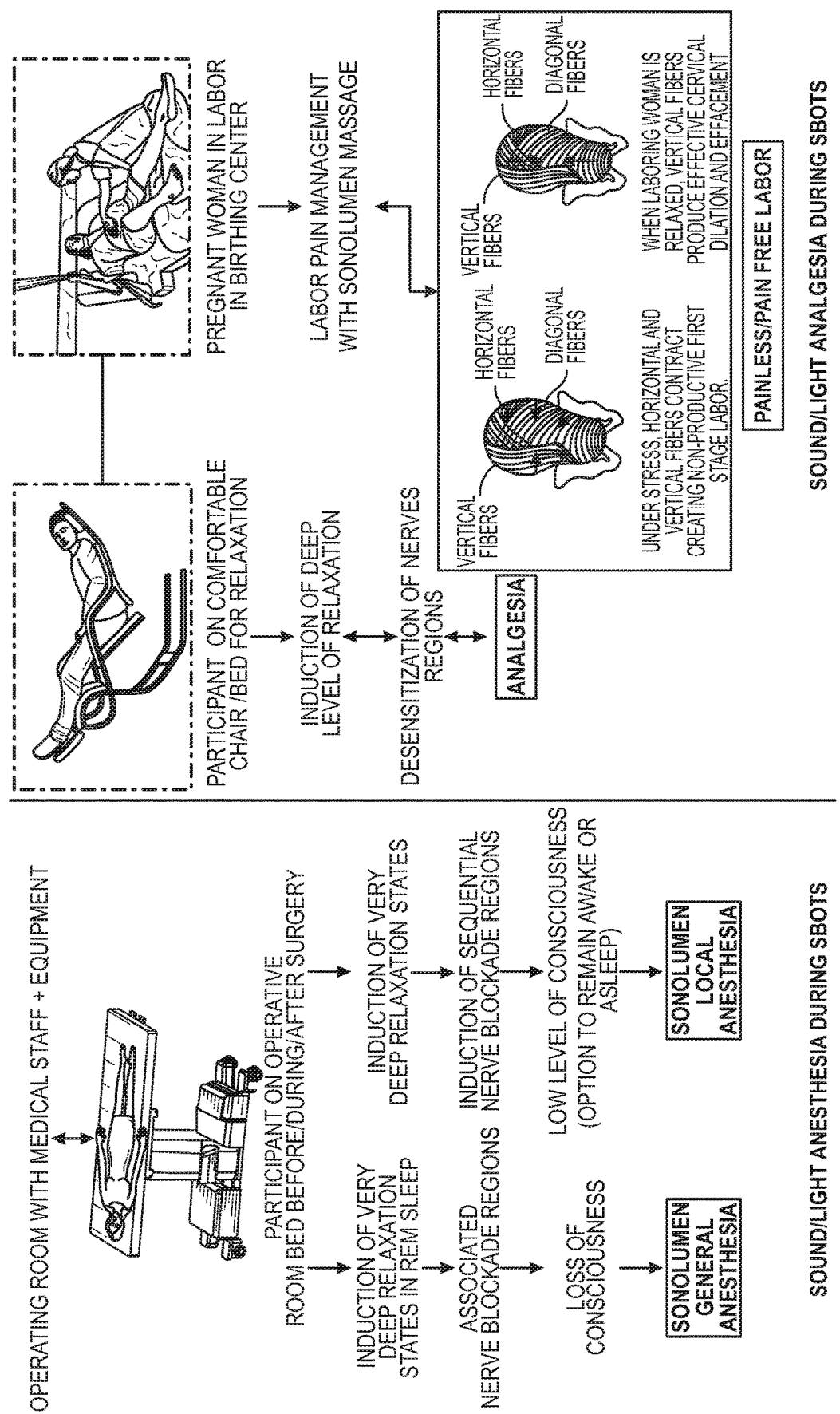
FIG. 4A is a schematic that indicates how the SBOT(s) can be used to induce relaxations states, provide analgesia, labor pain and other pain management, and reduce pain induced by other stressors.
Figure 4B:
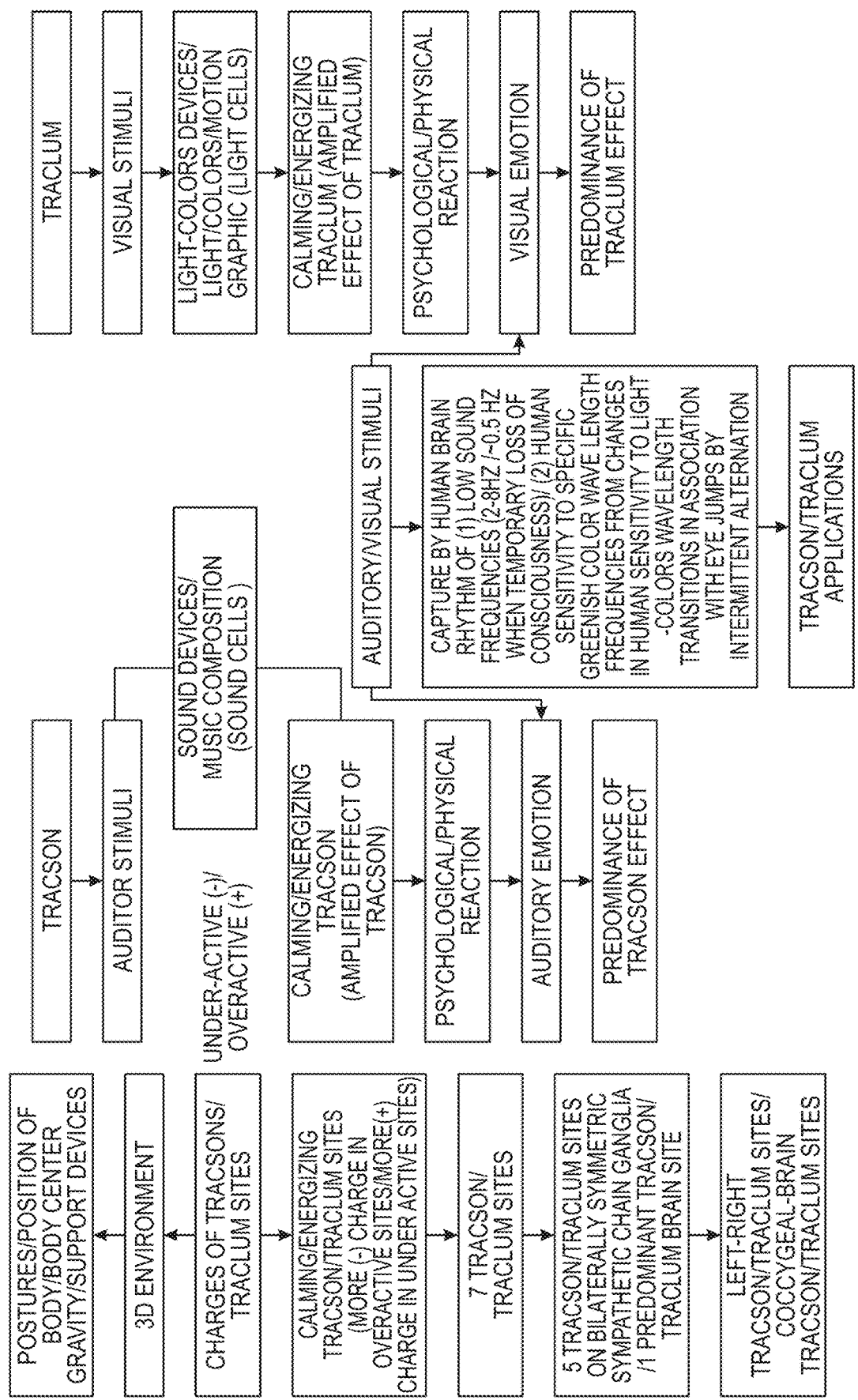
FIG. 4B is a flow chart describing the implementation of SBOTs based upon the use of tracsons/traclums.
Figure 4C:
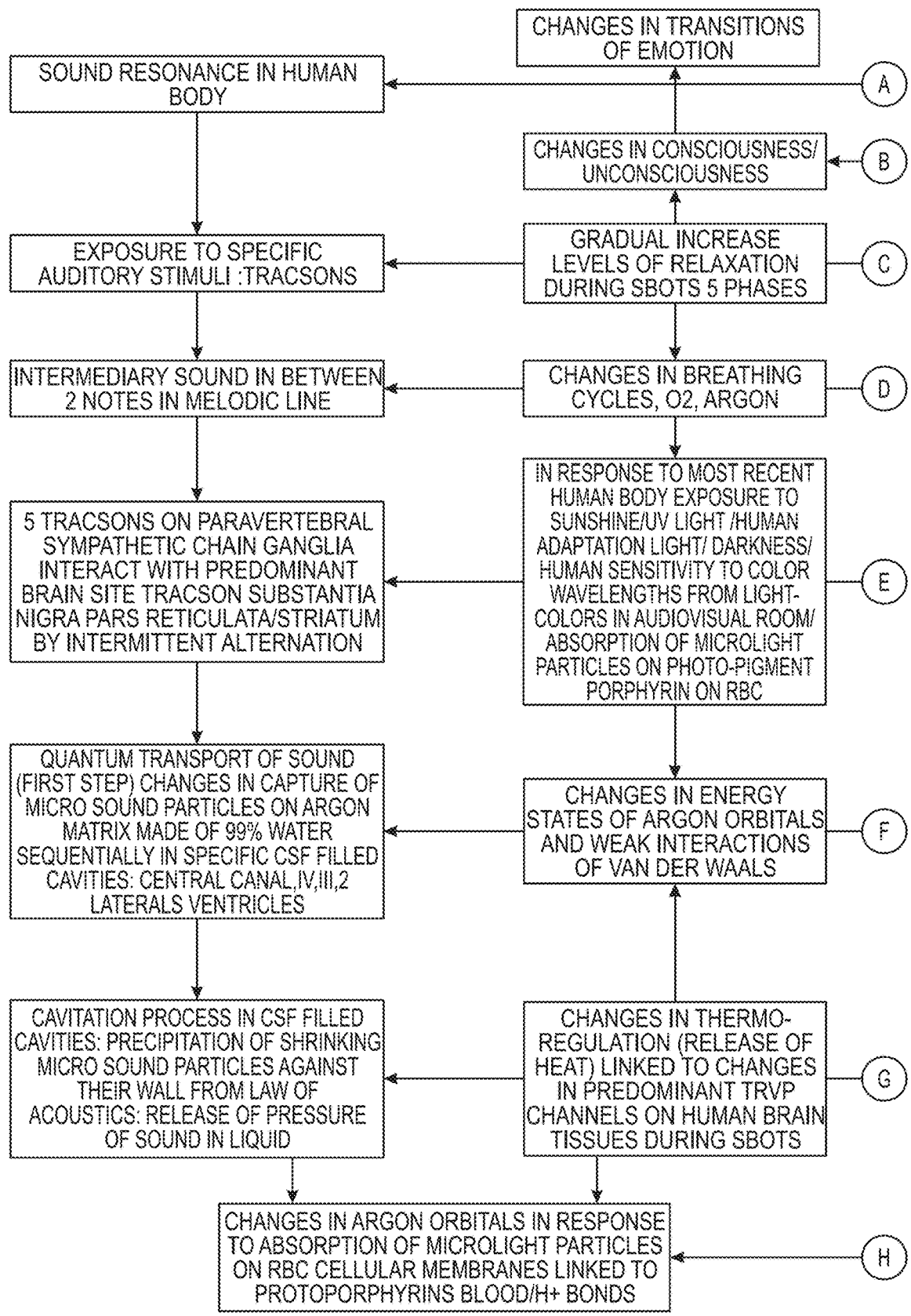
FIGS. 4C through 4F provide a describes SBOT microsound/microlight particles and their tracsons/traclums correlation F—in a flow chart for SBOT process and applications
Figure 4D:
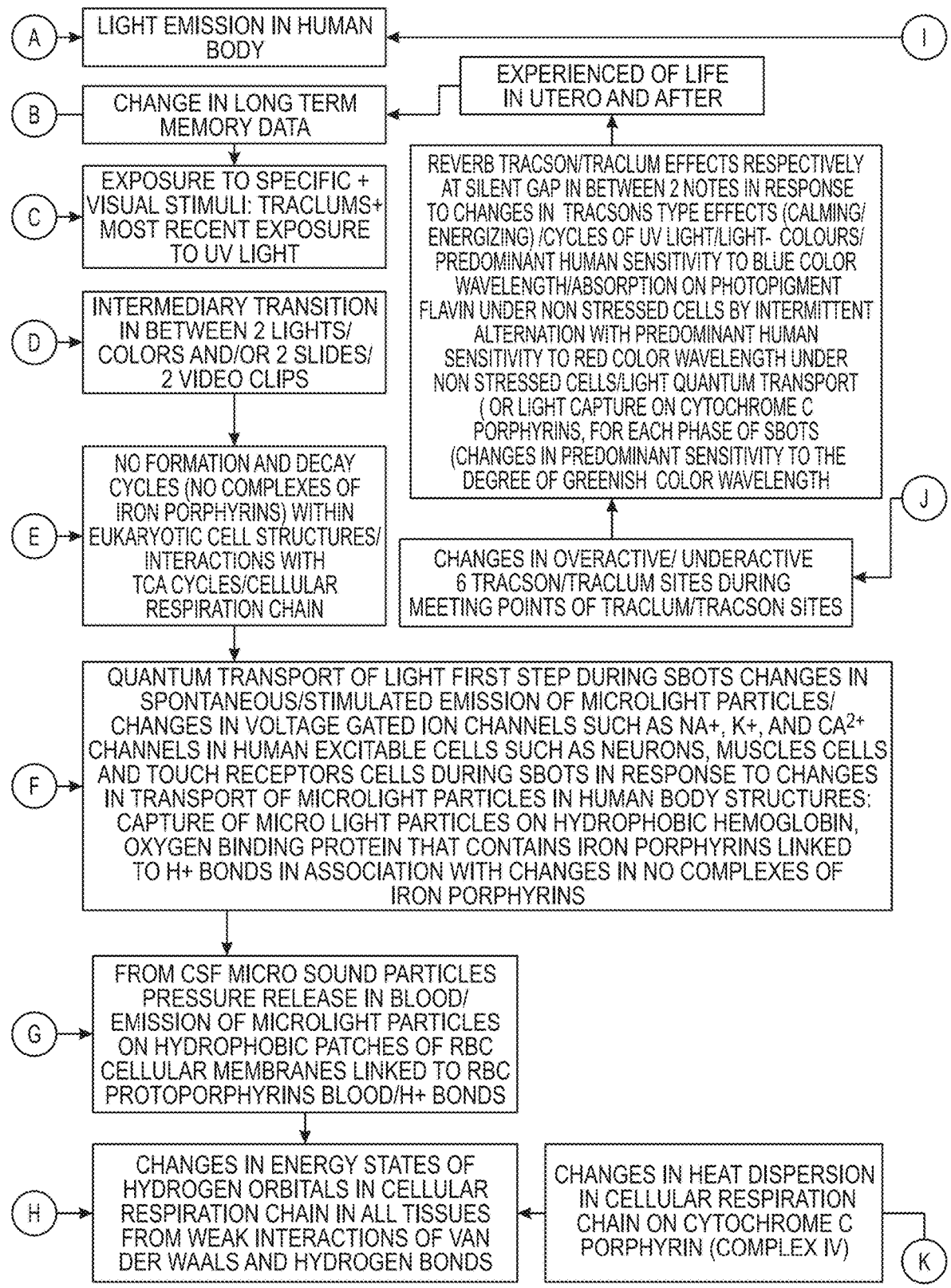
Figure 4E:
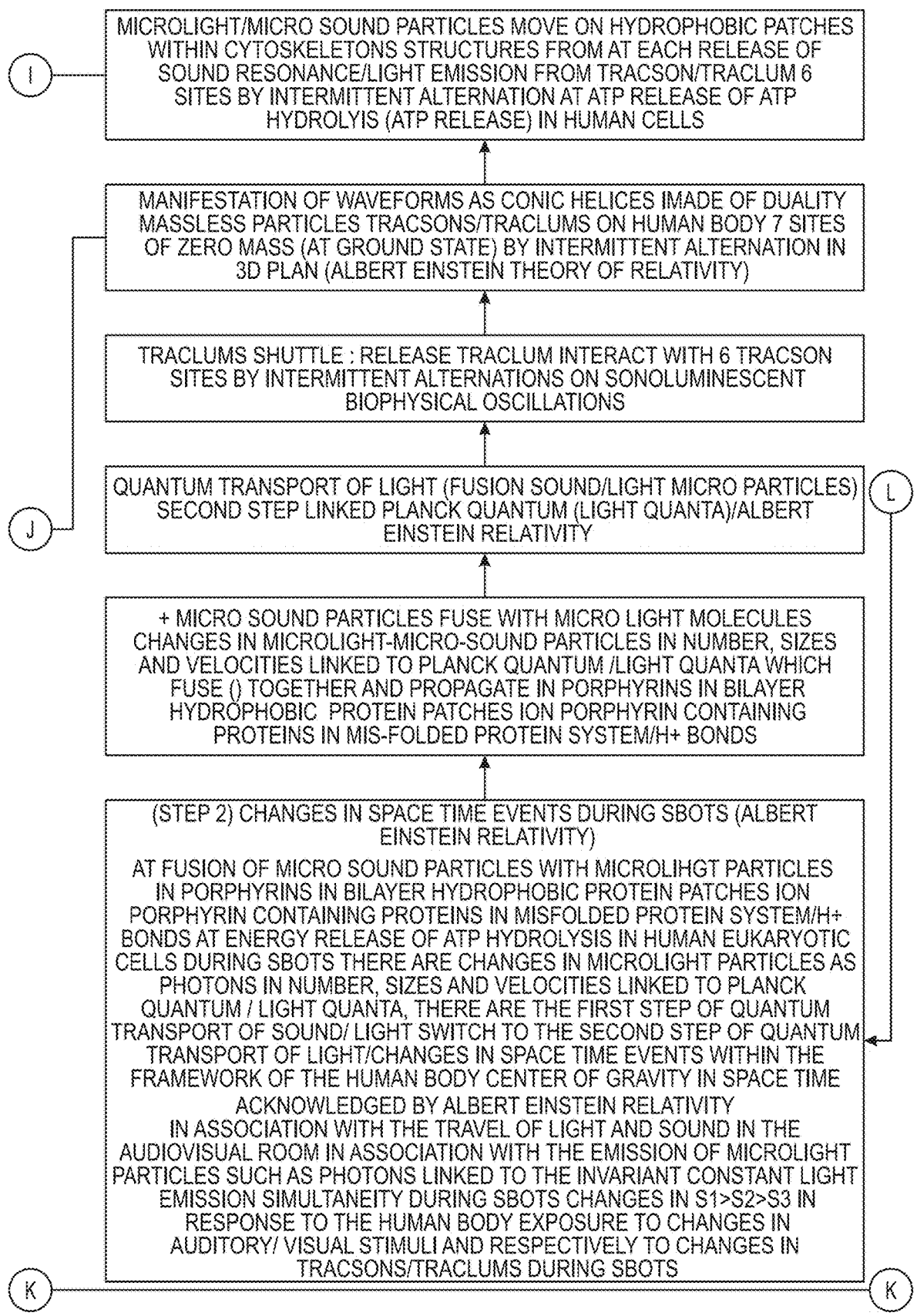
Figure 4F:
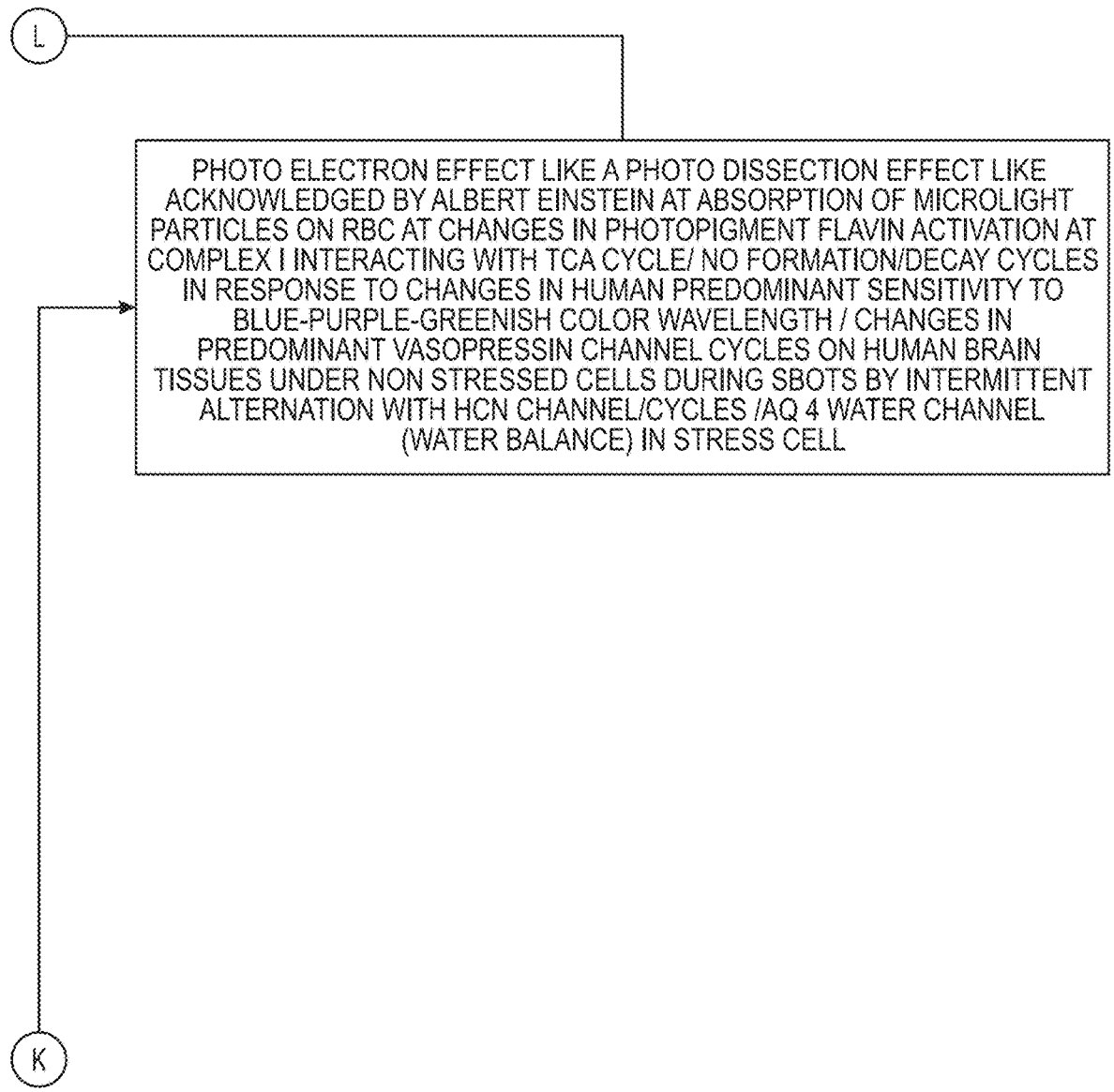
Figure 5A:
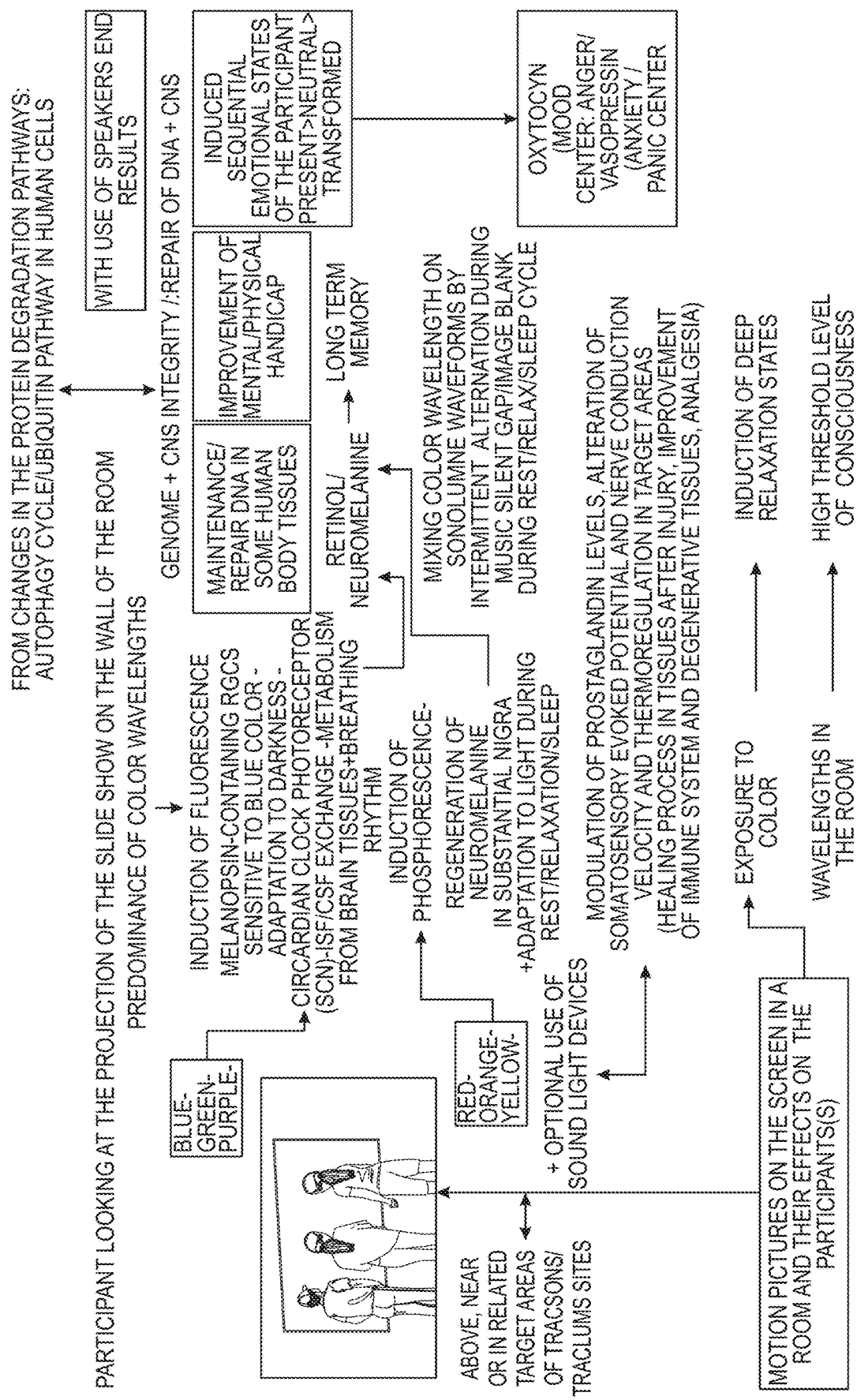
FIG. 5A is a schematic that indicates how and why of using light and color with the SBOT(s) in order to overcome pain from various causes as well as reduction of anxiety, anger, and depressed states (for improving emotional stability).
Figure 5B:
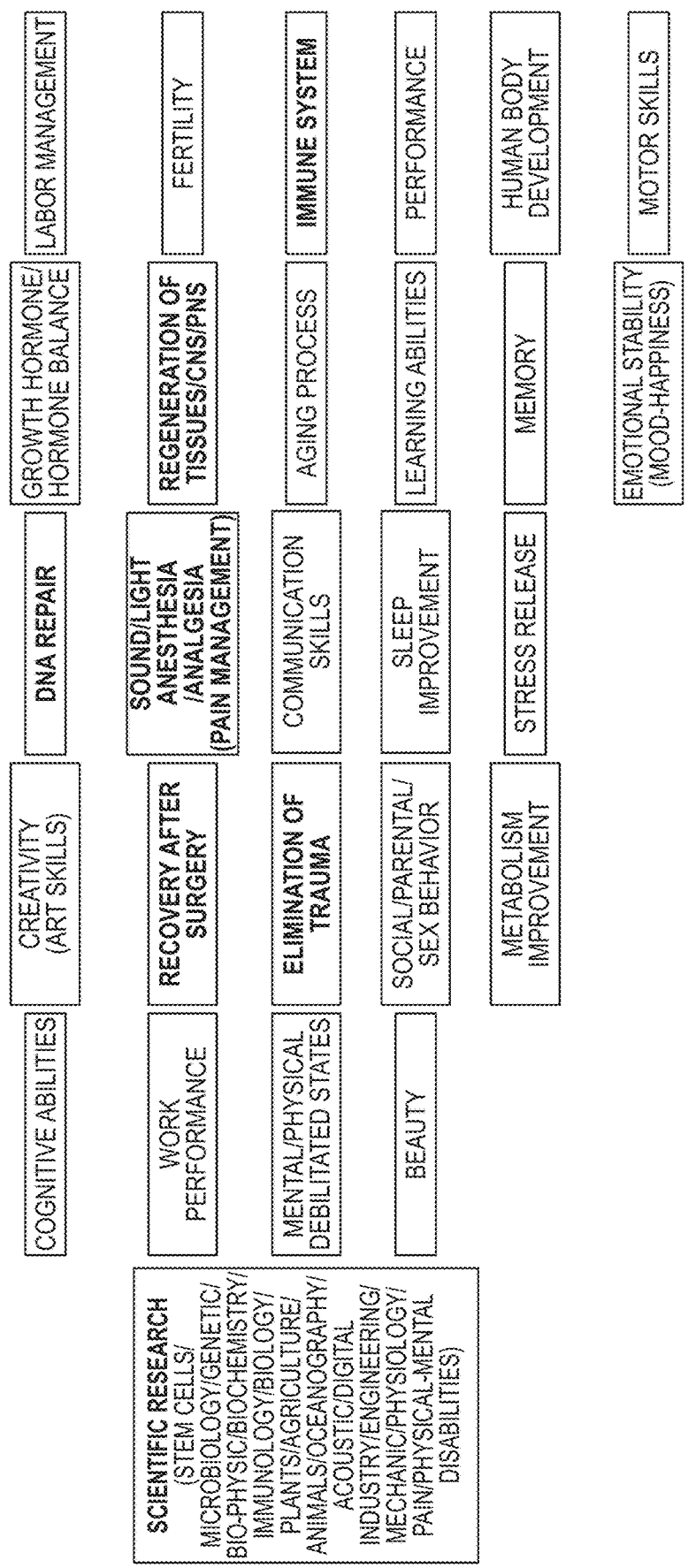
FIG. 5B illustrates the advanced technology, sound-light devices, digital industry devices and tools specifically for work with the handicapped individual.
Figure 5C:
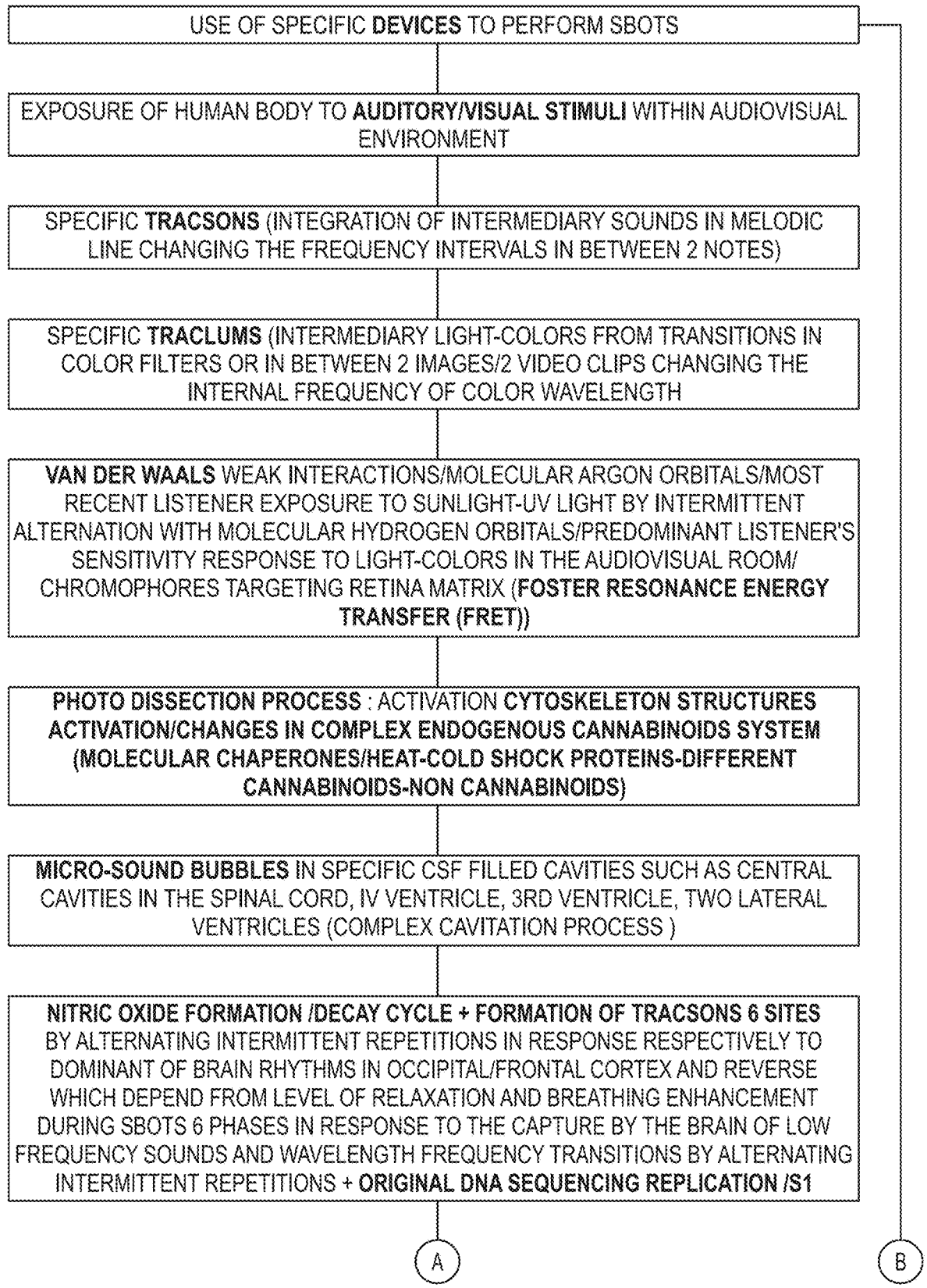
FIGS. 5C and 5D describe, in summary, the processes of SBOTs from initiation to termination of stimuli.
Figure 5D:
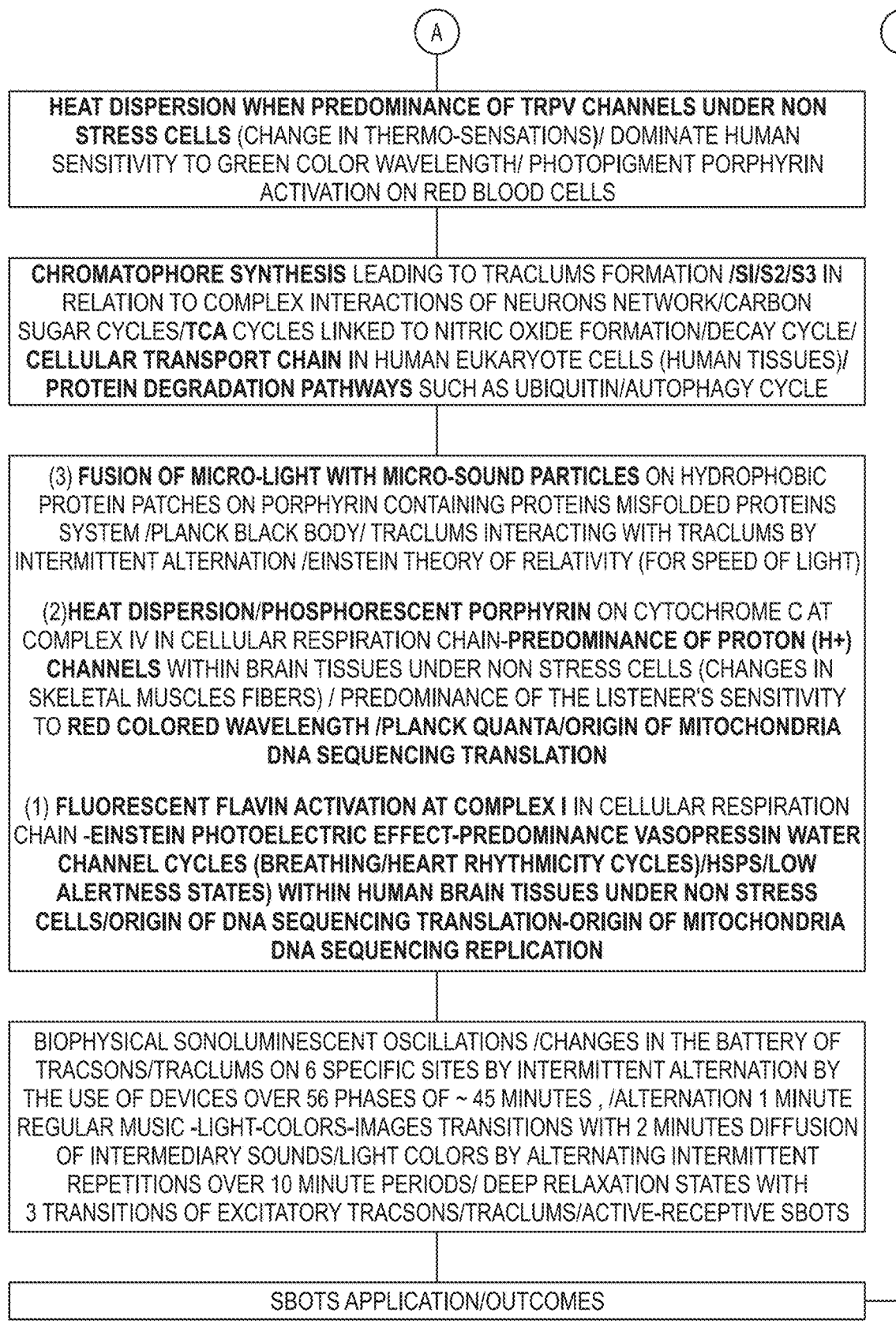

The sonoluminescent biophysical oscillations SBOT(S) of the present disclosure induce deep states of relaxation for the participant(s) with the goal of achieving transition levels of initial and subsequent relaxation states progressing toward very low states of alertness starting with Phase 1-2 transitions, followed by Phase 2-3 transitions, and next Phase 4-5 transitions as shown in FIGS. 1-5 as well as what is shown in a summary of the process shown in FIGS. 5C and 5D and supporting FIGS. 4A and 5A During this process, changes concurrently appear with a concentration of the microsound bubbles that are transported through specific cerebrospinal fluid (CSF) filled cavities sequentially including sections of the spine that include the central spinal canal, the 4$^{th}$ ventricle, the 3$^{rd}$ ventricle and the 2 lateral ventricles. This is also described in the Glossary/Appendix A provided in Provisional application 63/009,912 filed on Apr. 14, 2020 the entire contents of which are incorporated by reference into the present disclosure.

Figure 6A:
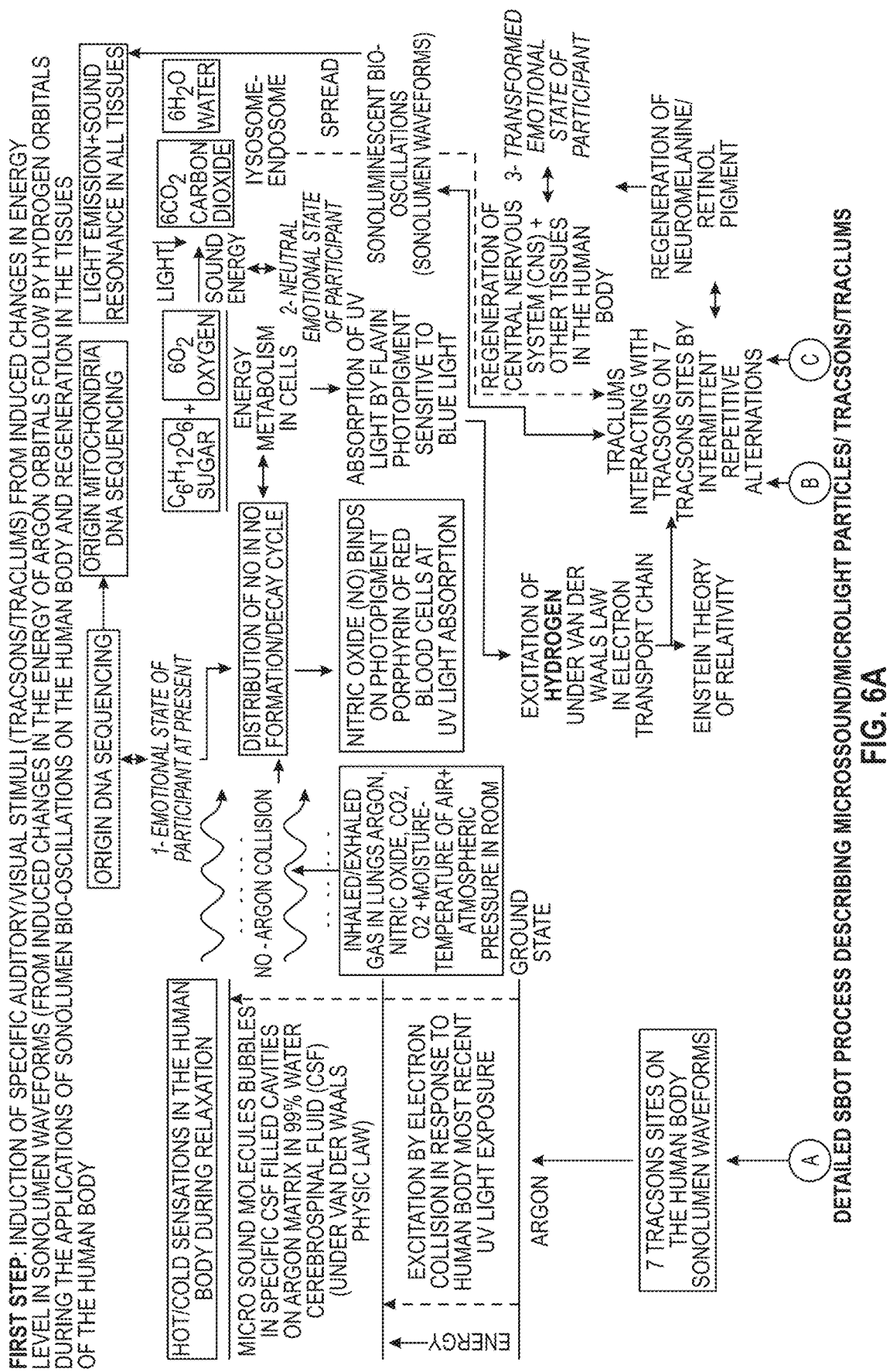
FIG. 6A is a "first-step" schematic that indicates the how and why of using auditory/visual stimuli from induced changes to accomplish various levels of relaxation states during SBOTs that also cause a reduction of human body alertness. This is in connection with sonolumen waveforms that cause molecular changes in DNA that leads to regeneration of the CNS (central nervous system). In addition this phenomenon provides for release of ATP energy from the cells, changes of light emission and sound resonance in all tissues as well as cellular changes that include changes in the brain wave activity of individuals struggling with various states of health.
Figure 6B:
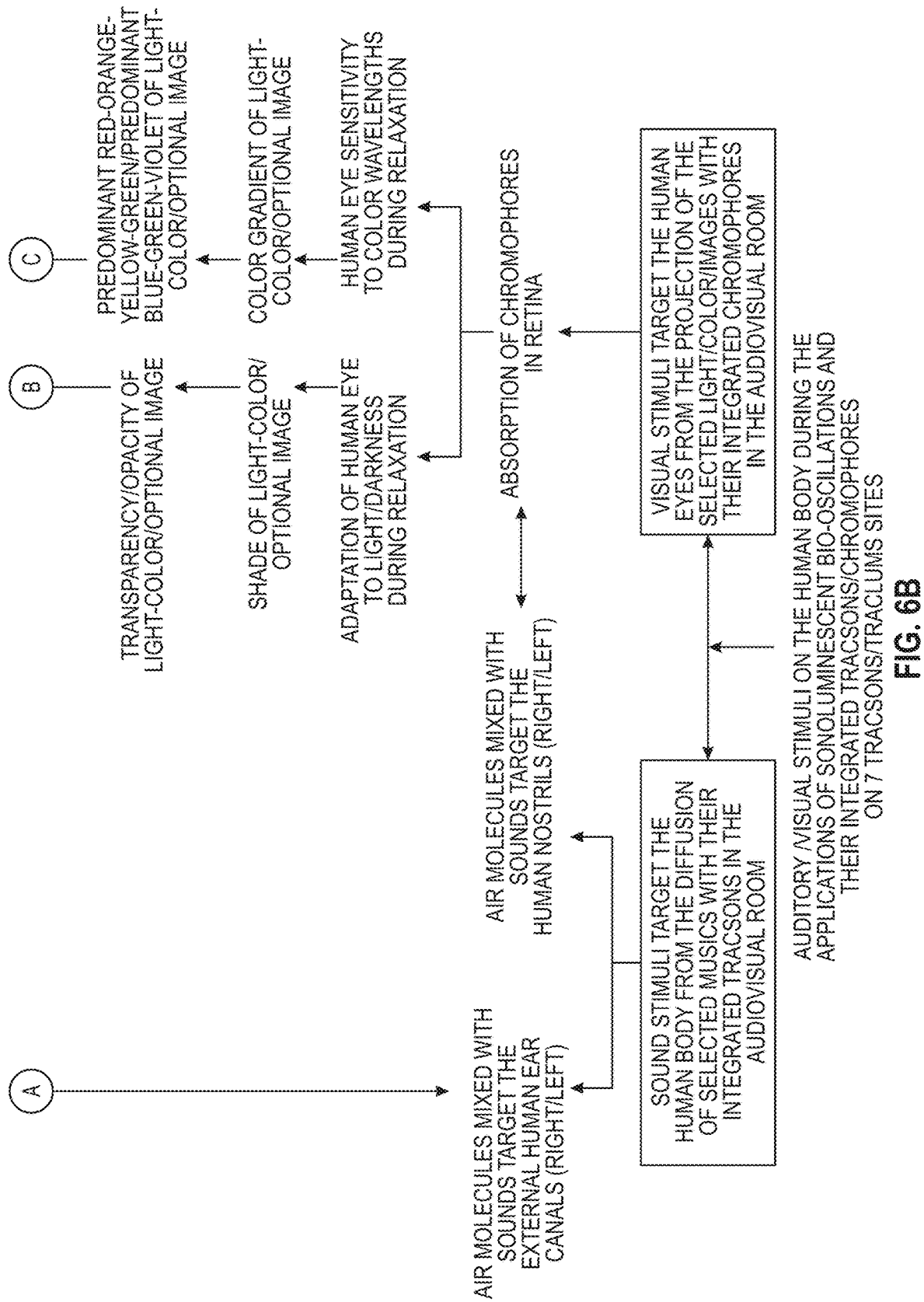
FIG. 6B is a schematic that further describes certain processes shown in figure of 6A, specifically, the change in molecules that collectively compose air which targets the human ear canals, the absorption of chromophores in the retina (eye) and how the target is stimulated by the use of light and colors. This overall process leads to stimuli received by the human body due to the application of SBOT(s) that result in an improved state of health.

During SBOT applications to the participant, induced sequential changes within the participant's/recipient's body due to excited neurons interacting within a network occur. This is shown with the sequential schematic and graphical depictions provided in FIGS. 6A-6C as well as FIGS. 7A, 7B, and 7C. FIG. 7C indicates how color shifts for SBOTs are provided and how they induce biophysical changes.

A. During the SBOT Phase 1-2 transitions, increased changes in the LC-adrenergic system occur and neuromelanin-containing noradrenergic and dopaminergic neurons in the locus coeruleus related to the substantia nigra pars compacta. Consequently, changes are found in the participant/listener's thermo-sensation response (cold/heat sensations), pain sensations, and other sensory responses. In many cases, the listener/participant experiences additional temporary compression in the neck-throat-tongue in fractions of a second and this phenomenon is also associated with changes in sensory responses of other parts of the body. In addition, increased activation of TRPV channels occurs for the non-stressed cells which translates to a concurrent build-up of tracson accumulations on six (6) specific sites that are provided during alternating intermittent repetitions. Also experienced during these transitions are an increased concentration of microsound bubbles that travel through the cerebrospinal fluid (CSF) in the central canal of the spinal cord, and then toward the 4th CSF filled ventricle in the brainstem. This process is manifested as a temporary compression that is often experienced by the listener/participant in the neck-throat-tongue, the sensation of which may only be felt for intervals lasting a fraction of a second. In that sense, the changes experienced are due to excitation of a complex network of neurons that are contained in the cerebrospinal fluid in the spinal cord. There is also an increase of concentration of microsound bubbles in the central canal of the spinal cord which force their way into the 4th ventricle in the brain stem. Concomitantly, there is a dominant sensitivity response of the listener to green colored light wavelengths that change the activation function associated with porphyrin photopigment on the red blood cells. This sensation indicates a provision for human sensitivity increases and more dramatic responses to green colored light wavelengths. This process is also linked to induced changes in the nitric acid NO formation and decay cycle again resulting from alternating intermittent SBOTs. The listener/participant then experiences the loss of stress from past life experiences until the present. These techniques provide a path for the participant to "let go" some of the past reminiscences (dominantly unconscious thought being greater than conscious thought).

Figure 8:
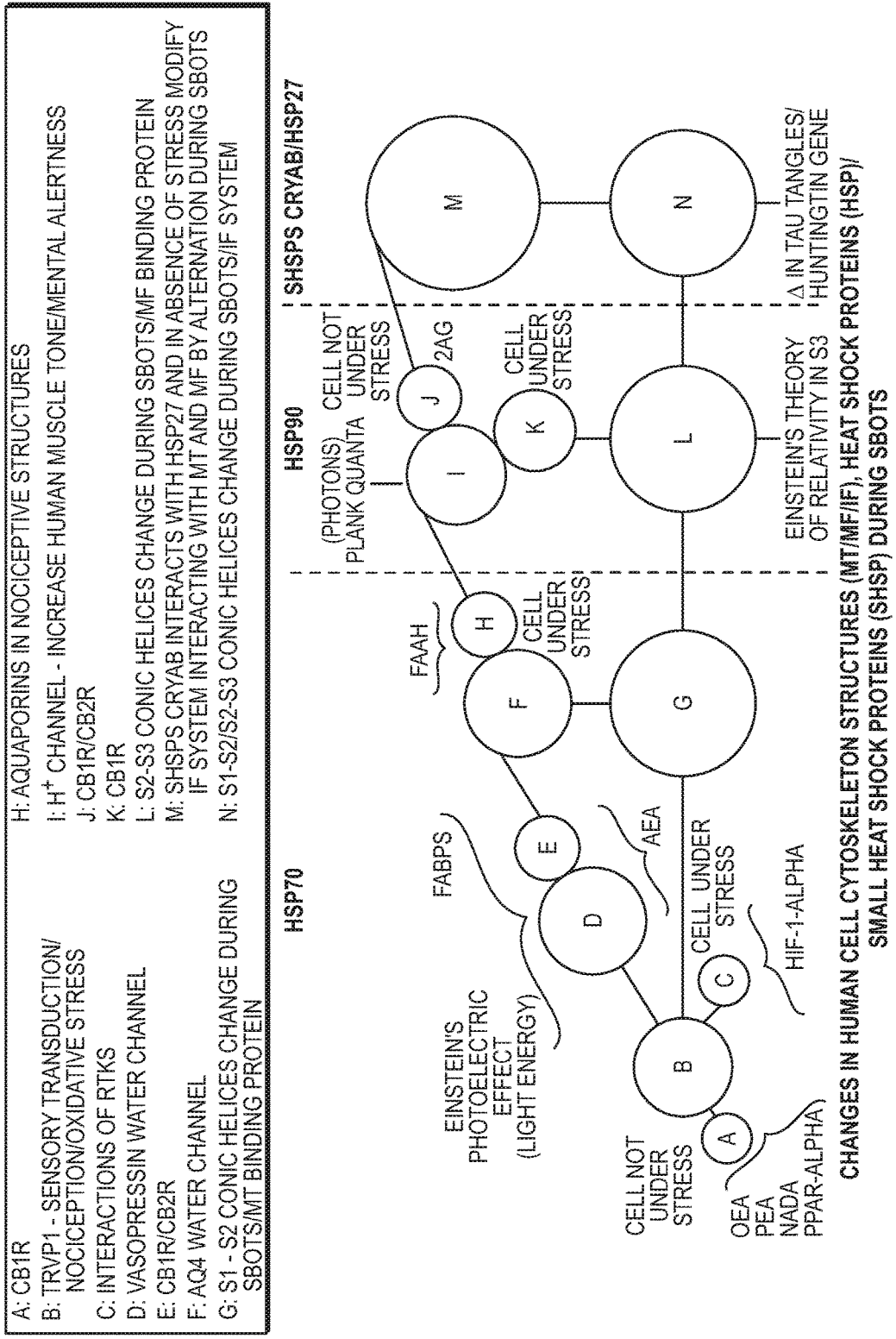
FIG. 8 is a tabulation of changes in cytoskeleton structures during SBOTs that are in association with changes in heat shock proteins (HSP) which function as molecular chaperones and facilitate the synthesis and folding of proteins.
Figure 10B:
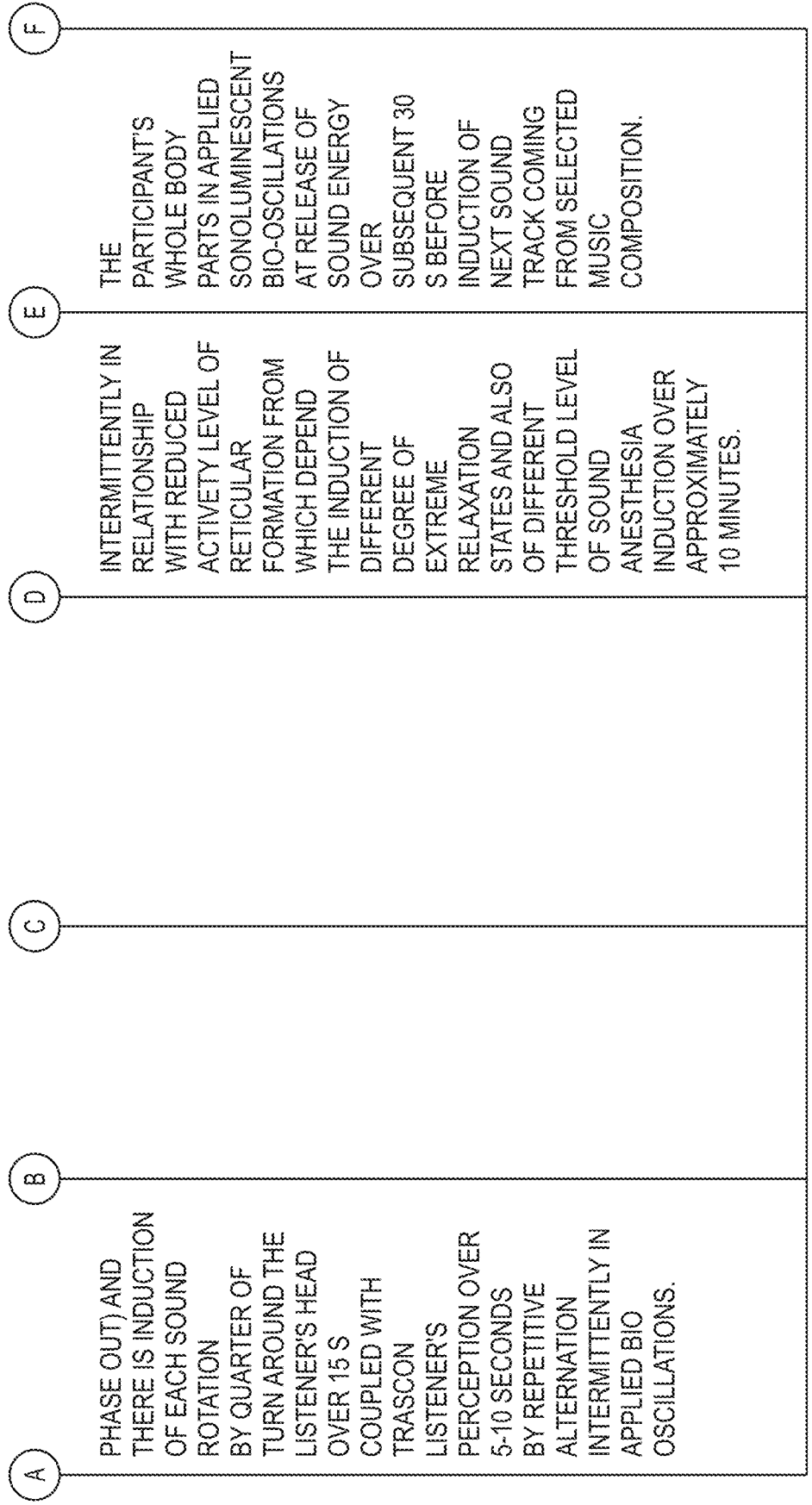

B. In addition, an ability to provide for a gradual and simple transition of the dominant brainwave modes transiting from the occipital cortex toward the frontal cortex. Here TRPV channels interact with complex neuron networks of neurons that involve thermo-sensation in response to the signaling of calcium $Ca^{2+}$ and $Mg^{2+}$ transport capabilities that exist in the plasma membrane. This biophysical mechanism activates the immune system within the brain tissues through the activation of heat shock proteins (HSP) as shown in FIG. 8 versus cold shock proteins (CSP) that are energized and respond more during sonoluminescent massage applications (described in more detail in the Glossary/Appendix A provided in Provisional application 63/009,912 filed on Apr. 14, 2020 the entire contents of which are incorporated by reference into the present disclosure.) The TRPV channels mediate a variety of sensations including pain, temperature, different kinds of tastes, pressure, and vision, while facilitating many signaling pathways that allow for sensory transduction, nociception and oxidative stress.

(2) For the SBOTS Phase 2-3 transitions, there are increased changes in the middle ear cavity associated with the cordi tympani complex networks of neurons, and there is also an increase concentration of microsound bubbles that travel from the CSF filled 4th ventricle cavity toward the CSF filled 3rd ventricle cavity. The listener may experience more compression temporarily toward his ears by fraction of seconds (tingling, changes in temperature, sensation, etc.) in association with sensory changes in his remaining body parts, and his level of relaxation intensifies. This process is well depicted in the sequential FIGS. 9A-B, 10A-B and 11A-B. The listener/participant becomes more sensitive to red colored wavelengths of light vs. blue colored wavelengths of light (which can be reversed) by the use of alternating intermittent SBOT applications that cause proportional changes to transitions of increased dominant brain wave modes in the occipital cortex versus those in the frontal cortex (and this process likewise can be reversed). As these phase 2-3 transitions progress, there is an increase of proton H channels within human brain tissues on the right side hemisphere that leads to an increase in the listener's/participant's mental awareness. (this helps strike a balance between conscious/unconscious thoughts) within a deep relaxation state. In this case the dominant brainwave mode occurs with more intensity in the occipital cortex.

As a result, the listener experiences changes in their subjective feelings at one instant in the present (based on present) which assists with determination of a biophysical state of the participant realizing a neutral mode—meaning that the listener/participant acknowledges transformation in their reminiscence. This transformation at least partially releases the participant from the burdens of previous and current life experiences including past trauma, frustrations, difficult memories, etc.). At this point, there is a dominant listener sensitivity response to red colored wavelengths in relation to the changes in the increased activation of porphyrin activation in cytochrome C at complex IV in the cellular respiration chain for non-stressed cells. This is again in response to alternating intermittent repetitions of SBOT that produces changes resulting in decreased fluorescent flavin activation at complex I. In addition there is also an increase in the activation of proton H$^+$ channels within the human brain tissues, leading to an increase in overall muscle tone as well as mental alertness rising. The proton H$^+$ channels involve the activation of skeletal muscles to maintain a proper posture during deep relaxation states. This also contributes to the changes in dominant brainwave mode in the occipital cortex leading to a more advanced state of mental alertness.

(3) As the SBOTs are further applied with the Phase 4-5 transitions, the response includes a concentration of the microsound bubbles transiting from the 3rd ventricle CSF filled cavity toward the two (2) lateral ventricles and an increase of dominant brain waves mode that now appear primarily in the frontal cortex. There is an increased activation of vasopressin water channels in the brain tissues in response to a deeper induced level of relaxation (nearly a state of sleep) along with an increased change in the rhythmicity of the breathing cycle/heart rhythmicity cycle/ICF/ECE exchange. The listener/participant responds with more sensitivity to blue colored wavelengths of light from increased activation in fluorescent flavin at complex I in the cellular transport chain. The listener/participant also experiences temporarily more compression, and associated tingling sensations, changes in the temperature, and these sensations also occur in fraction of a seconds due to use of the alternating intermittent repetitions in the region of the forehead and eyes. Other sensations associated with this portion of the technique includes remaining body parts—particularly extremities of the hands-fingers and toes-feet. In this manner, the participant's subjective feelings (the emotions being conveyed at the time) evolve toward a more emotional stability going forward in time.

Figure 12A:
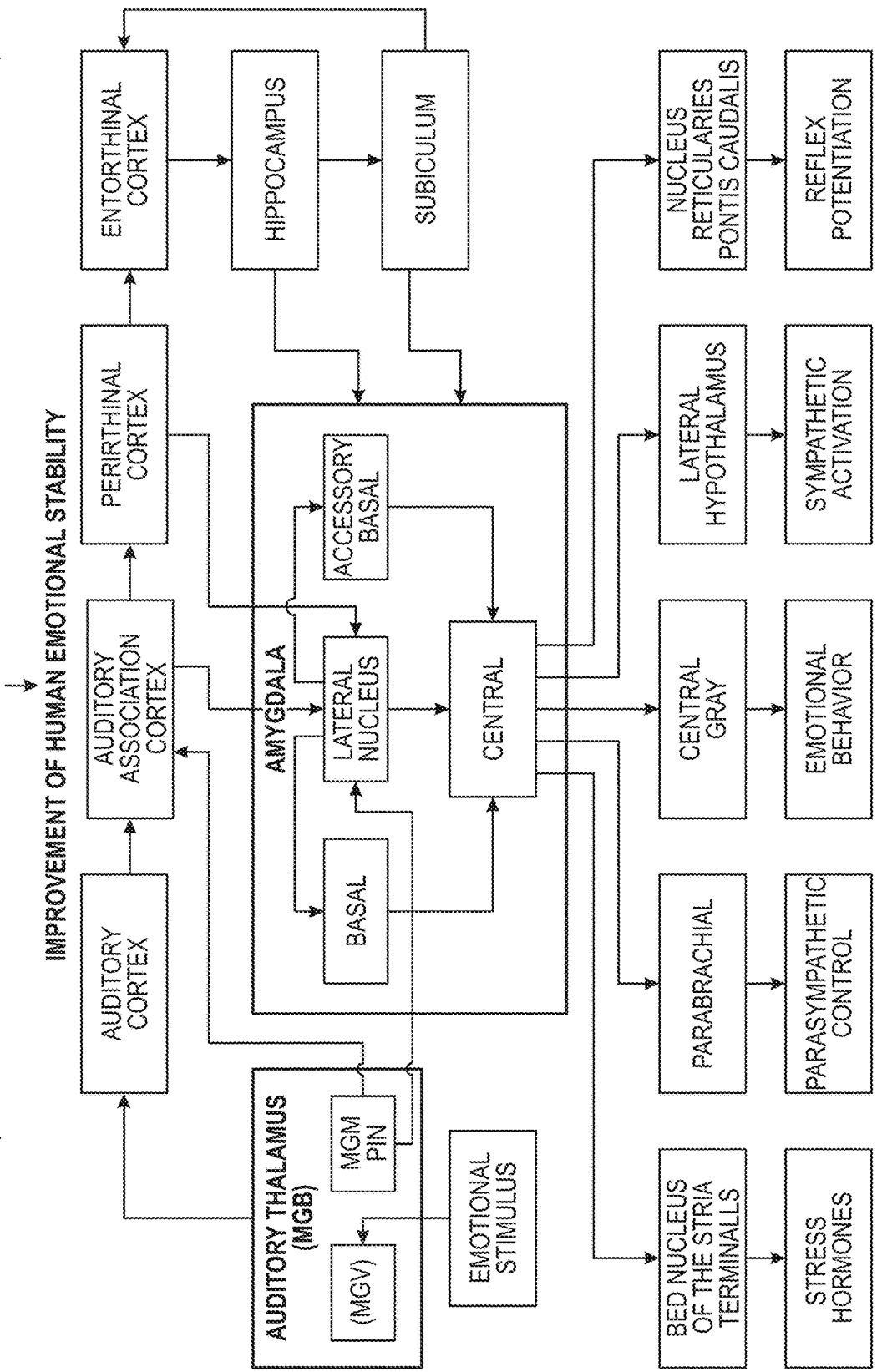
FIG. 12A illustrates the mood center and changes in vasopressin/oxytocin during SBOTs applications with neural networking.
Figure 12B:
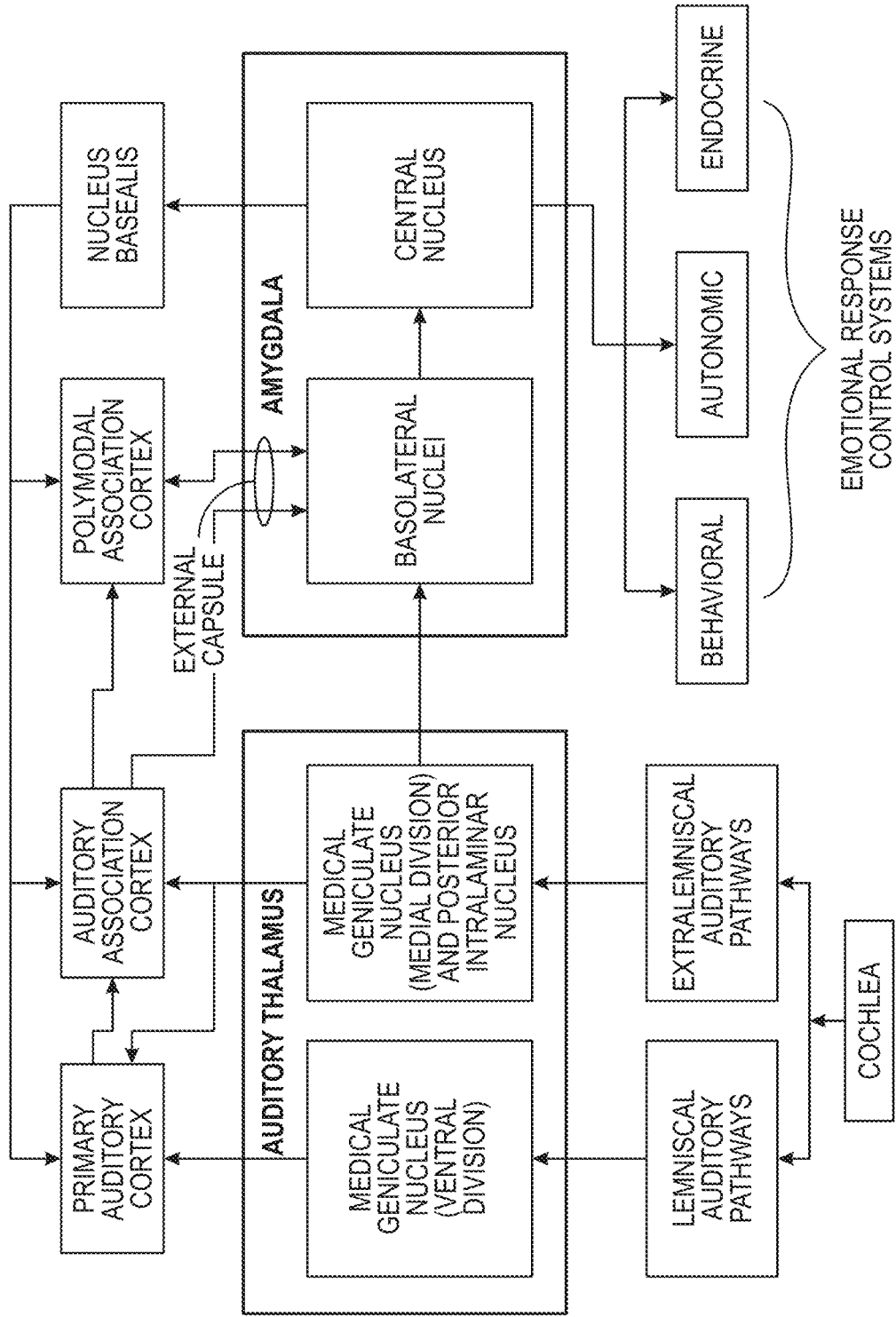
FIG. 12B illustrates the arousal and plasticity associated with neurons.

(4) All processes which occur during the SBOTs transition phases involve invoking and energizing a complex network of neurons related to interactions with heat shock proteins (HSPs), cold shock proteins, molecular chaperones, the complex endogenous cannabinoid system which translates to producing major changes which appear in the physiological states of body tissues that contain stressed and non-stress cells. This is best depicted in appended supporting FIGS. 12A and 12B of the present disclosure. In so doing the SBOTs contribute to major improvements in the health and wellbeing of the participant regardless of the original cause of departure from a healthy physiological state. More specifically, the SBOTs contribute to major improvements in the states of the most severe debilitation in body tissues leading to and including all other possible weaknesses associated with the human body.

Figure 13B:
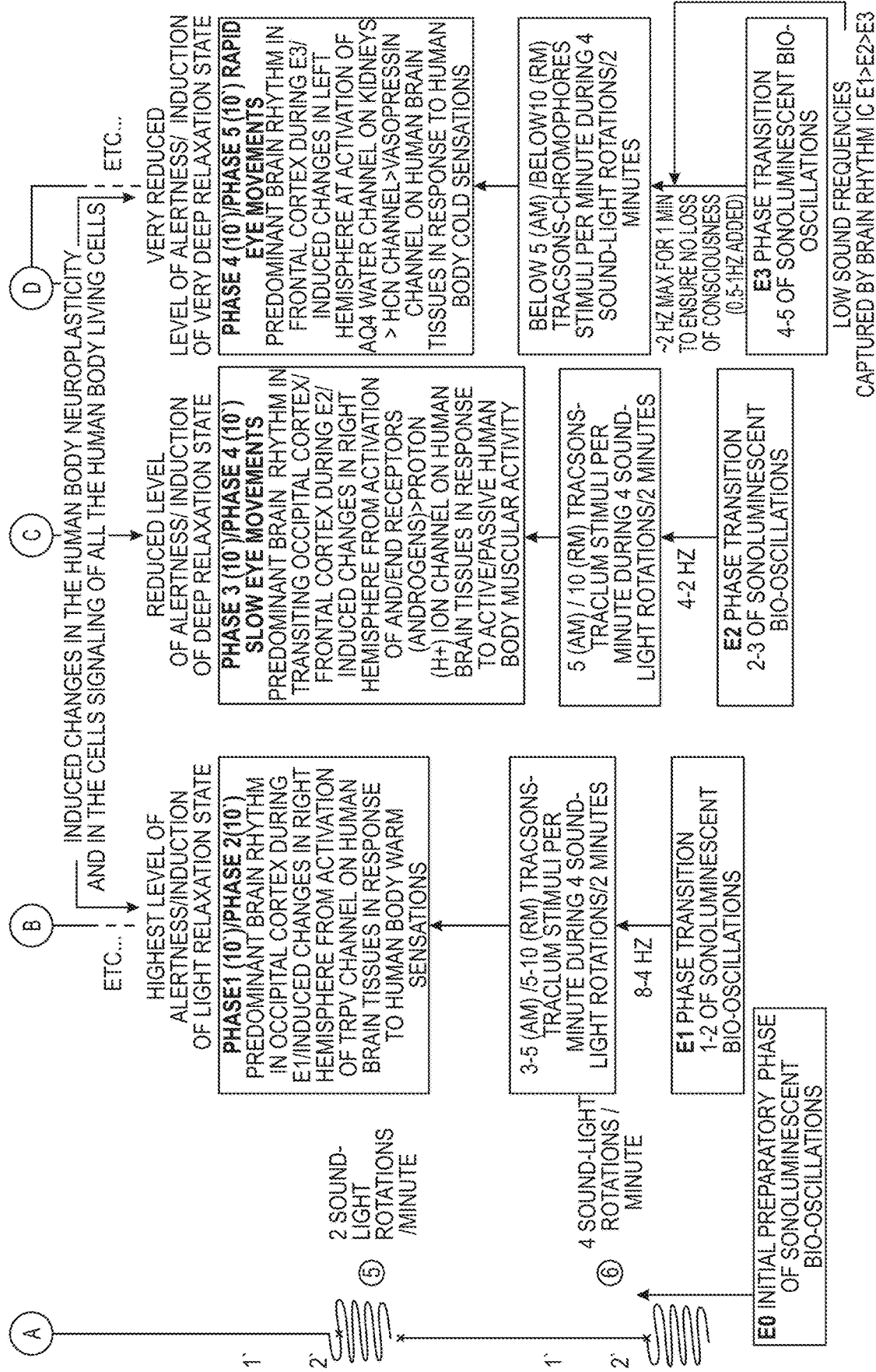
FIG. 13B is a schematic further describing the FIG. 9A schematic but focuses on the induced changes regarding how the neuroplasticity condition in both humans and corresponding biological cells are provided which are a result of the signaling caused by the SBOTs.
Figure 14A:
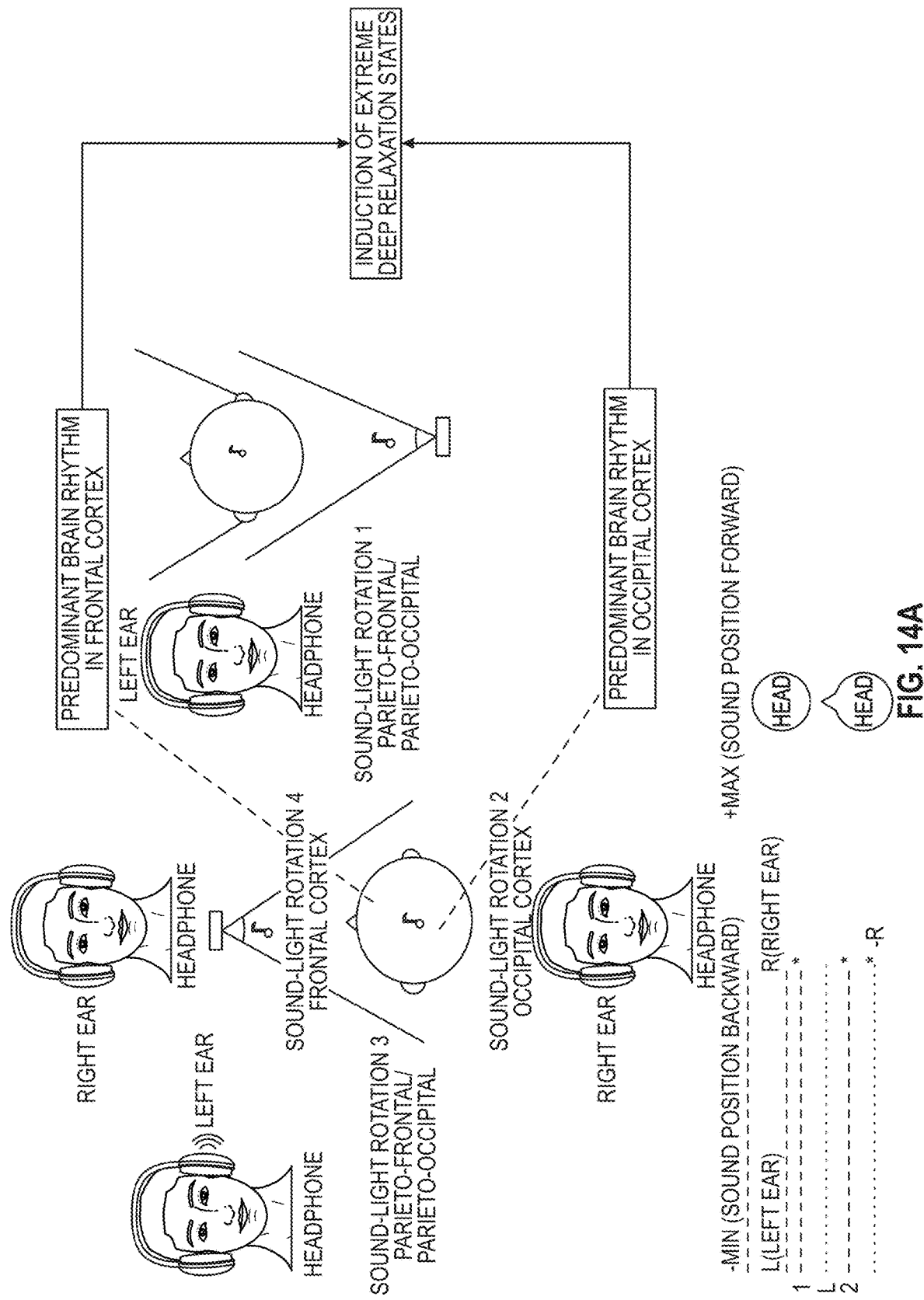
FIG. 14A is a schematic indicating the use of auditory sensory (music/sound, individual melodies, etc.) perceptions delivered by SBOTs to state of health improvements.
Figure 14B:
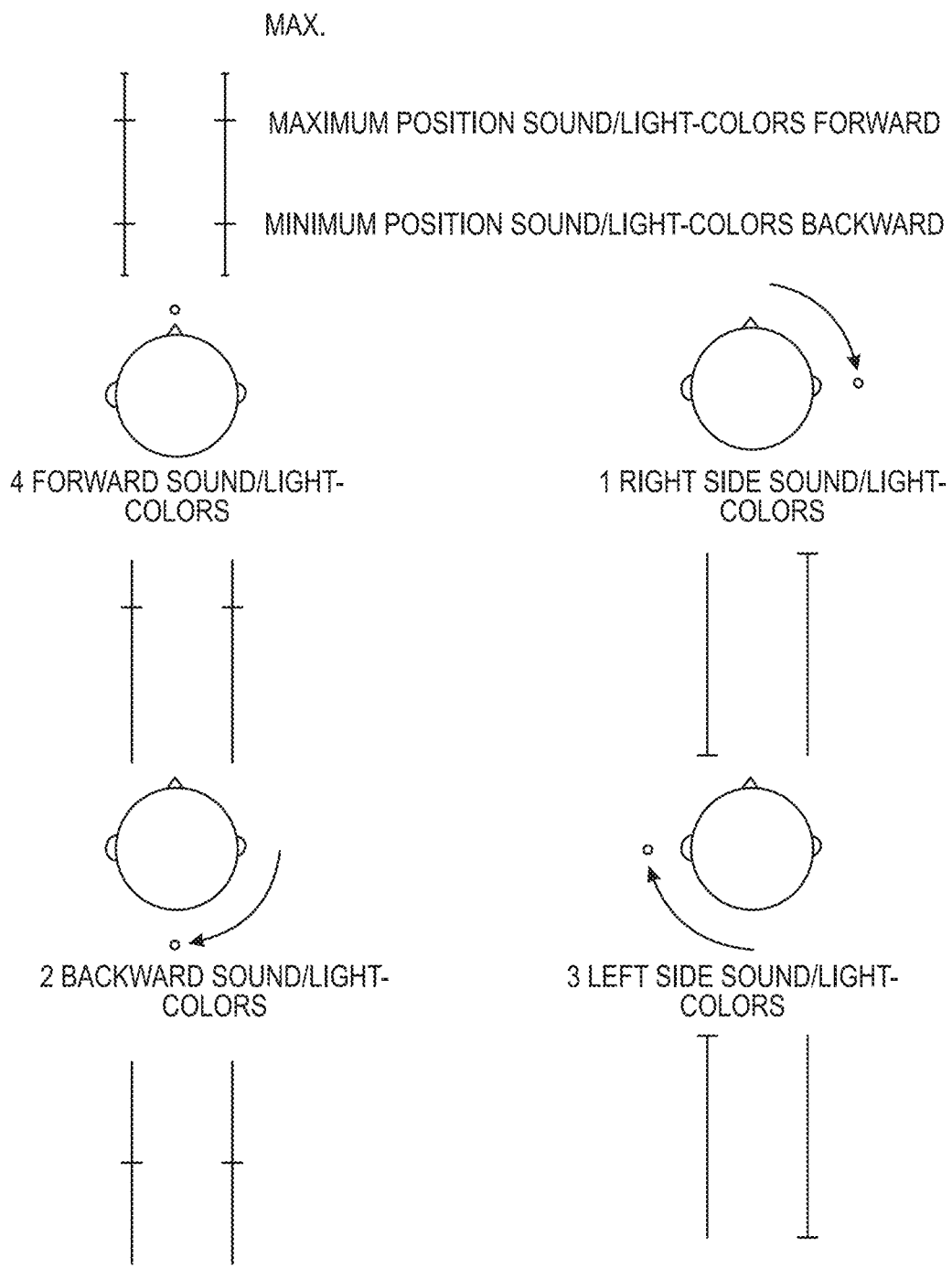
FIG. 14B further describes a schematic of the workings of the use of sound/light/colors for inducing SBOT state of health improvements.
Figure 14C:
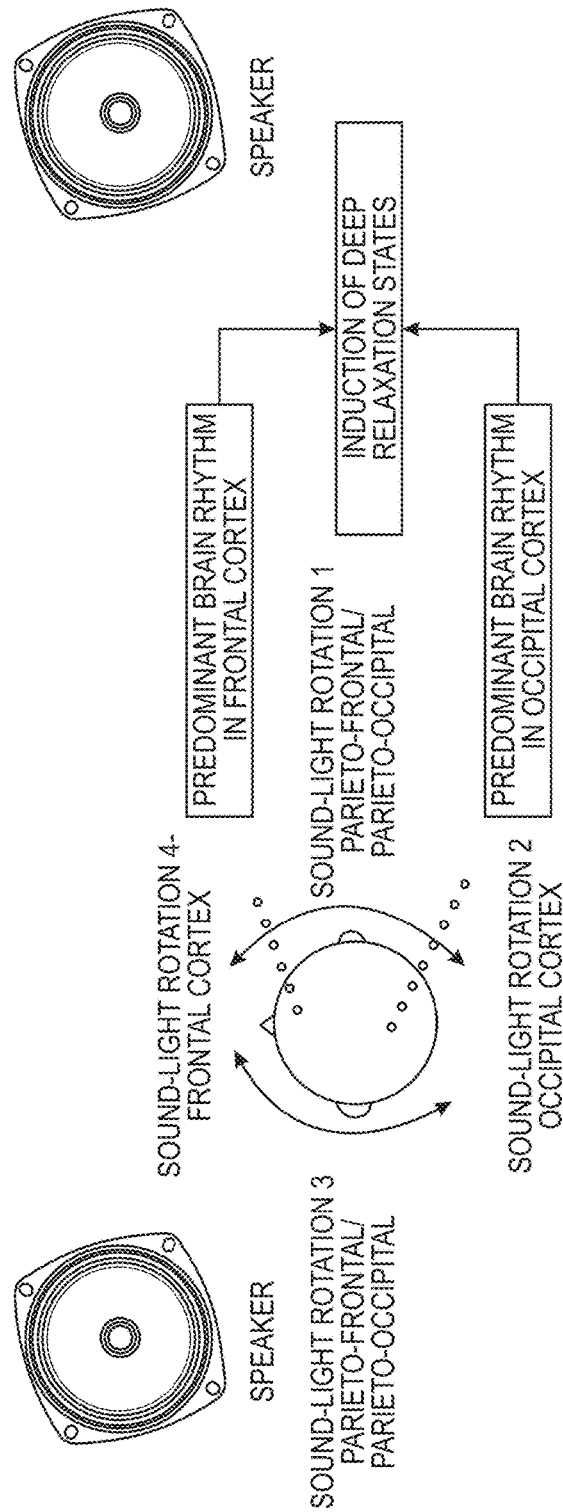
FIG. 14C is a further schematic that illustrated the use of sound-light rotations needed to apply SBOTs for individuals requiring how this influences brain function.
Figure 14D:
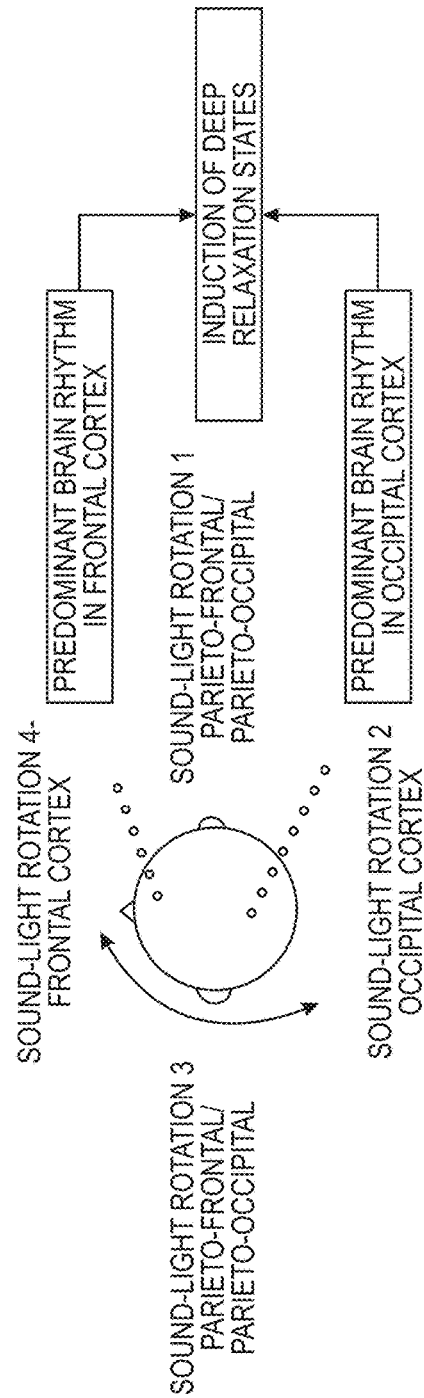
FIG. 14D is a schematic showing the use of sound-light rotations needed to apply the SBOTs to individuals as in FIG. 14C, but without using speakers for achieving similar results.

(5) Subsequent sequential changes in the concentration of the microsound bubbles in specific CSF filled cavities (such as central canal in the spinal cord, then 4th ventricle, then 3rd ventricle, followed by two lateral ventricles) using alternating intermittent repetitions of the SBOTs contribute to the formation of six (6) tracson accumulation sites in response to changes in sound resonance in the audiovisual room from the integration of specific intermediary sound, known as tracsons. This process is well described and presented in original FIGS. 13A-B. The tracsons change the interval frequency in the melodic lines selected and then perceived by the listener/participant. Concomitant changes in the listener/participant's sensitivity with respect to the response to colored wavelengths also occurs within the environment of the audiovisual room made of light and colors and induces changes in the integration of specific intermediary lights/colors. This integration and resulting intermediary changes are known as traclums which are responsible for changes in color filters in the audiovisual room to more intensified intermediary changes in light-colored transitions (in between 2 images or 2 videos clips transitions) that transforms the frequency intervals of colored wavelength. There are changes in the light emission in the audiovisual room that cause changes in the light-color selectivity in addition to changes in the sound resonance coming from changes in music selectivity. This is schematically represented in original FIGS. 14A-14D. It is also shown (in FIGS. 15A and 15B) that the SBOTs which contribute to the formation of six (6) tracson sites interact with the six (6) traclum accumulation sites at meeting points due to interactions that Are produced using alternating intermittent repetitions of the SBOTs.

Figure 16:
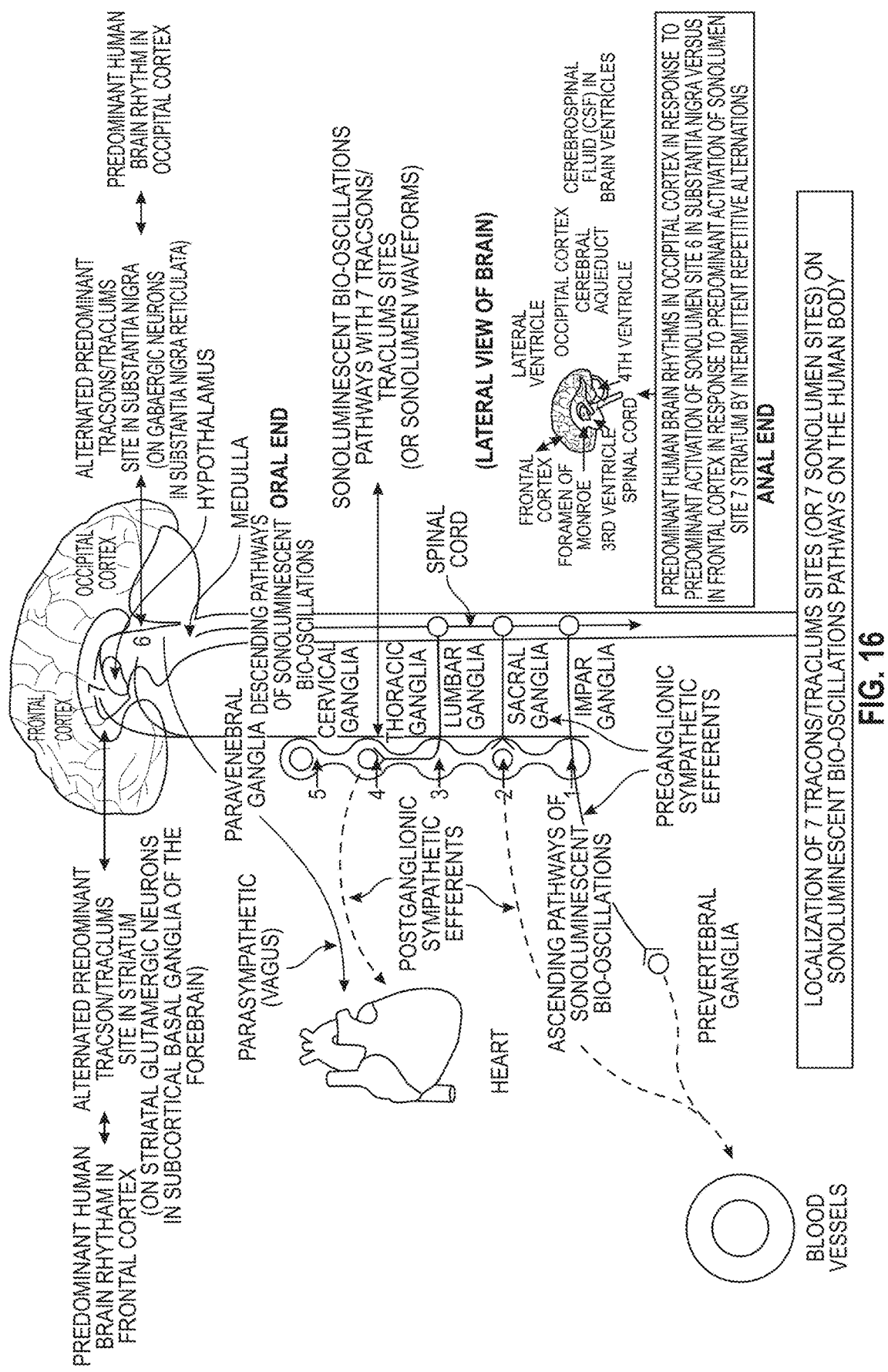
FIG. 16 is a completed schematic that summarizes and connects the information that further illustrates how the tracsons/traclums provide the needed activation for localization of 7 tracsons/traclums sites (or 7 sonolumen sites) on sonoluminescent pathways. These pathways exist for the human body as wave forms of massless particles of duality made from tracsons and traclums but possess zero mass which interacts by alternating intermittent repetitions at the speed of light as defined by Albert Einstein's Theory of Relativity.
Figure 17A:
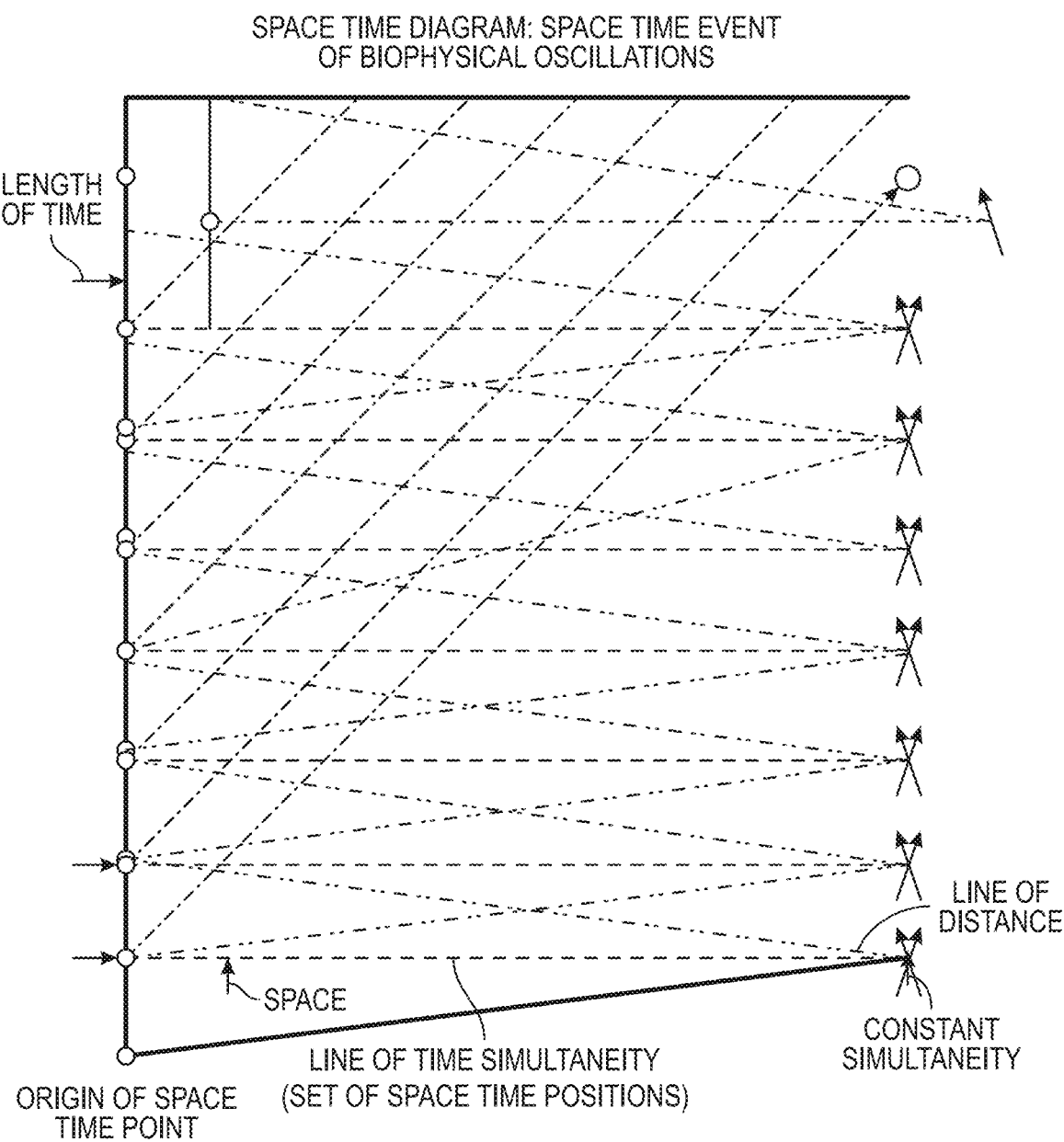
FIGS. 17A-17H illustrates the space time events of biophysical oscillations during SBOTs and changes in two subsequent tracsons/traclums 7 sites interaction and the conical helices associated.
Figure 17B:
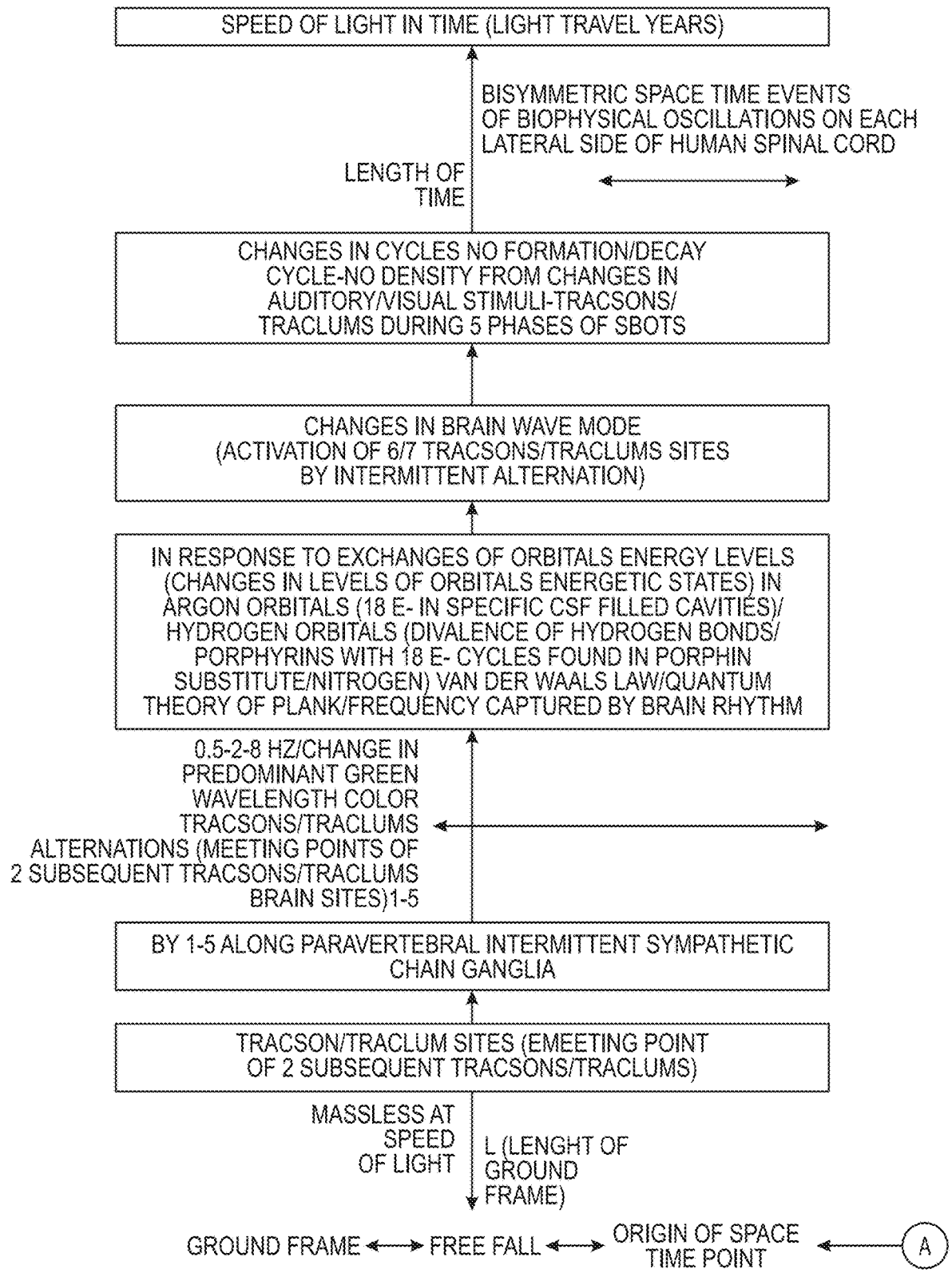
Figure 17C:
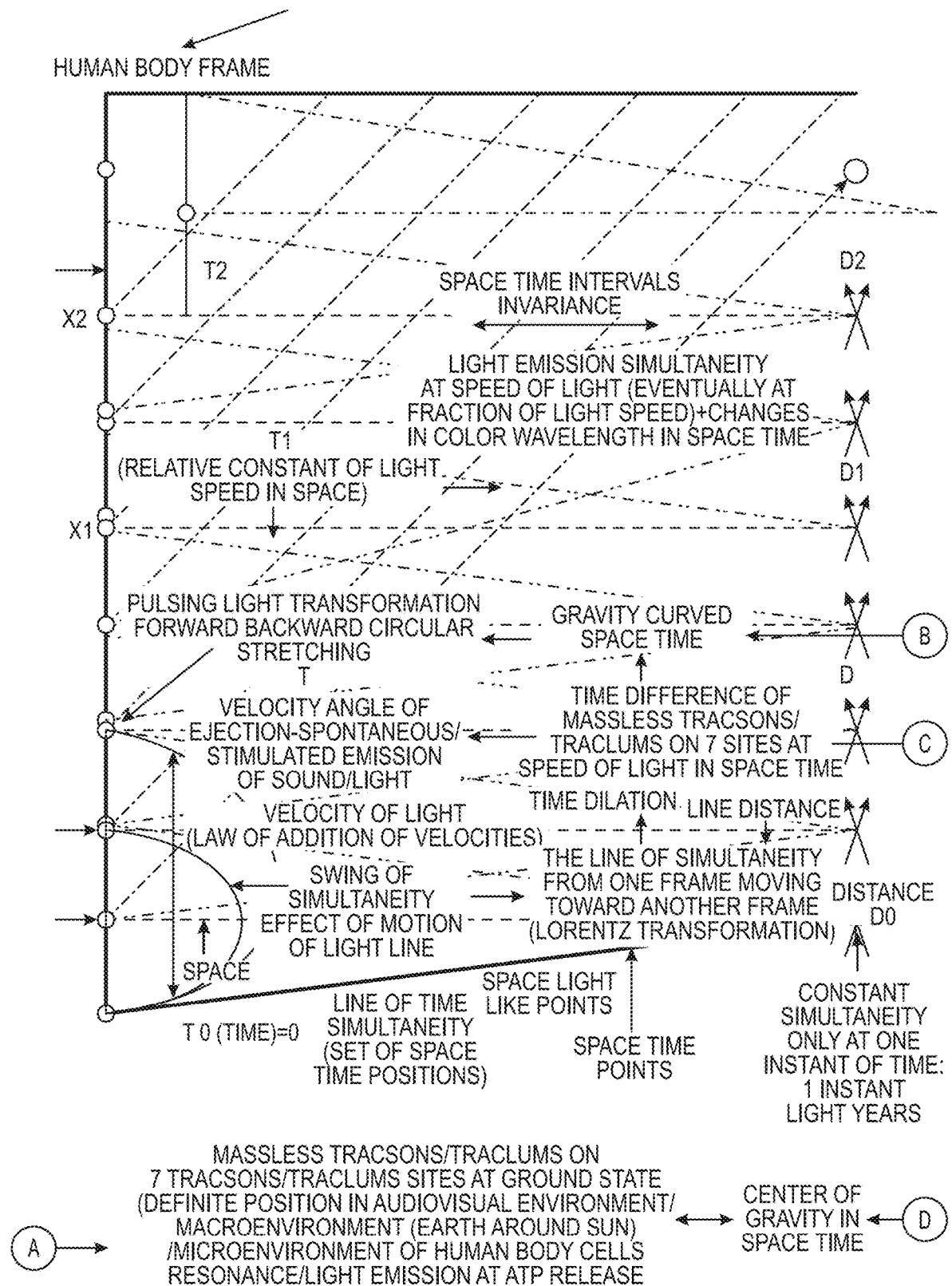
Figure 17D:
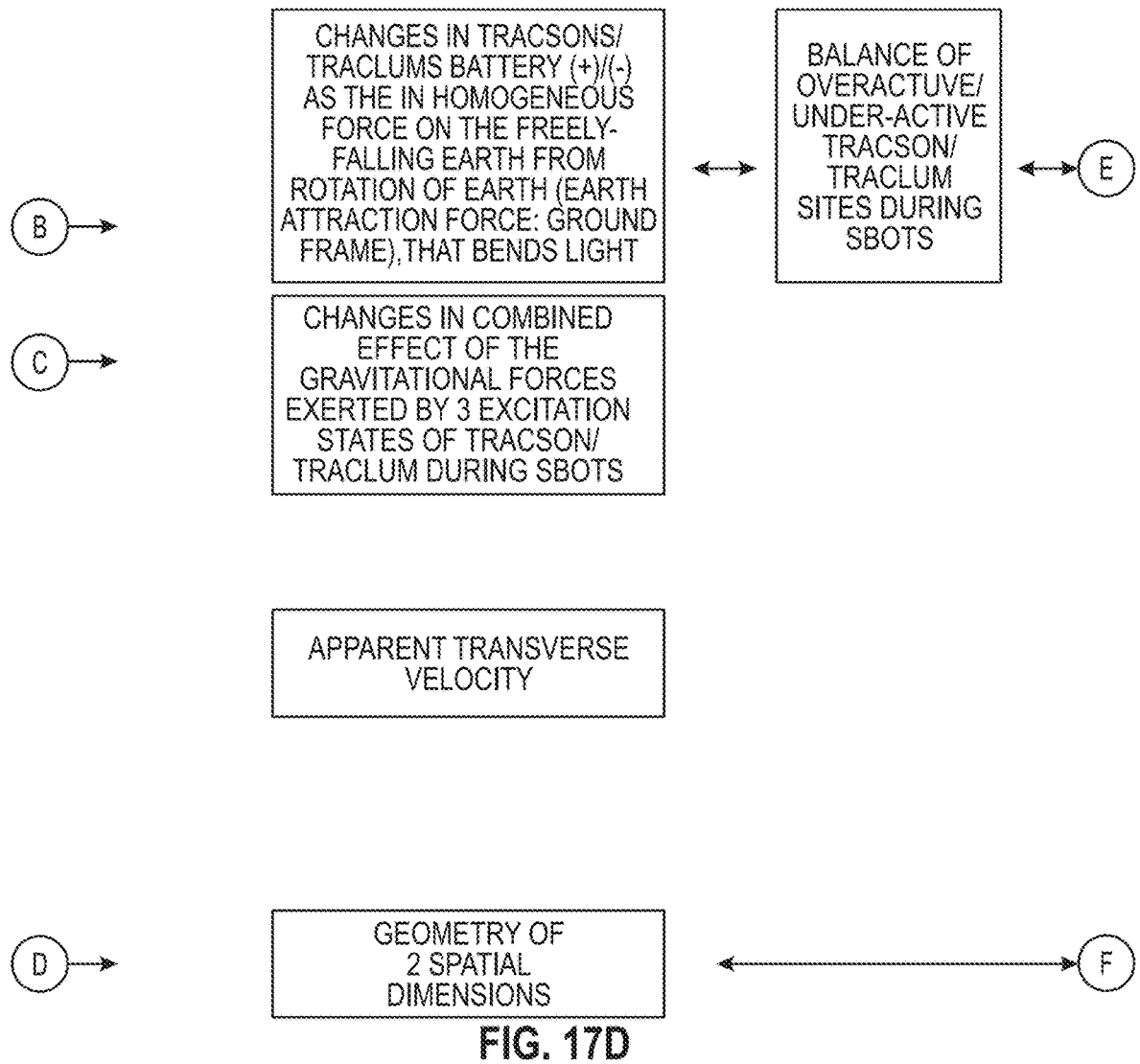
Figure 17E:
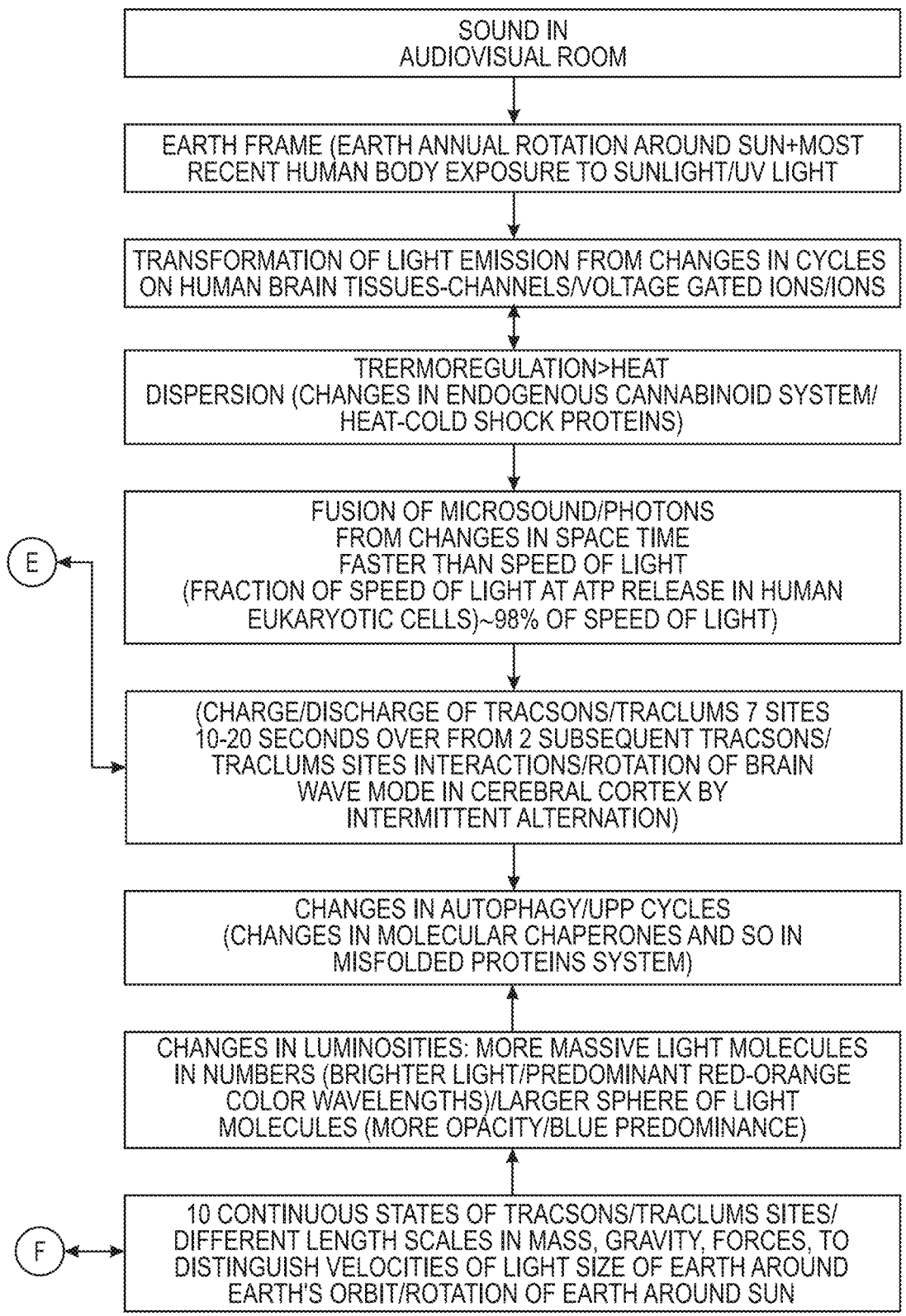
Figure 17F:
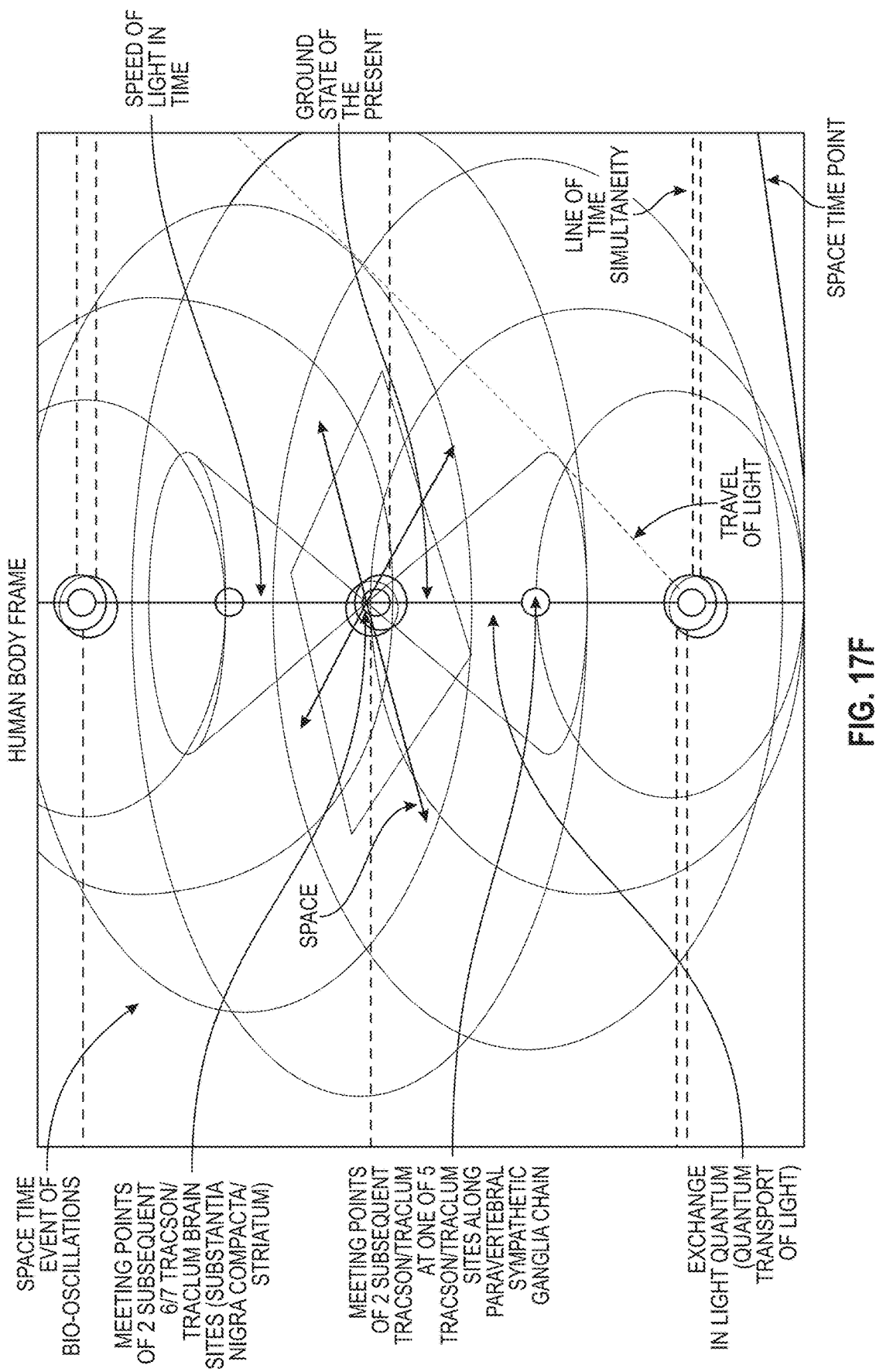
Figure 17G:
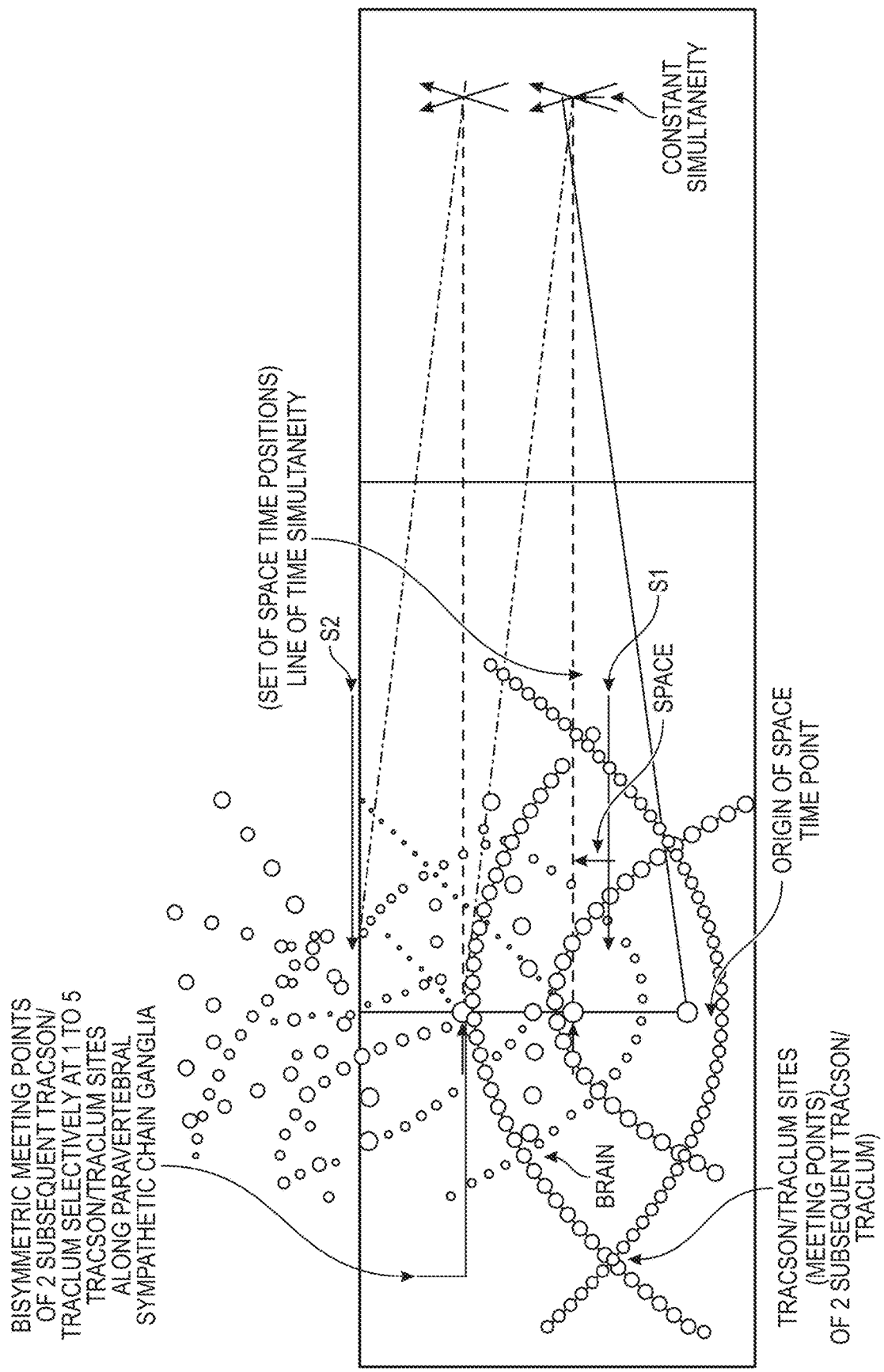
Figure 17H:
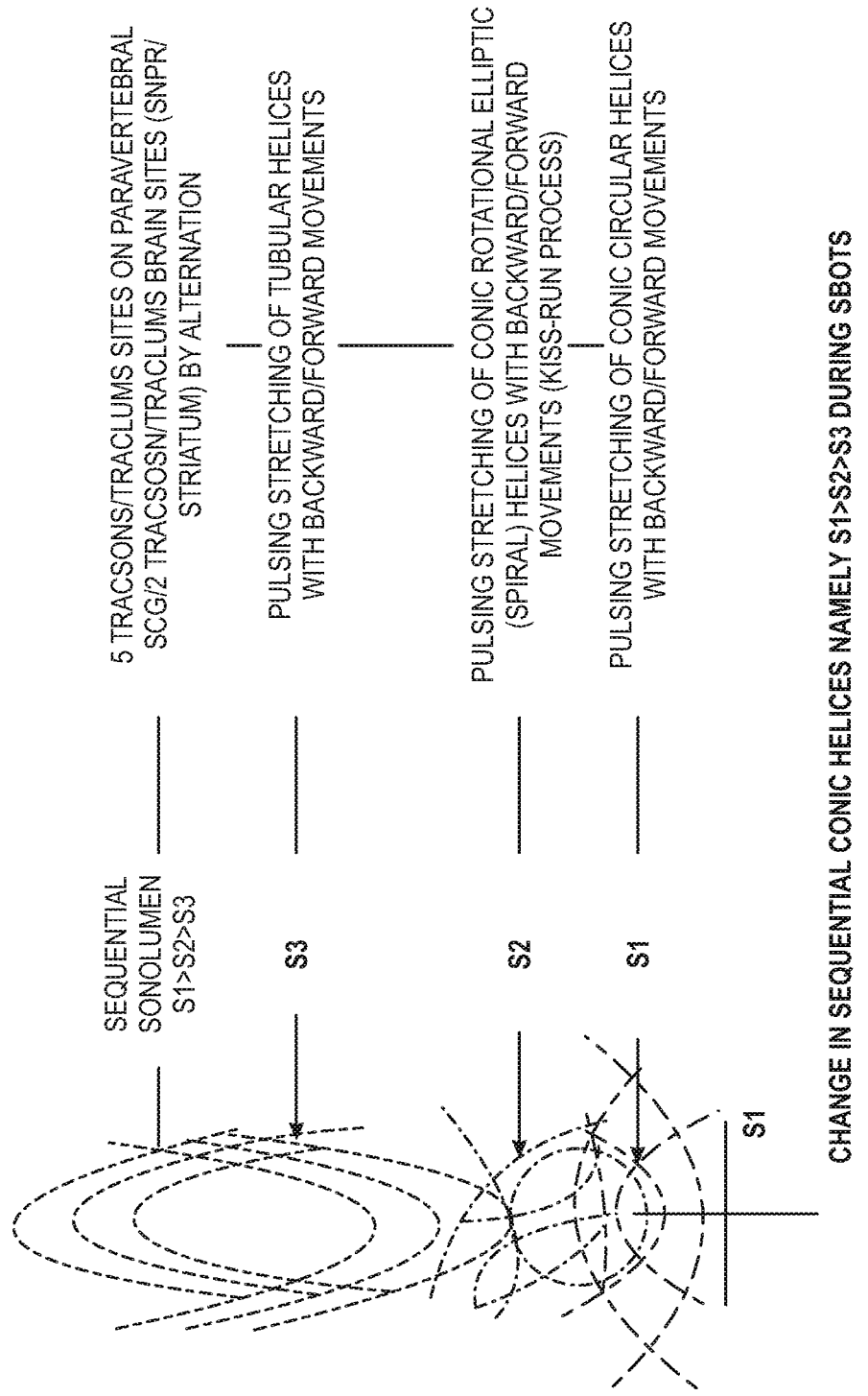
Figure 19A:
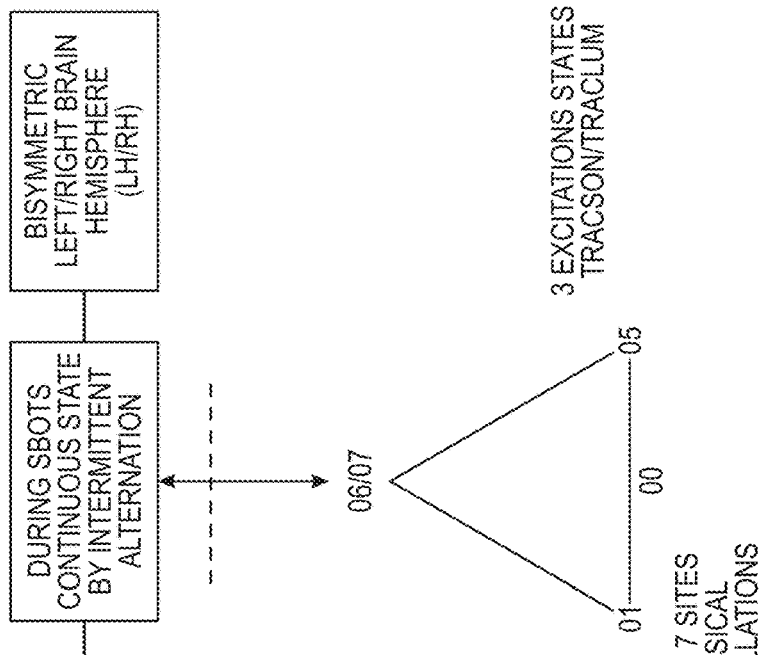
FIGS. 19A and 19B are schematics illustrating Space time event changes of biophysical sonoluminescent oscillations in S1>S2>S3 during SBOTs on a human body.
Figure 19B:
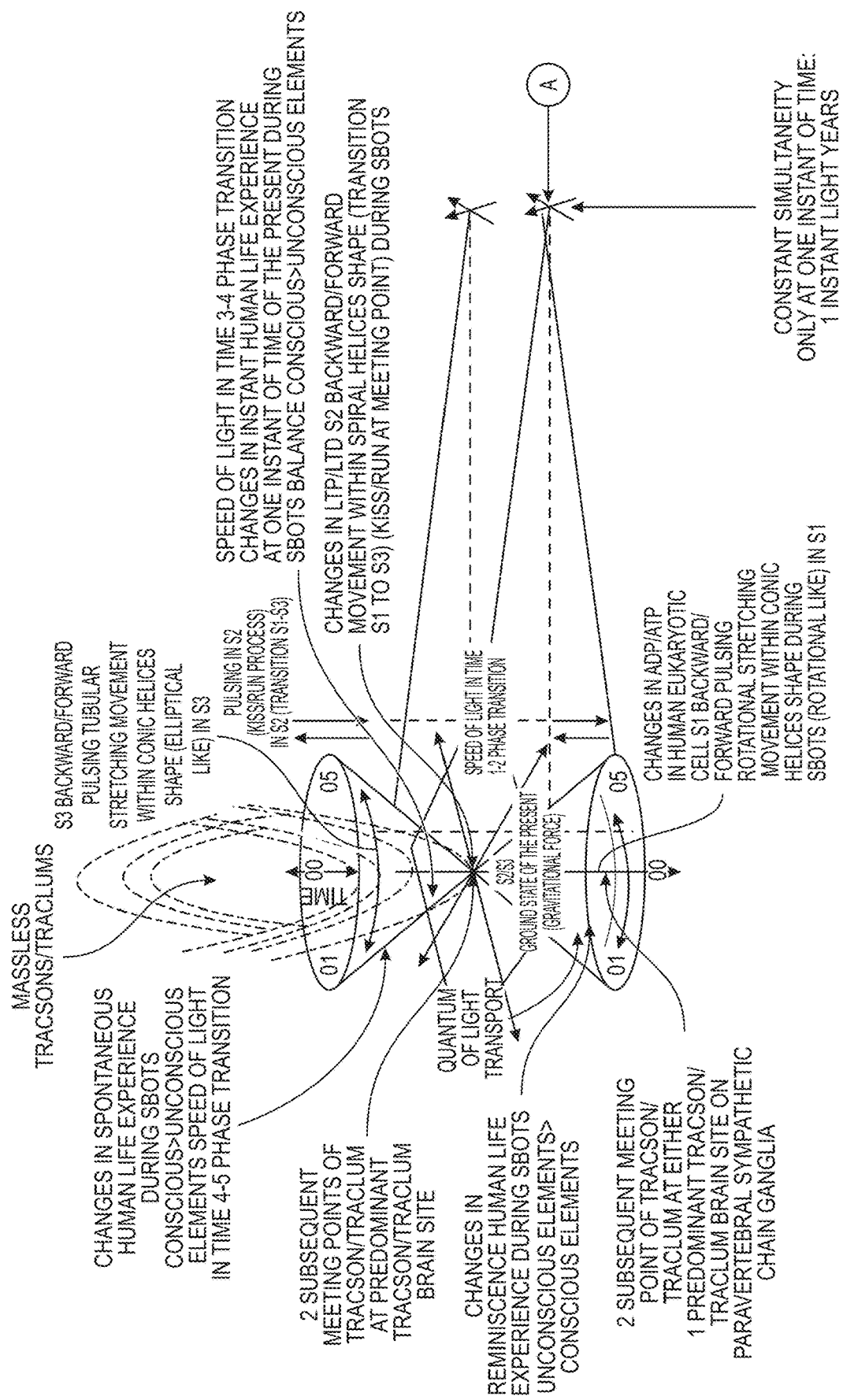
Figure 20:
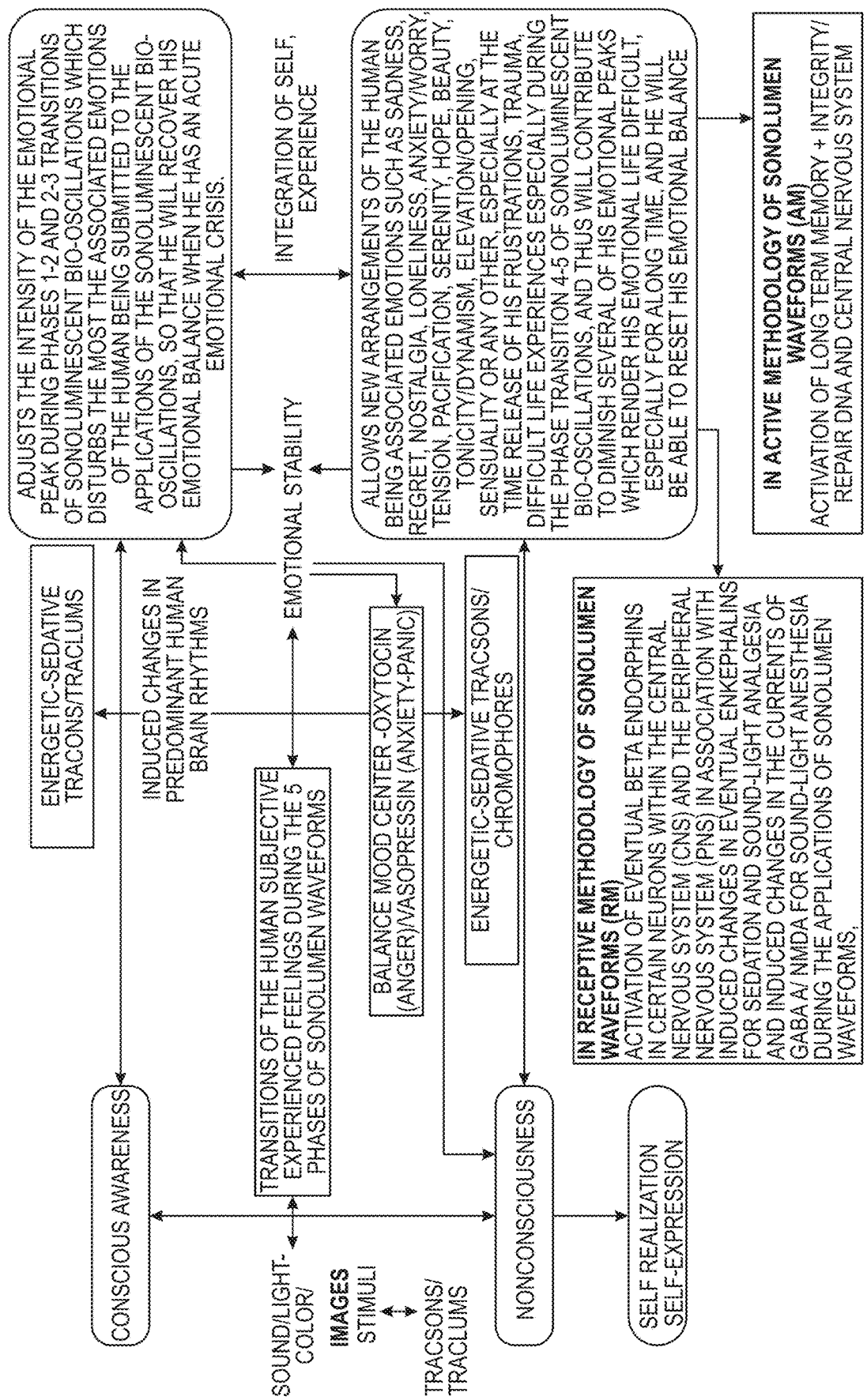
FIG. 20 is a completed flowchart that indicates how the use of the SBOT applications can help achieve an improvement in the following human health conditions involving mood; conscious awareness, non-consciousness, self-realization and expression, analgesia, recovery of emotional stability, and traumatic experience or events, by changes in the transition of the human subjective feelings experienced in the present (during the time of the SBOT applications) and by balancing the mood center in the human amygdala.
Figure 21:
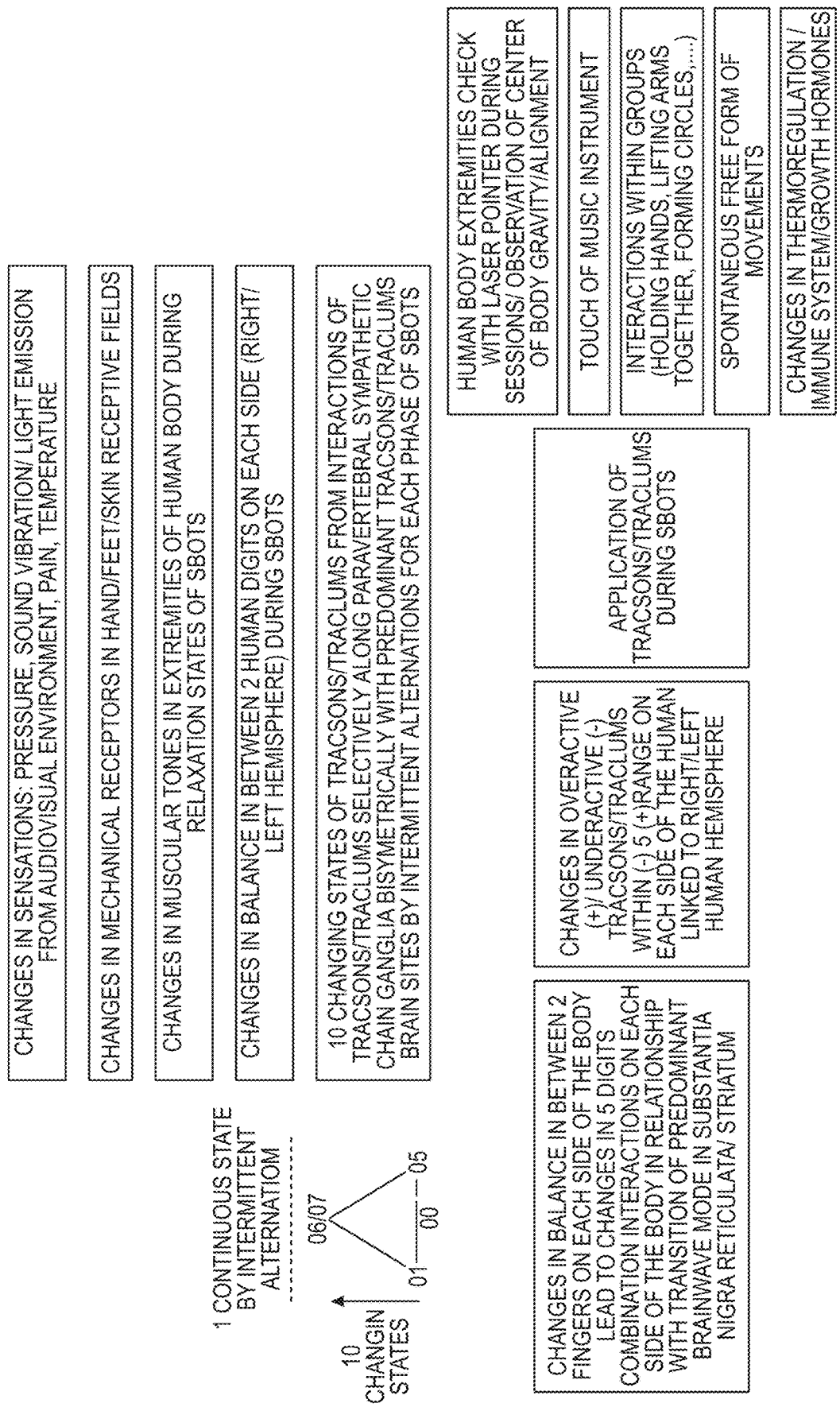
FIG. 21 provides the change/discharge of tracsons/traclums during SBOTs.

(6) FIG. 16 illustrates in detail that the accumulation of tracsons/traclums that appear on 6 specific sites during all 6 of the SBOTs phases is eventually manifested on SBOT pathways, where 5 tracsons/traclums specific sites are localized on paravertebral sympathetic chain ganglia that interact with two dominant brain sites. These include either interaction with the substantia nigra reticulata or on the striatum. This phenomenon is also created by utilizing the alternating intermittent repetitions of the SBOTs. As shown in detailing original FIG. 19, this process leads not only to changes in the participant's/listener's subjective feelings, but also results in emotions that induce progressively deeper states of relaxation. These relaxation states are associated with major interactions that include overall changes in complex networks of neurons during SBOT applications. Appended supporting FIG. 21 and then FIGS. 22A-C and FIGS. 23A-23B illustrate by means of several flowcharts that there are also major changes which occur in the human body regarding physiological, neurochemical, and biochemical responses in body tissues as a result of the use of SBOTS.

Figure 18:
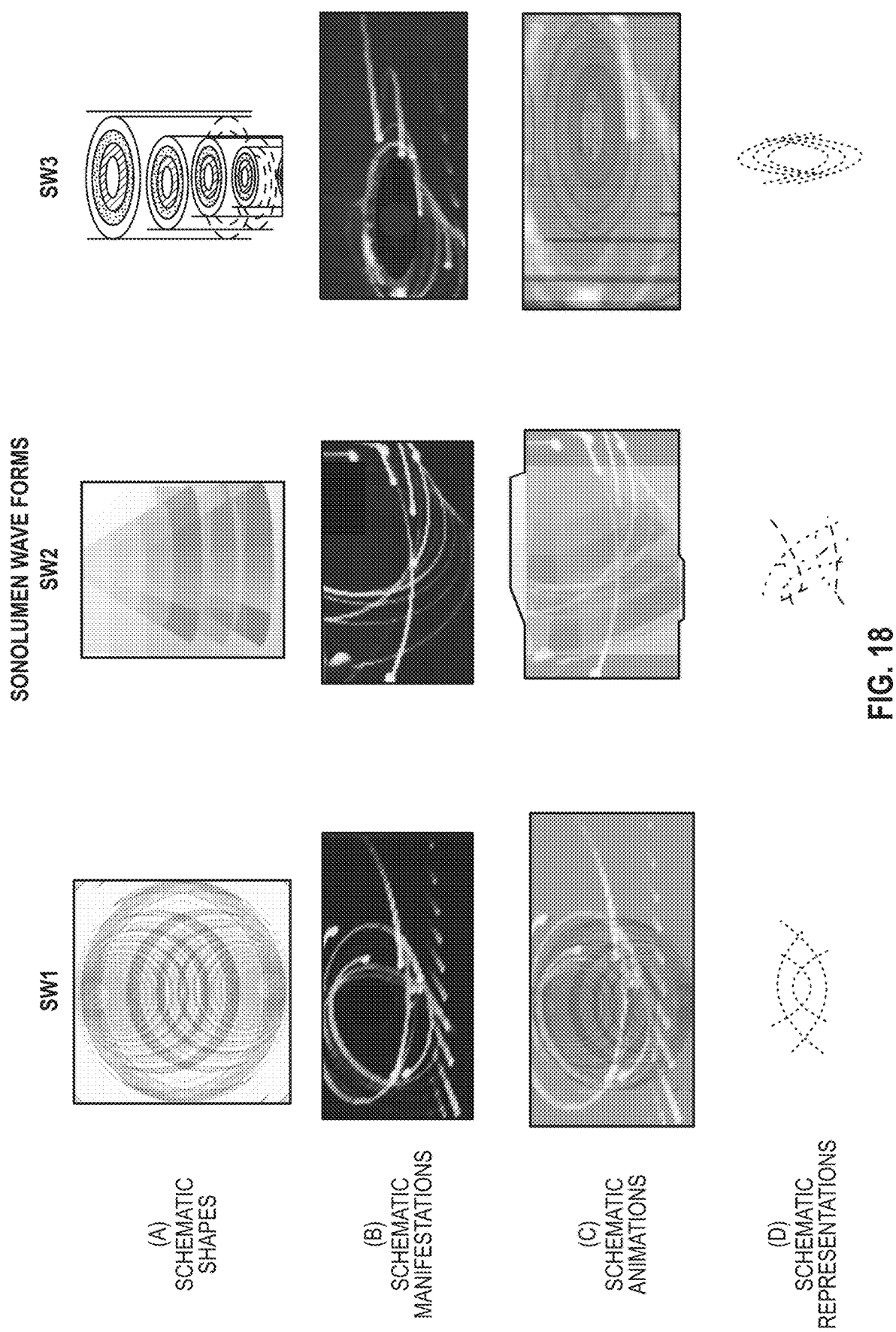
FIG. 18 is a schematic that shows sonolumen wave forms—what they are and how they operate.

Many of the figures provided herein show processes associated with major complex changes in the tissues of the body during SBOTS and in relation with complex changes that cause interactions within TCA (citric acid) cycle, Nitric oxide (NO) formation/decay cycles, DNA and Mitochondrial DNA sequencing, cellular respiration chains, cytoskeleton structures all leading to multiple positive outcomes by the use of SBOTs. These processes are shown sequentially in original FIGS. 22D and 22E, FIGS. 24A and 24B, FIGS. 25A and 25B and FIGS. 26 and 27, as well as in FIG. 28, FIGS. 29A and 29B, FIGS. 30A and 30B and FIG. 47. Different devices can be used to impart SBOTS resulting in major improvements of in overall body health regardless of the causes of ultimate weakness or deficiencies. (8) These tracsons/traclums 6 specific sites that are induced during the SBOTs exist and obey the laws of physics developed by Einstein's theory of relativity as well as Planck's quantum theory by very complex mechanisms that are beyond the scope of this disclosure, as first disclosed in FIGS. 16 and 17A-H and then again in FIG. 18, and further detailed in FIGS. 19A and 19B.

(7) FIGS. 32A through 32D indicate the nature of the interactions of tracsons/traclums within the human body evidenced in a working example indicating what occurs for channel cycle changes on brain tissue. These Figures together with FIG. 7C show the response for dominant brain rhythms in the occipital/frontal cortex and reverse that allows for capture of very low sound frequencies by alternating intermittent repetitions using colored wavelength frequencies. This results in changes in the human body that causes a response to specific auditory/visual stimuli, namely tracsons/traclums produced within the audiovisual room during SBOTs.

Chromophores for Applied Sonoluminescent Biophysical Oscillations

More specifically, FIG. 1 provides a schematic of a process flow for a sonoluminescent biophysical oscillation health improvement methodology (SBOT) sessions for regeneration in any tissue in the human body which depends from different various levels of individual states of health and especially for most debilitating states of health. Initial gathering of information from the participant is conducted in order to determine the individual's medical history in medical facilities and history of light/colors life experiences. The participant is tested to evaluate a liking/disliking of music/light-color/motion pictures and the associated emotions to the light/color in the room and to the most recent exposure of the participant to UV light. Adaptation by the participant to the lightness/darkness of the room is recorded. Personalized sound, music, light, color and/or images (and optional creative activity in conjunction with the above) are generated in response to the prework/test responses of the participant and are (in this instance) introduced to the participant in an audiovisual room where sonoluminescent biophysical oscillations application occurs. Sound/music is introduced via speakers or other sound amplifiers positioned in all four corners of the room and can be used to provide energy or calmness to the participant. Light/color/images are provided via a projector and can be viewed on two separate screens, a split-screen, or single screen.

In the audiovisual room, the participant responds to the diffusion of music and its accentuated tracsons which represent specific auditory stimuli and which are integrated in the music in as shown in FIGS. 4C-4F between 2 notes of the melodic line selected for a specific purpose according to the needs of the participant over a periodic interval of 5 seconds; those tracsons which represent intermediary sound in between 2 notes in the melodic line, target 4 to 10 notes in selected music for SBOTs, and the tracsons change the frequency intervals in between 2 notes in the melodic line, therefore;

(1) there is the integration of 4 to 10 accentuated tracsons 4 to 10 times repetitively in between 2 notes of the melodic line, and also
(2) the induction of each accentuated tracson in between 2 notes lasts 5 seconds, and this process of the integration of 4 to 10 accentuated tracsons in the melodic line occurs over a period of approximately 2 to 3 minutes of the music diffusion which then are separated by 1 minute of regular music diffusion without the integration of accentuated tracsons in the melodic line. There are no changes in any of the interval frequency in between 2 notes in the melodic line during 1 minute period of regular music diffusion. This process continues by intermittent alternation of 2-3 minutes including 4 to 10 accentuated tracsons in the melodic line separated by 1 minute of regular music diffusion without accentuated tracsons in the melodic line during approximately 10-15 minutes of selected music diffusion which represents the time duration for each phase of SBOTs.

At the same time, during the diffusion of music in the audiovisual room, over approximately 10-15 minutes for each phase of SBOTs, the participant responds to light exposure in combination with colors and/or images (as an option because of the eventual projection of a slide show or a short movie as a motion graphic on the wall of the audiovisual room) and its accentuated traclums in the audiovisual room environment. In a manner similar to the use accentuated tracsons there is also integration of accentuated traclums in the transition in between 2 lights/colors and/or 2 images/2 motion graphics (as an option) also over a period of 1-4 seconds, where the traclums target 2 to 8 transitions in-between 2 light/colors and/or 2 images/2 slides/2 motion graphics (as shown in FIG. 4D) over a period of approximately 1-2 minutes followed by a period of 1 minute of regular 2 light/colors/2 mages/2 video clips transition without the integration of accentuated traclums. This process continues during approximately 10-15 minutes for each phase of SBOTs by intermittent alternation with approximately 1-2 minutes of the integration of accentuated traclums in between 2 lights/colors or 2 images/2 video clips (as an option) separated by 1 minute of regular transition in between 2 lights/colors/2 slides/2 video clips without the integration of accentuated traclums in their transitions. Therefore, the participant responds to auditory/visual stimuli and respectively to accentuated tracsons/traclums.

The induction of deep relaxation states using a sound/light rotation system towards the occipital/frontal cortex of the participant is achieved, with the reverse being achieved by intermittent alternation. A higher level of alertness is achieved by the active methodology (AM) than in the receptive methodology (RM).

The provision for participant creative activity (optional) provides a means of self-expression and emotional release and often includes all or some of the following:

(A) Creative sound effect/music by touching musical instruments
(B) Use of intermediary objects (balloons, scarfs, floor, chai, mat, wheelchair, etc.)
(C) Creative painting, drawing, modeling, with clay
(D) Spontaneous free form of movements
(E) Creation of images by the use of smartphone, tablet, camera or other devices These creative activities are influenced by the selection of colors from the visible light spectrum (ROYGBIV), including the selection of sound/music.

The result of the SBOT creative activity is the regulation of growth factors (GFs) and growth hormones (GHs) and improvements in mental abilities, motor skills, improvement of the five senses, sleep, aging, memory, cognition, communication, social skills, increased performance, relaxation, emotional stability, better achievement, recovery after surgery, healing after trauma/accident, and behavior.

The results of the SBOT sound/light exposure often includes changes in the oxytocin and vasopressin centers, DNA and CNS repair, and retinol/neuromelanine regeneration, resulting in improvements in mental abilities, motor skills, improvement of the five senses, sleep, aging, memory, cognition, communication, social skills, increased performance, relaxation, emotional stability, better achievement, recovery after surgery, healing after trauma/accident, and behavior.

As shown in FIG. 3, traclums are specific visual stimuli which represent intermediary light-colors/image(s) transitions existing between two light-colors coming from (usually) different color projectors-lighting and/or optionally two images from the projection of a slide show on the wall of the audiovisual room during the application of sonoluminescent biophysical oscillations on the human body. FIG. 2 indicates that these specific visual stimuli have their origins beginning with a memory storage that utilizes a library of photo-image-video clip-slide show-visual effects saved on (often an external) hard drive (or other computer memory storage devices). The selection of light colors-photos-images-video clips- and the associated slide show for each phase of the sonoluminescent biophysical oscillations is accomplished by the use of different photo-image-video editing programs including software programs such as Adobe Premiere®, Final Cut Pro®, Motion®, etc. This allows for the manual integration of the chromophores in between two light-colors and eventually two images that transition leading to specifically induced light-color visual stimuli from chromophores in the audiovisual room by intermittent repetitive applications. These applications induce human eye jump (or twitch of an eye) within 1-4 seconds over 2 to 8 two light-colors and eventually the two images transition at each induction of chromophore stimulus over a period of ~1-2 minutes for each phase of the sonoluminescent biophysical oscillations. These sonoluminescent biophysical oscillation sessions normally last approximately ten minutes.

The traclums also interact by intermittent repetitive applications with tracsons. The tracsons are specific sound stimuli coming from diffusion of music that is heard in the audiovisual room by the participant. The music is delivered either by the use of speakers which render the methodology of the sonoluminescent biophysical oscillations on the human body active, or the use of headphones connected to the human ear by intermittent applications from the left ear to the right ear in a clock wise manner. This methodology (the use of traclums together with tracsons) renders the applied methodology of the sonoluminescent biophysical oscillations on the human body into a receptive mode. FIG. 2 illustrates how music is provided from retrieval of the storage of a music-sound effects library also saved on an external hard drive (or other appropriate computer memory storage devices). The selection of the music composition for each phase of the sonoluminescent biophysical oscillations is accomplished by the use of different music editing programs such as Logic Pro®, Adobe Audition®, etc. Implementation of these tools allows for the manual integration of specific auditory stimuli (such as tracsons) in between two fundamental musical notes within 3-5 seconds and over 4-10 notes (in between 4-10 fundamental notes) that exist in the selected musical composition. The selected musical composition during induction of the tracson leads to specific induced auditory stimuli from tracsons in the audiovisual room. These auditory stimuli are provided by intermittent repetitive applications (repetitive applications) over ~2-3 minutes that subsequently induce human body sound resonance perception in a similar manner to that of the human body's perception of touch from the stimulation of the skin (touch) in between two mechanical stimuli of the skin.

In lieu of, or another method that provides the same or similar stimulation can be provided (in association with the tracsons/traclums stimuli during the applications of the sonoluminescent biophysical oscillations on the human body) including sound-light massage, for example, for better management of pain during labor.

Human massage provides different health improvement values for different types of skin receptors (as shown in appended supporting FIGS. 2A-2C. 3A, 3B, 4A and parts of FIG. 5A) and provides different induced changes to the human state of health and various levels of debilitation or degeneration in response to induced changes in the sensations of cold and warmth experienced during the applied sonoluminescent biophysical oscillations on the human body.

There are changes in thermo-receptors respectively, first found in the palms of human hands and especially from changes in the joints of fingers with cold receptors, followed by the thermo-receptors found in the feet in association with changes in cold receptors found in the aponeurosis of peripheral nerve terminals in response to changes of thermo-receptors in the human oral cavity and also from changes of cold receptors on human lip and male/female organs resulting from changes in predominant brainwave mode in occipital cortex versus frontal cortex and reverse during sound/light massage also called tracsons/traclums massage which modify cold receptors in the conjunctiva in relationship to activation of peripheral cold receptors, and there are changes in the neuromodulation by the use of human massage during SBOTs.

Figure 22A:
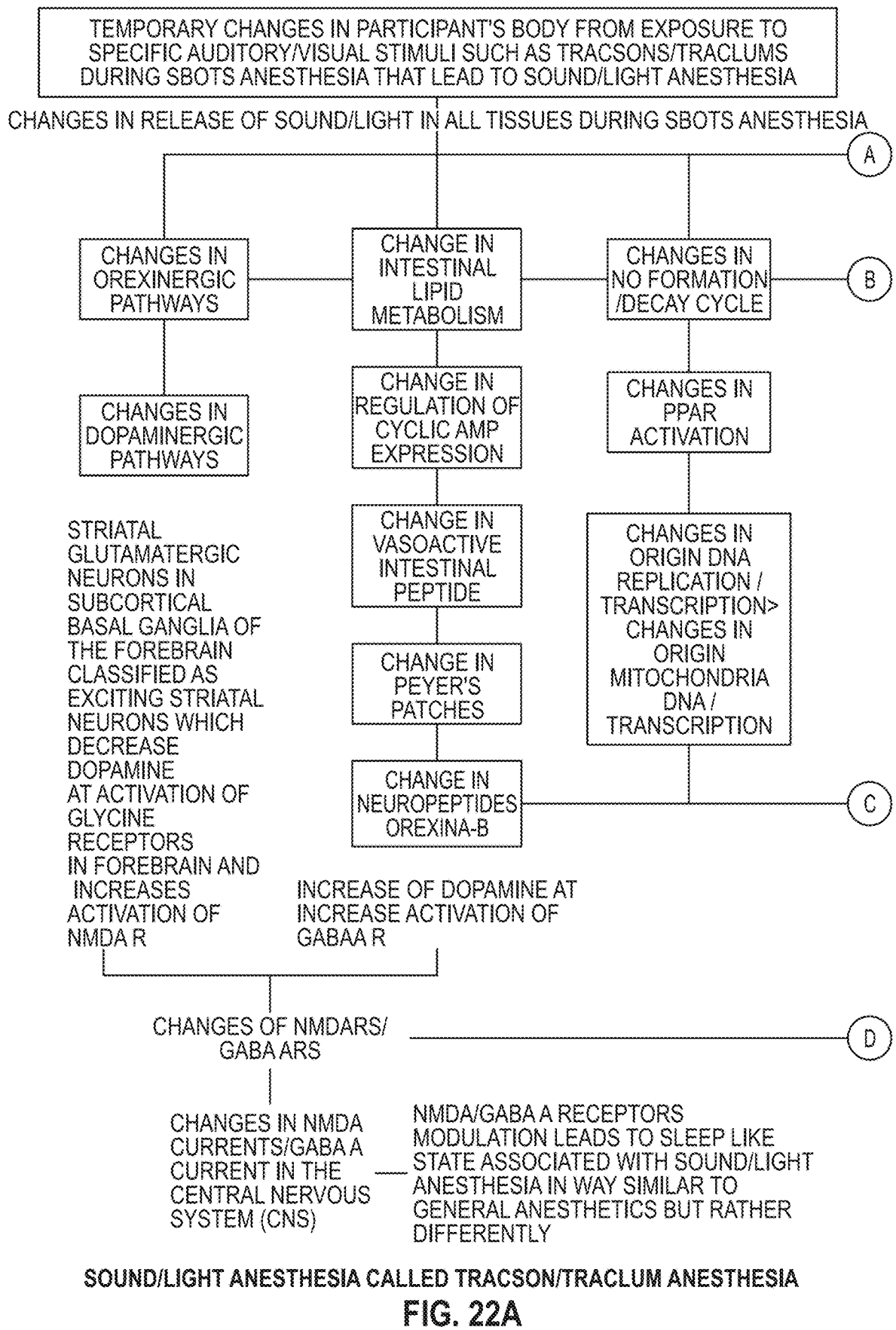
FIG. 22A-C provides sound/light anesthesia, referred to as tracson/traclum anesthesia.
Figure 22B:
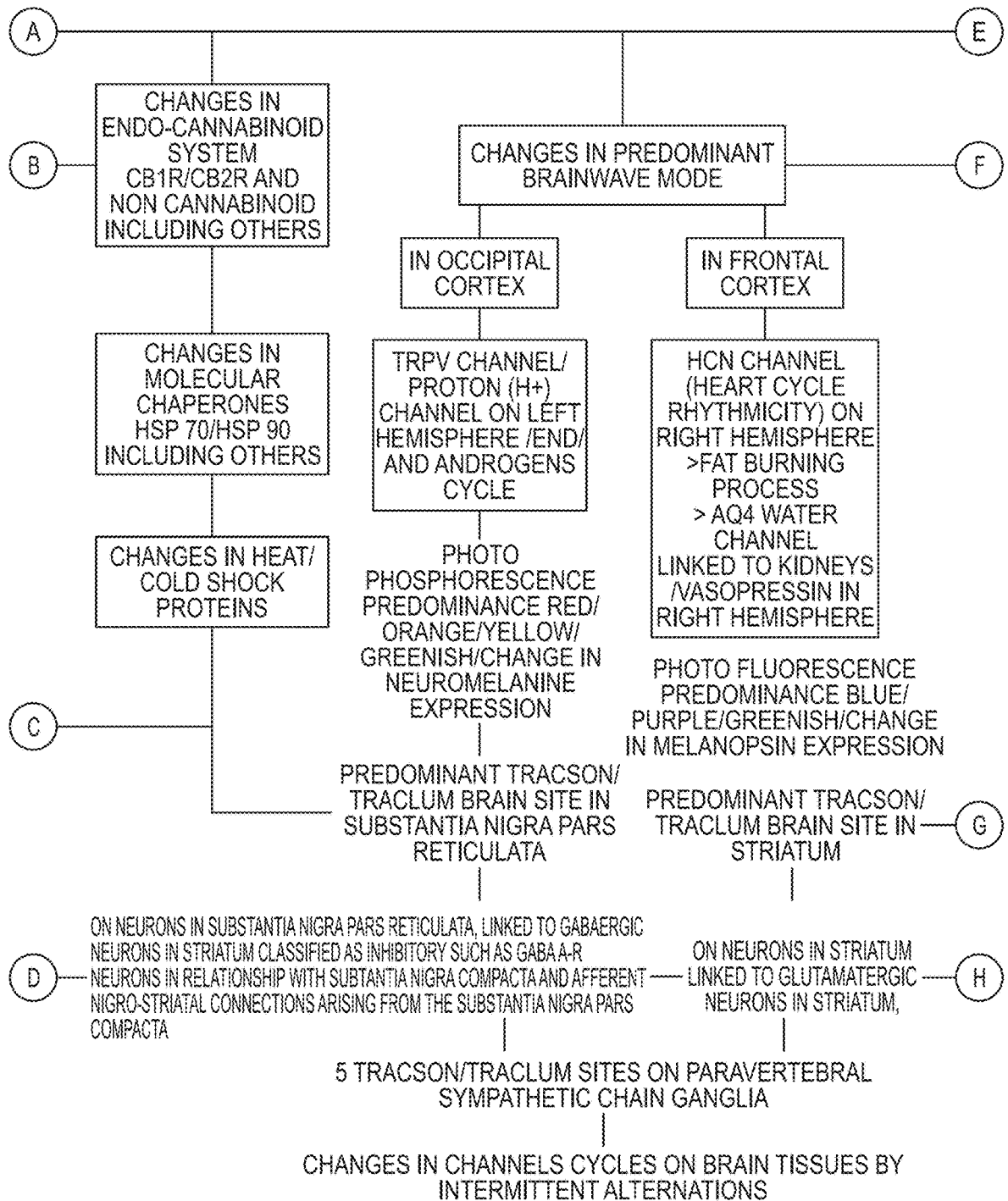
Figure 22C:
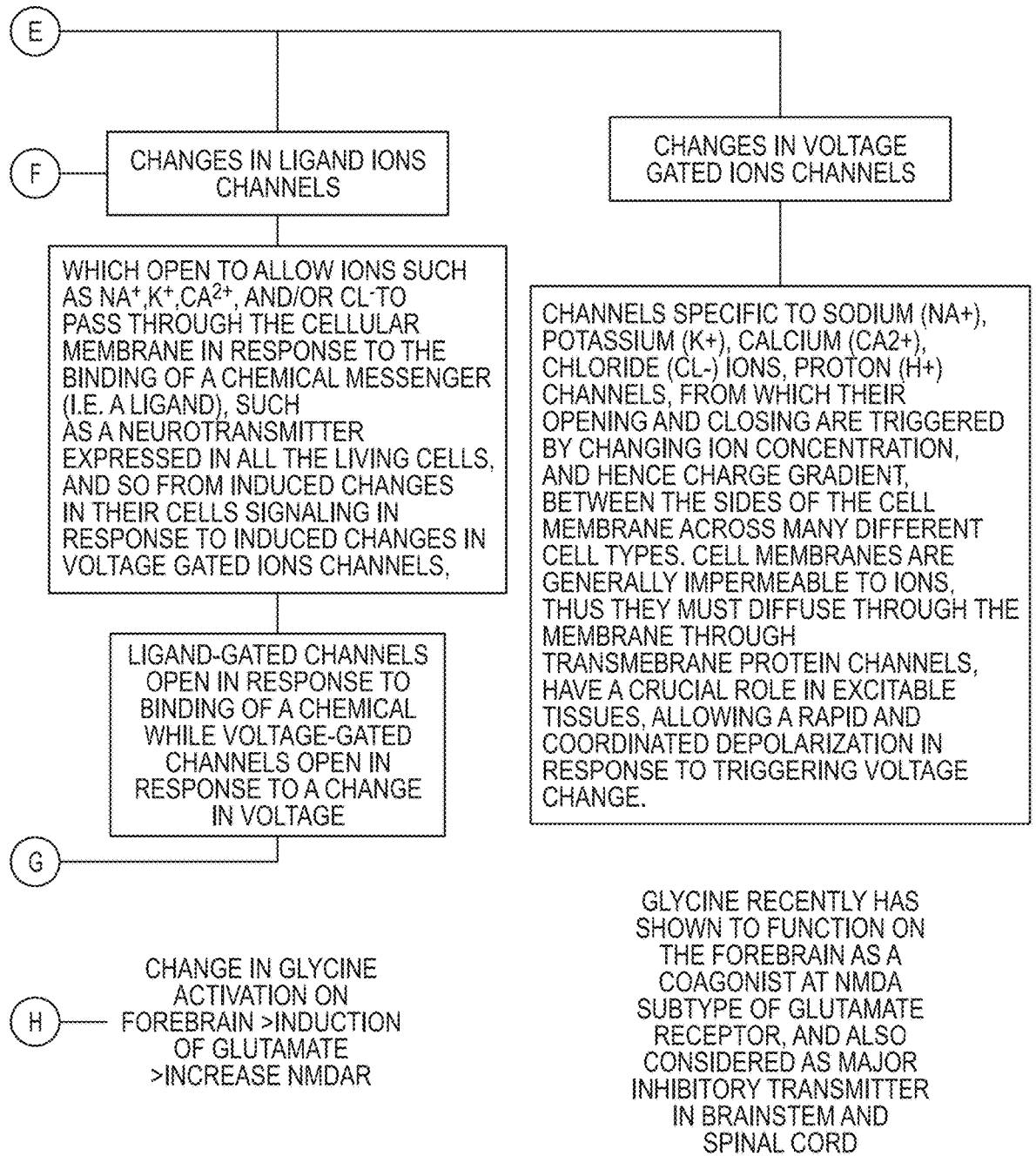
Figure 22D:
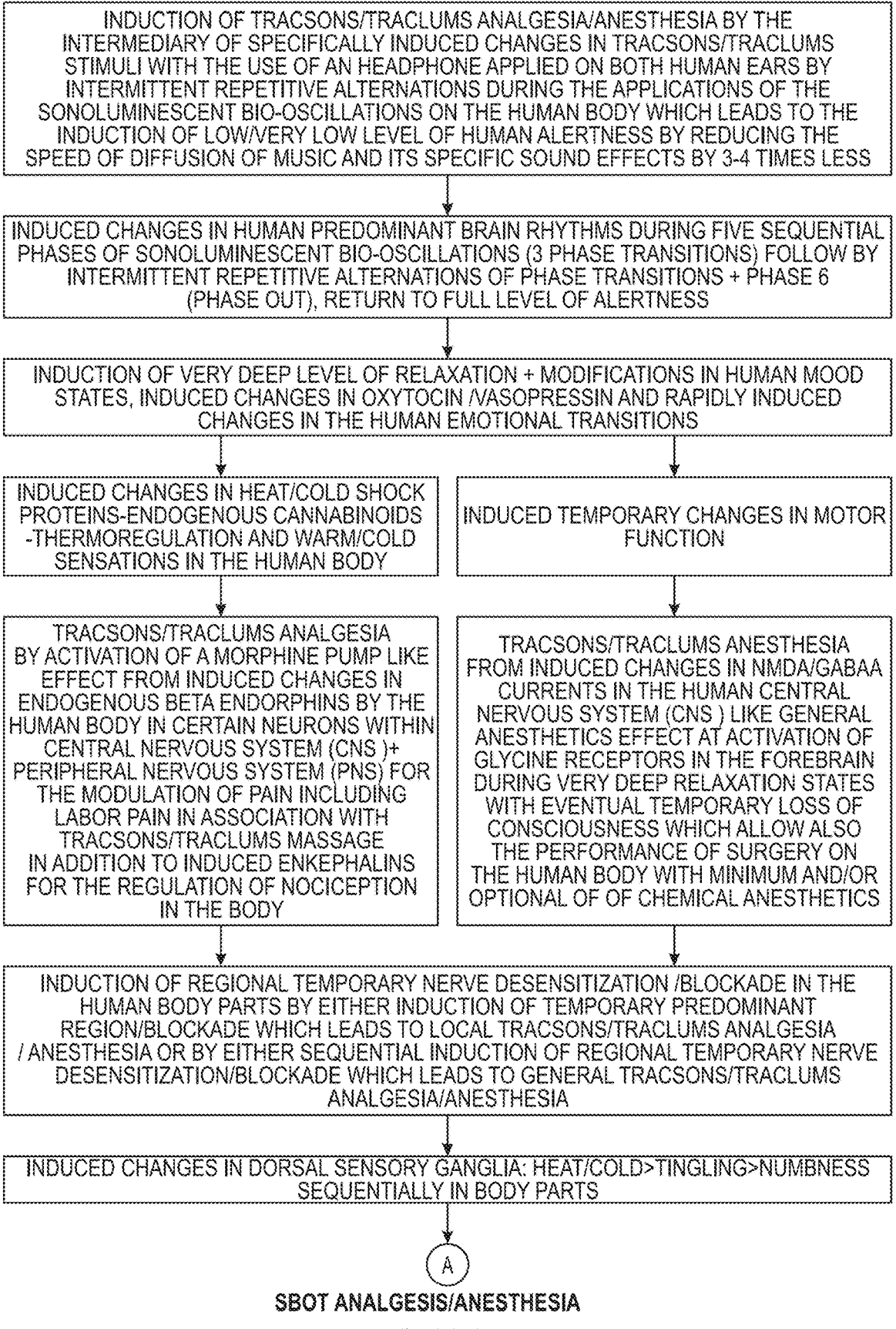
FIG. 22D is an initial flow chart illustrating how the use of tracsons/traclums provide anesthesia/analgesia in individuals undergoing the treatment necessary for this positive outcome using SBOTs.
Figure 22E:
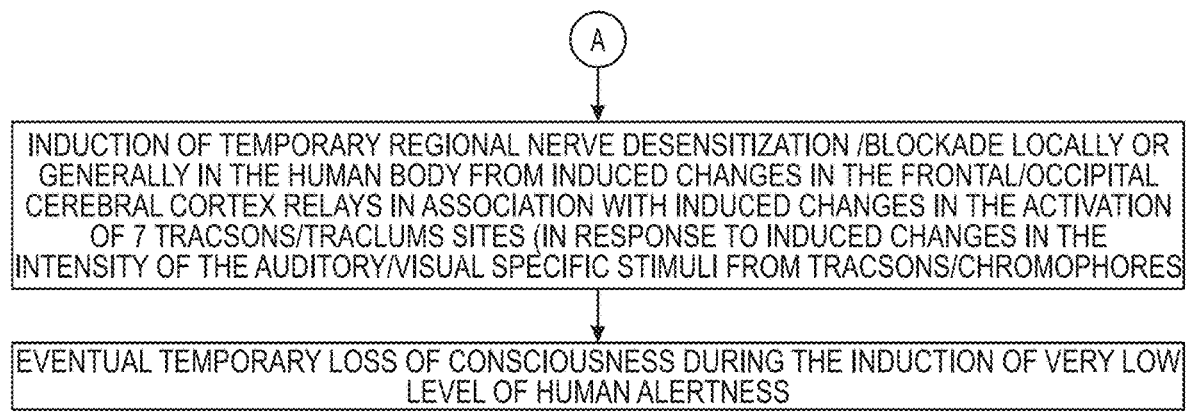
FIG. 22E completes the flow chart of FIG. 22D and indicates how the use of the 7 tracsons/traclums sites are associated with the outcomes of temporary nerve desensitization and temporary loss of consciousness as needed by use of the SBOTs.
Figure 23A:
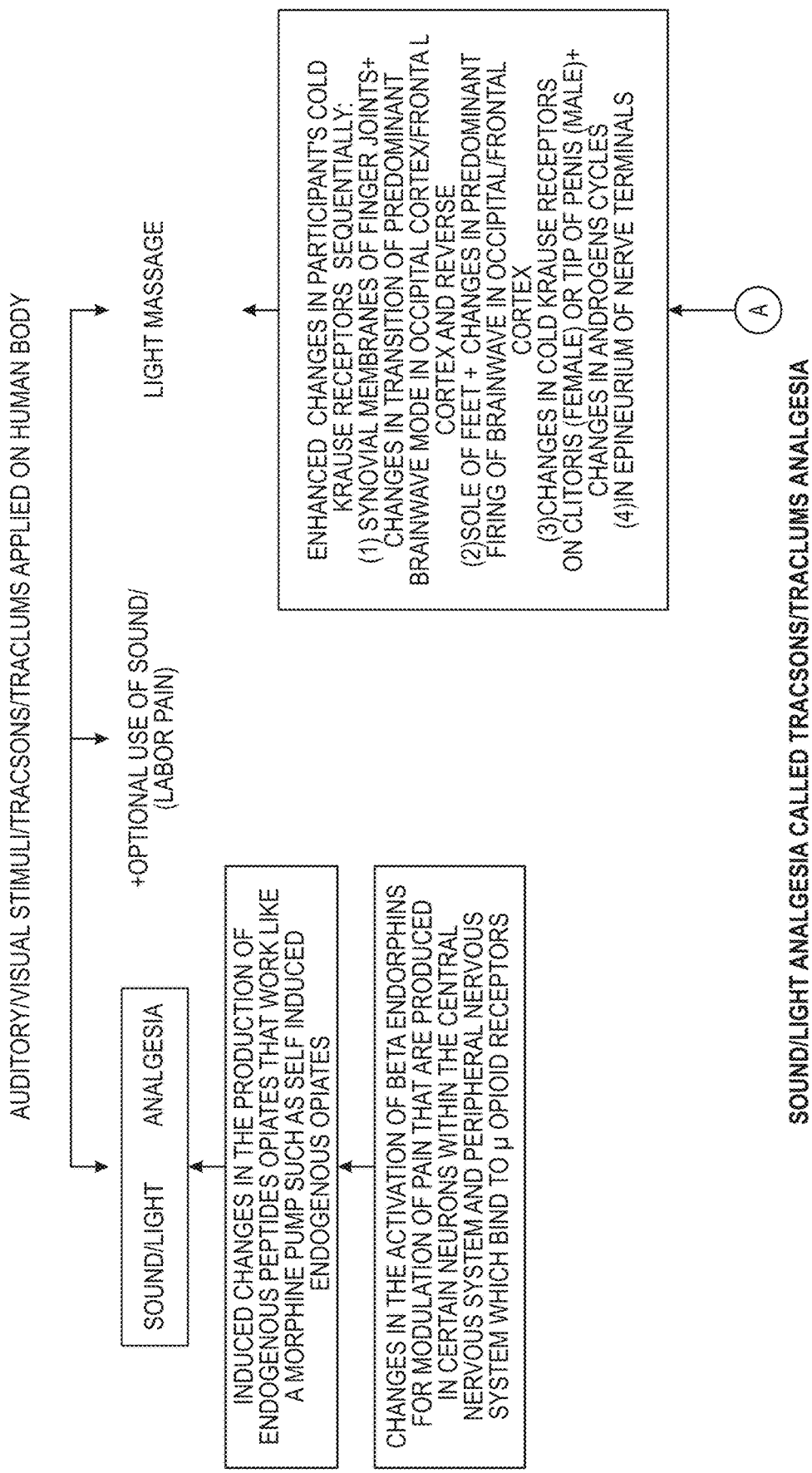
Figure 25A:
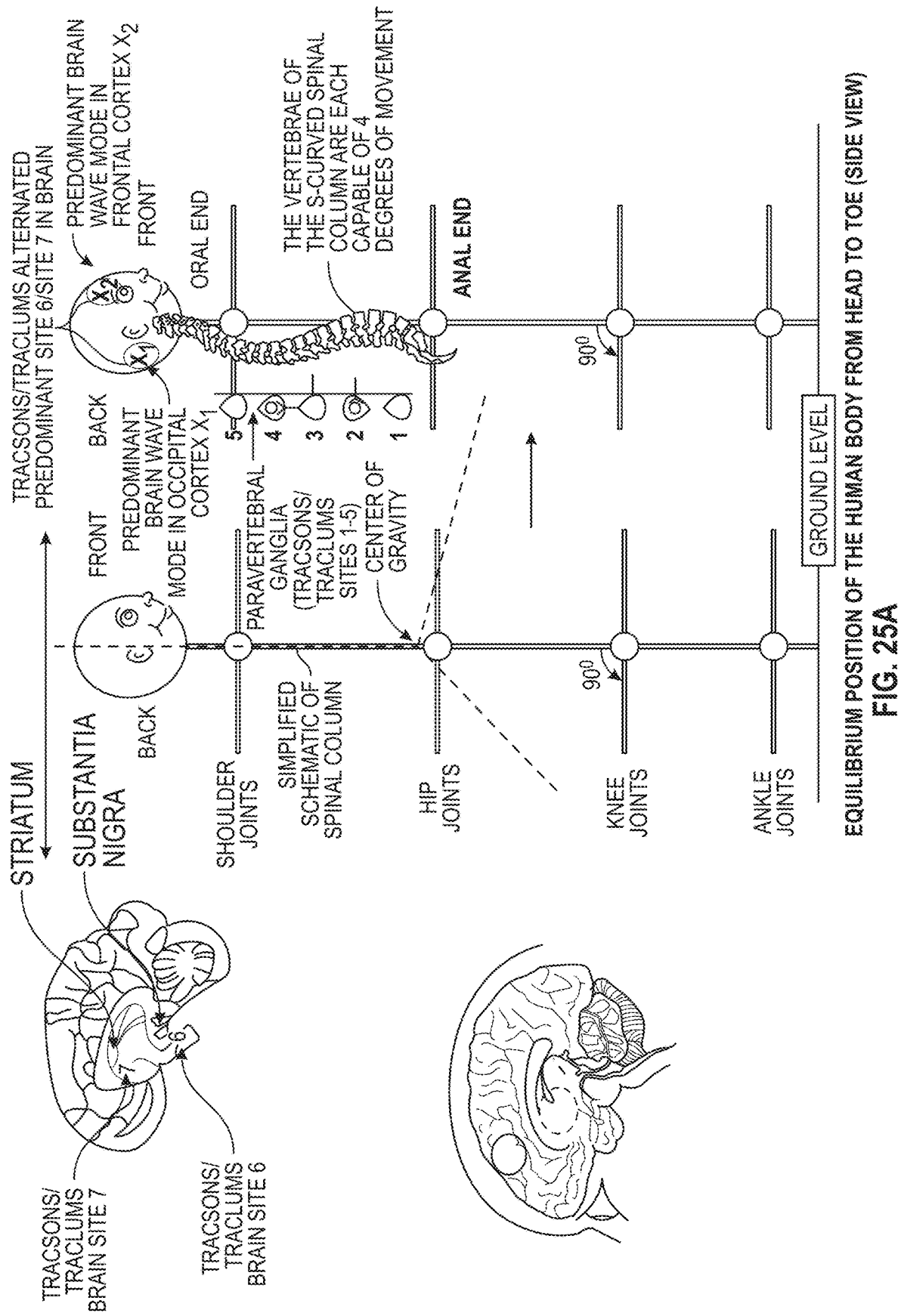
FIG. 25A is a schematic that shows how different sites and the human body may be in an equilibrium imbalance which may require change by the use of tracsons/traclums to achieve tracson/traclum excitation states and induce changes in the human state of health using the SBOTs.
Figure 25B:
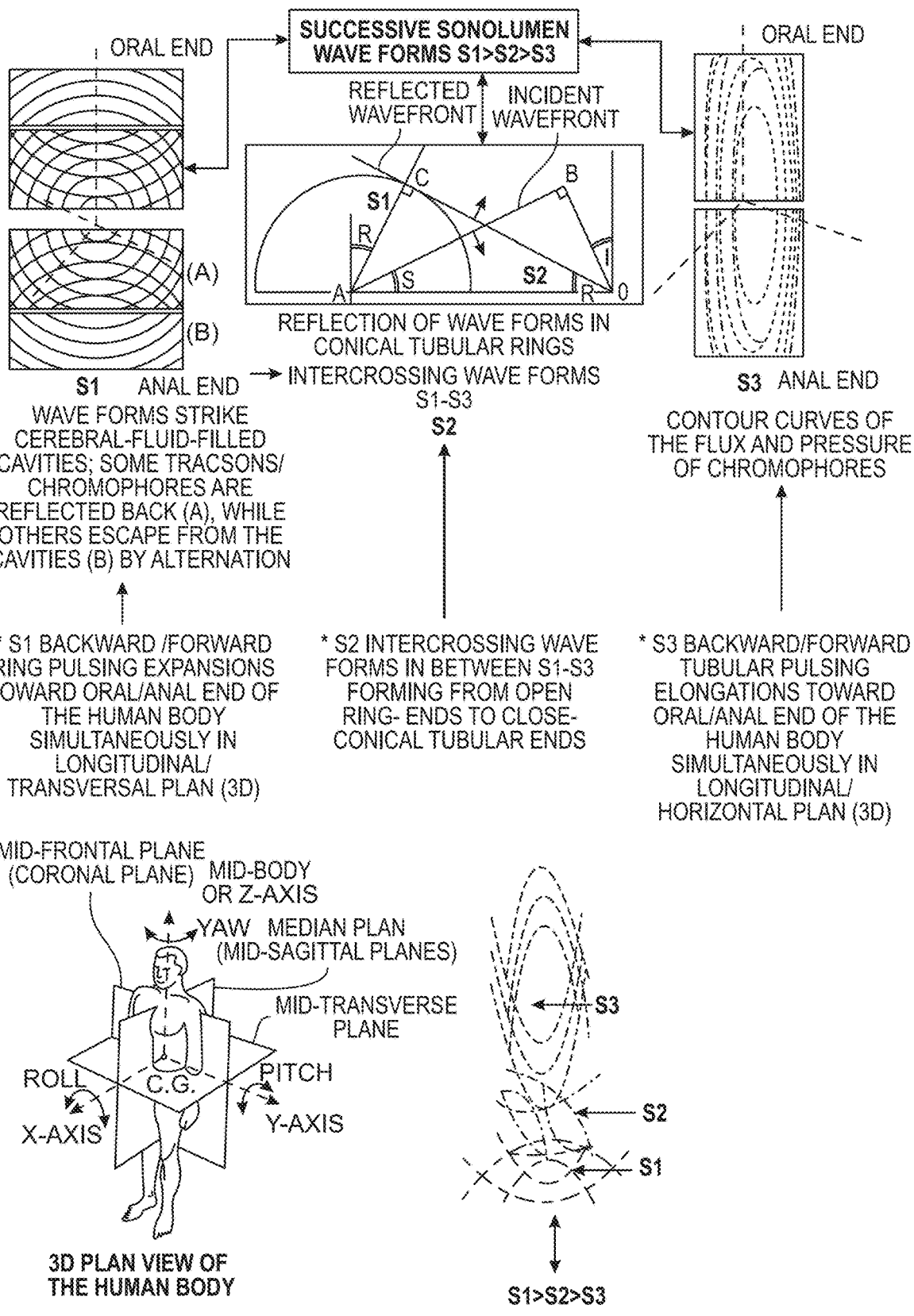
FIG. 25B is a schematic representation of how successive sonoluminescent wave forms exist and are utilized for various changes in the human states of health.
Figure 26:
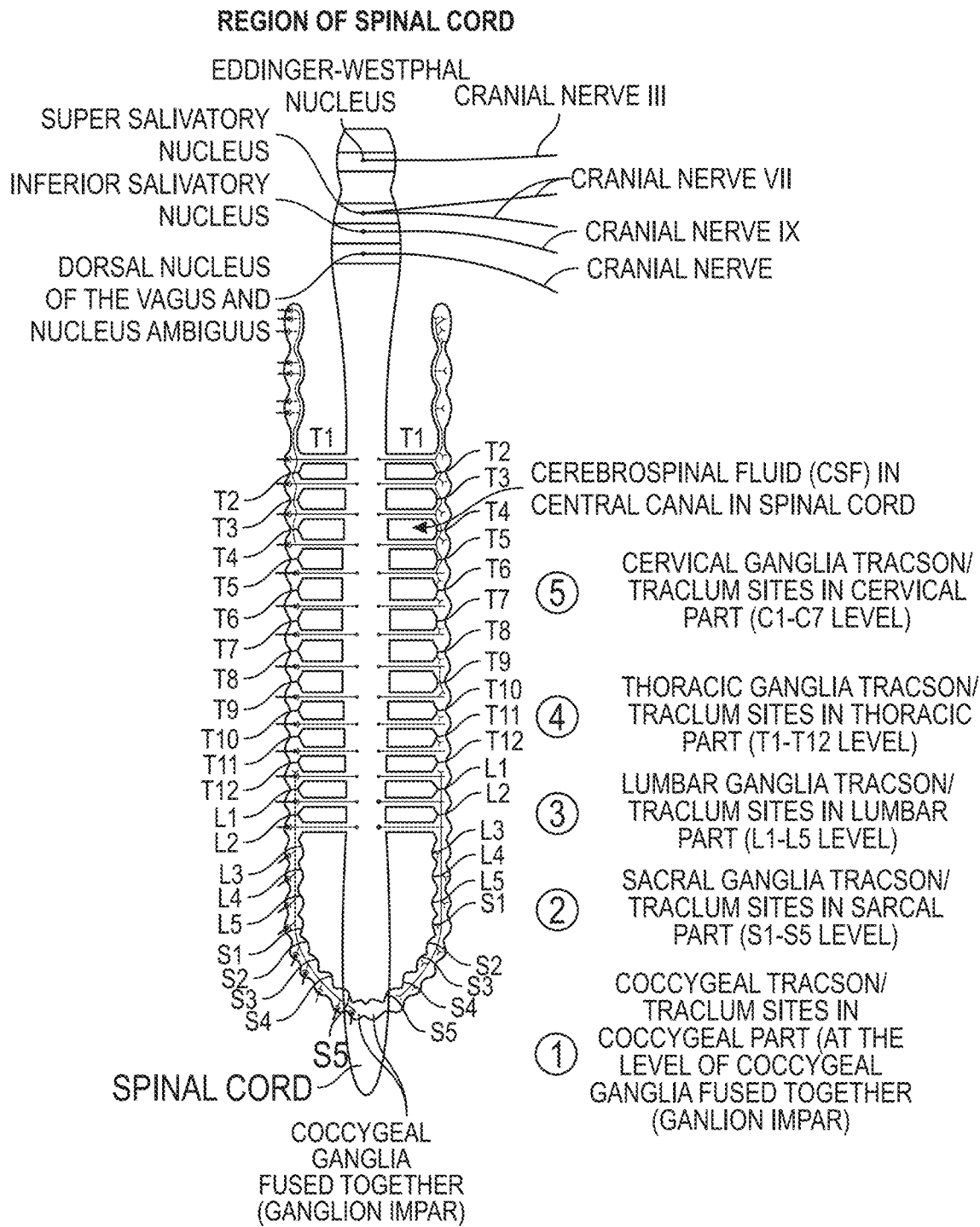
FIG. 26 is a schematic representation regarding the use of 5 tracsons/traclums sites which interact with one dominant brain site by alternating intermittent repetitions and which are utilized to regenerate the human spinal system using SBOTs.
Figure 31:
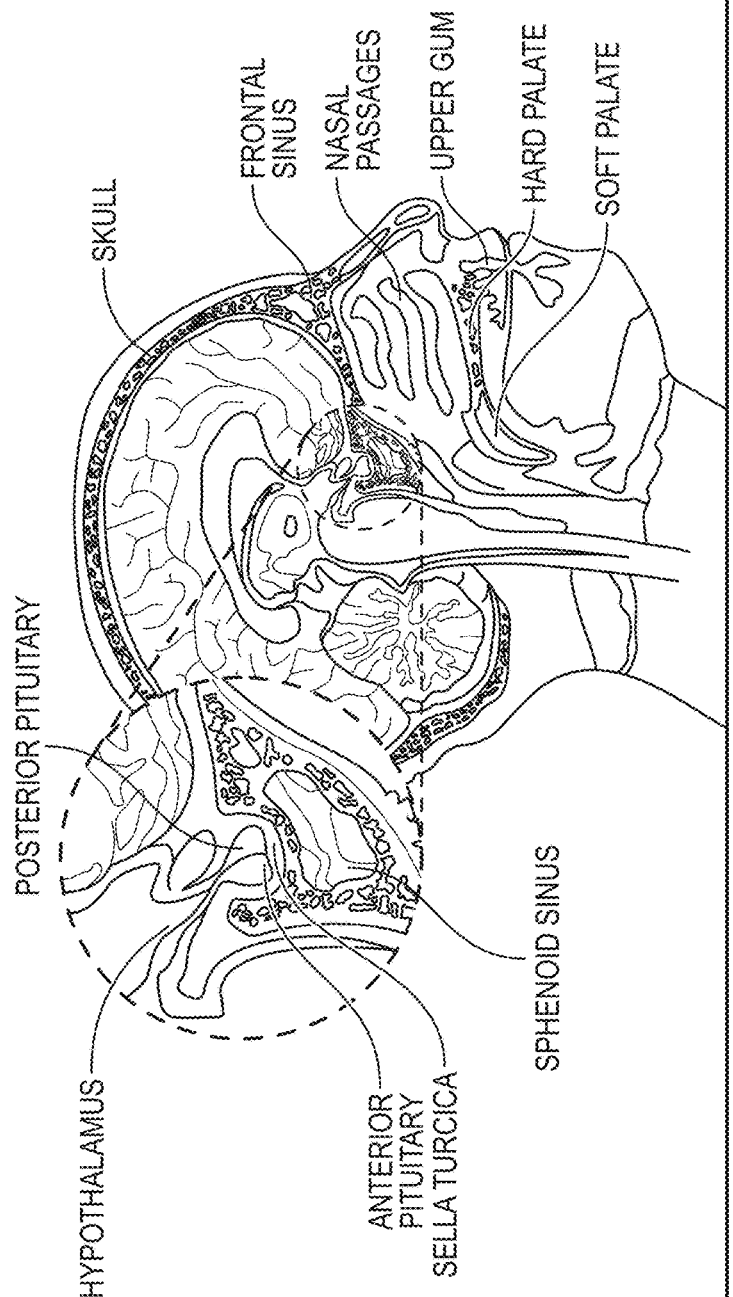
FIG. 31 describes SBOTs and resulting tissue and organ regeneration.

As shown in FIG. 4, the reception of the sonoluminescent biophysical oscillations provide for induction of very deep relaxation states that allow the induction of sound-light by the activation of a morphine pump-like effects from induced changes in endogenous beta endorphins by the human body in certain neurons within the Central Nervous System (CNS) and the Peripheral Nervous System (PNS). The central nervous system or the CNS contains the brain and the spinal cord. The peripheral nervous system or PNS contains the nerves, which leave the brain and the spinal cord and travel to certain areas of the body. These changes in endogenois beta endorphins allow for the modulation of pain including labor pain in association with sound-light massage. As shown in FIGS. 22A-C, in addition this modulation includes induced enkephalins (peptides related to endorphins, with similar physiological effects) for the regulation of nociception (the nervous systems response to certain harmful or potentially harmful stimuli) by body/sound-light anesthesia which correspond to a general anesthetic effect from induced changes in the NMDA/GABAA in the human central nervous system (CNS) via activation of glycine receptors in the forebrain during very deep relaxation states with eventual temporary reduced level of consciousness.

It is known that the main ionotropic receptors (GABAA, NMDA and AMPA) display a sequential participation in neuronal excitation in the neonatal hippocampus. Here, γ-aminobutyric acid (GABA), the principal inhibitory transmitter in the adult CNS, acts as an excitatory transmitter in early postnatal stage. Glutamatergic synaptic transmission is first purely N-methyl-D-aspartate (NMDA)-receptor based and lacks functional α-amino-3-hydroxy-5-methyl-4-isoxazolepropionic acid (AMPA) receptors. Therefore, initially glutamatergic synapses are 'silent' at resting membrane potential, NMDA channels being blocked by Mg2+. However, when GABA and glutamatergic synapses are coactivated during the physiological patterns of activity, GABA A receptors, which are a part of a ligand-gated ion channel complex, can facilitate the activation of NMDA receptors, playing the role conferred to AMPA receptors later on in development.

This novel technique provides for the performance of surgery on the human body with minimum and/or optional use of chemical anesthetics. In addition, the techniques described herein include other positive human health improvement outcomes including better sleep, better learning abilities, and improved relaxation. It is also clear that the active methodology of the use of sonoluminescent biophysical oscillations induces less deep states of relaxation resulting in more alertness than the receptive methodology. In addition, the active methodology allows for the regeneration of most of the cells in the human body by facilitating the maintenance, integrity, and repair of the individual's DNA. This regeneration of cells includes those of the human CNS by inducing changes in the two main pathways of protein degradation: the autophagy cycle and the ubiquitin-proteasome pathway (UPP) as first described in more in supporting FIG. 17E in the human cells in addition to the active methodology that includes, eventually, for some patients some creative activities during SBOT sessions. These creative activities involve and utilize;

(1) intermediary objects such as the participant's use of balloons, scarfs, floor, chair, mat, wheel chair, etc. by developing creativity in the audiovisual portion of the health improvement treatment in the doctor/individual's room;

(2) creative painting, drawing, modeling with clay or some other non-toxic materials, (3) the induction of the individual's spontaneous free form of movements matching the steps of the developing mobility in a child, and (4) the creation of images by the use of smart phones, computer tablets, laptops, or other computer operated equipment that includes any networked computer devices.

The connections can be provided to the world wide web/internet, extranets and internal networks as needed. These devices include cameras or other devices as required by the individual (or administering doctor/health care professional or educator) that are present in the patient's room.

All forms of creative activities that are provided in the audiovisual room during SBOT sessions promote a better up-regulation of growth factors (GFs)/human growth hormones (HGHs) which may lead eventually to major potential improvements for the benefits of the most physically and mentally handicapped individuals. Further improvements in human health include; improvement of the human immune system, motor skills, social behavior, communication skills, parental relationships, better control of body mass (weight), the aging process, circulation, maintenance and repair of the bones, improvement in the period of development of the child toward adulthood, the healing process after an accident or trauma, as well as better recovery after surgery.

Referring back again to FIG. 1, details are presented that illustrate some aspects of how application of the SBOT sessions and associated methodology (the use of sonoluminescent biophysical oscillations on the human body) in developing both the active and receptive mode that includes sessions that average at least one minimum session per day to at least one session per each week over at least 1-3 months and often 6 months. In fact for certain individuals, it is often necessary to provide up to 1-5 years of SBOT treatment that involves intermittent repetitive applications. These repetitive applications lead to induced changes in the predominant human brain rhythms for each phase of the sonoluminescent biophysical oscillations over 10 minutes. The prework described in FIG. 1 indicates that in addition, there is a music-light-color/images test available for each individual to improve the sonoluminescent biophysical oscillations sessions whenever possible. This test helps provide better individualized selection of music-light-colors/images for each phase of the sonoluminescent biophysical oscillations by targeting better emotional responses of the individuals during respective individual and/or group session(s).

Figure 32A:
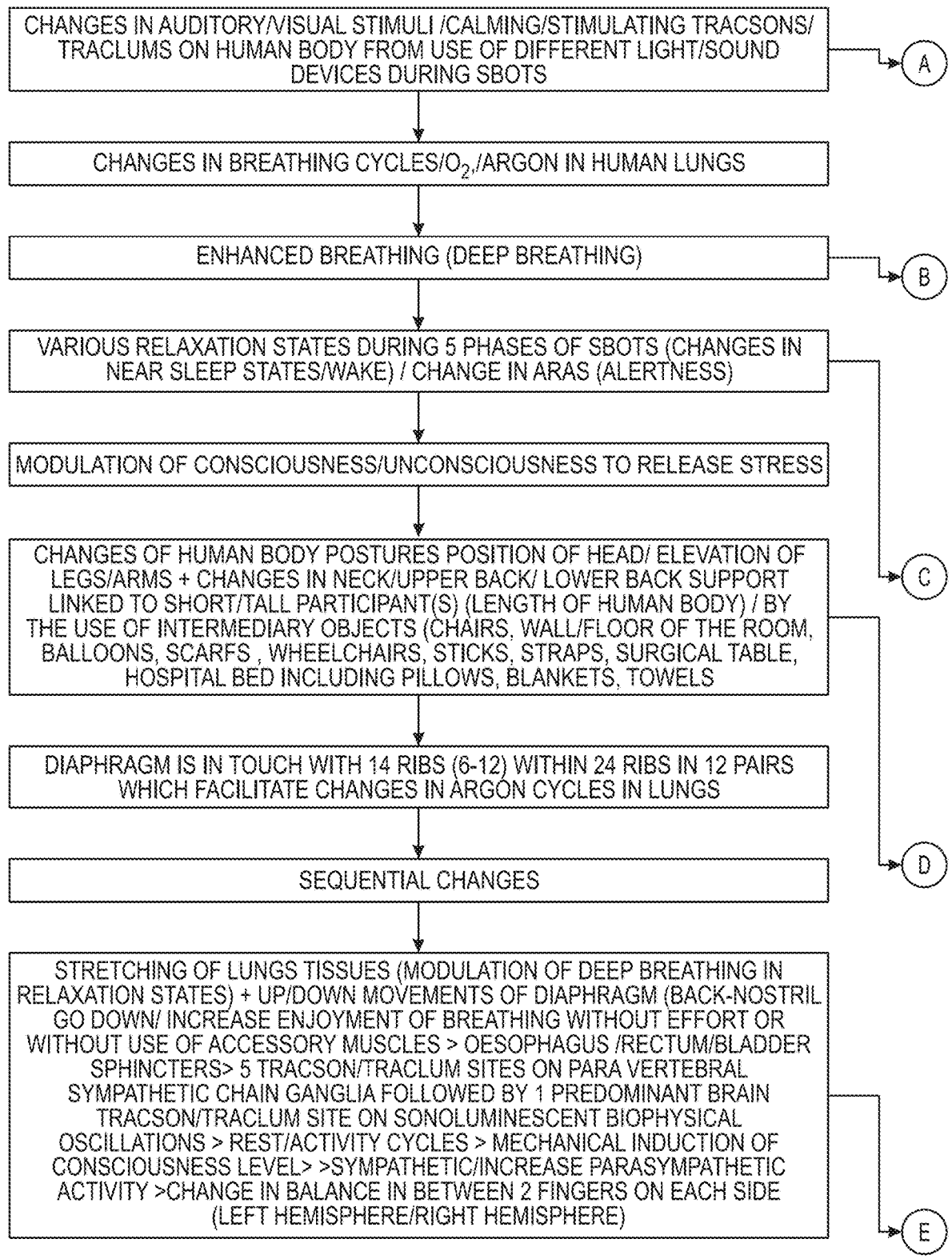
FIG. 32A-D describes in detail SBOTs within the human body systems and associated improvements.
Figure 32B:
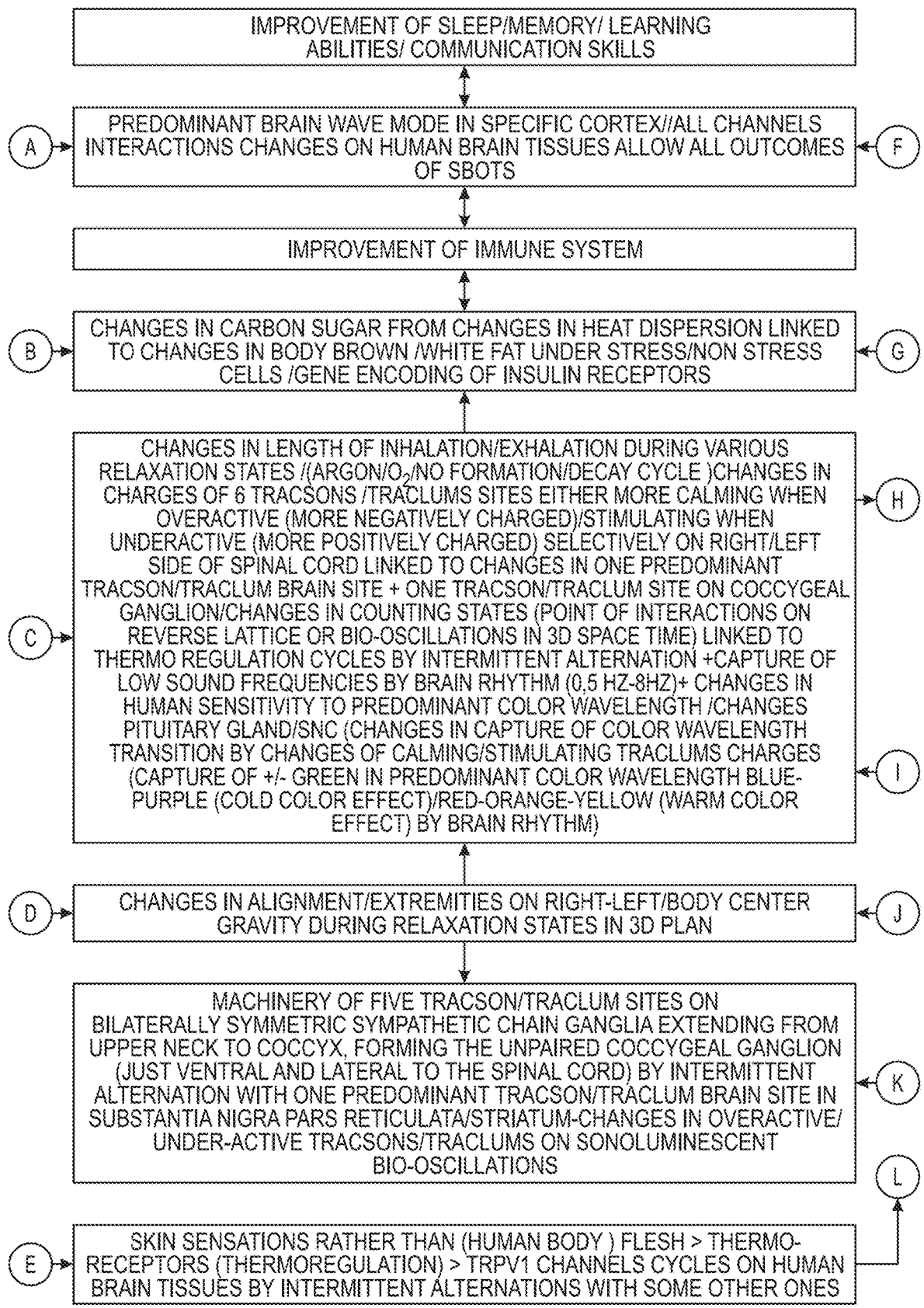
Figure 32C:
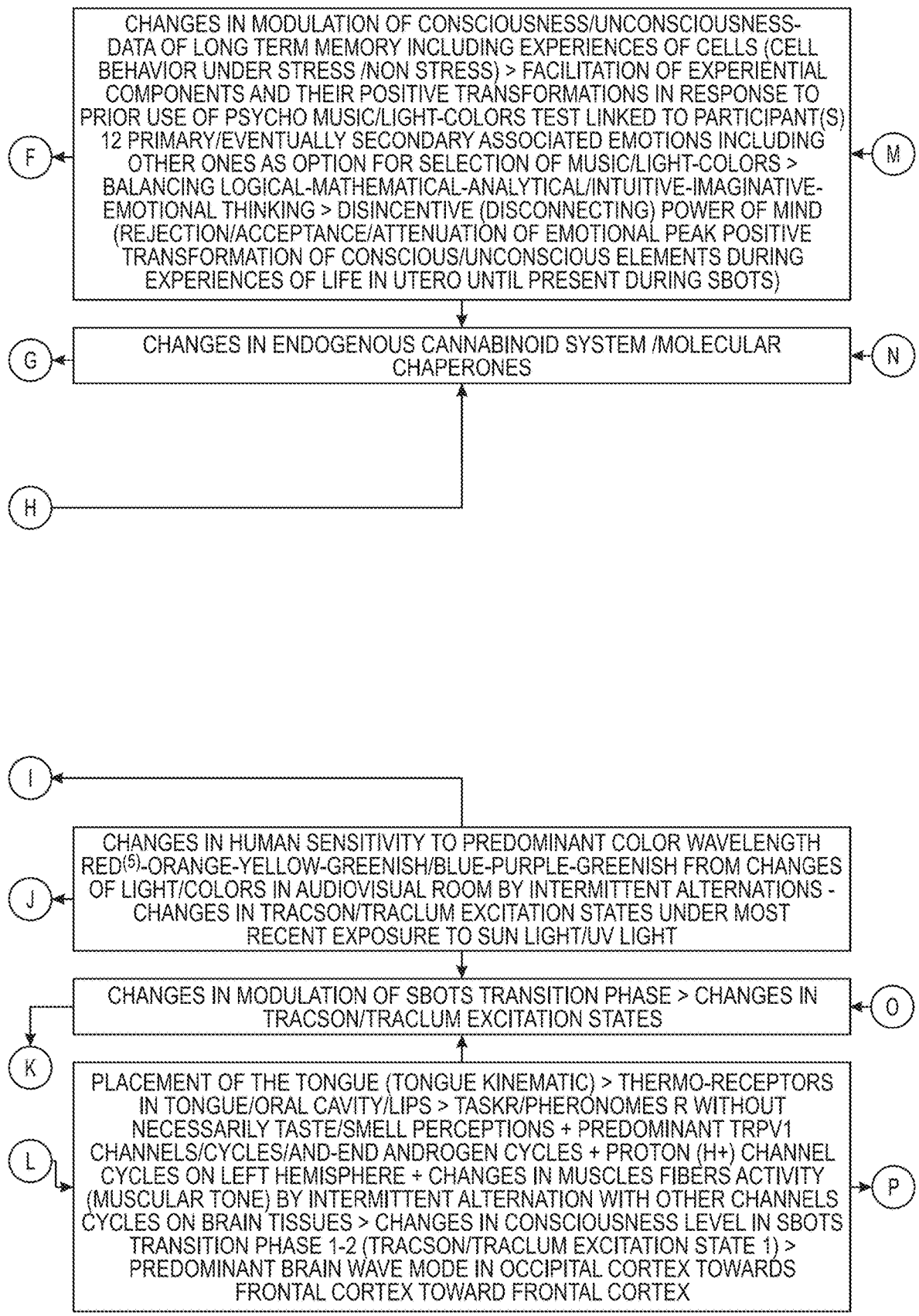
Figure 32D:
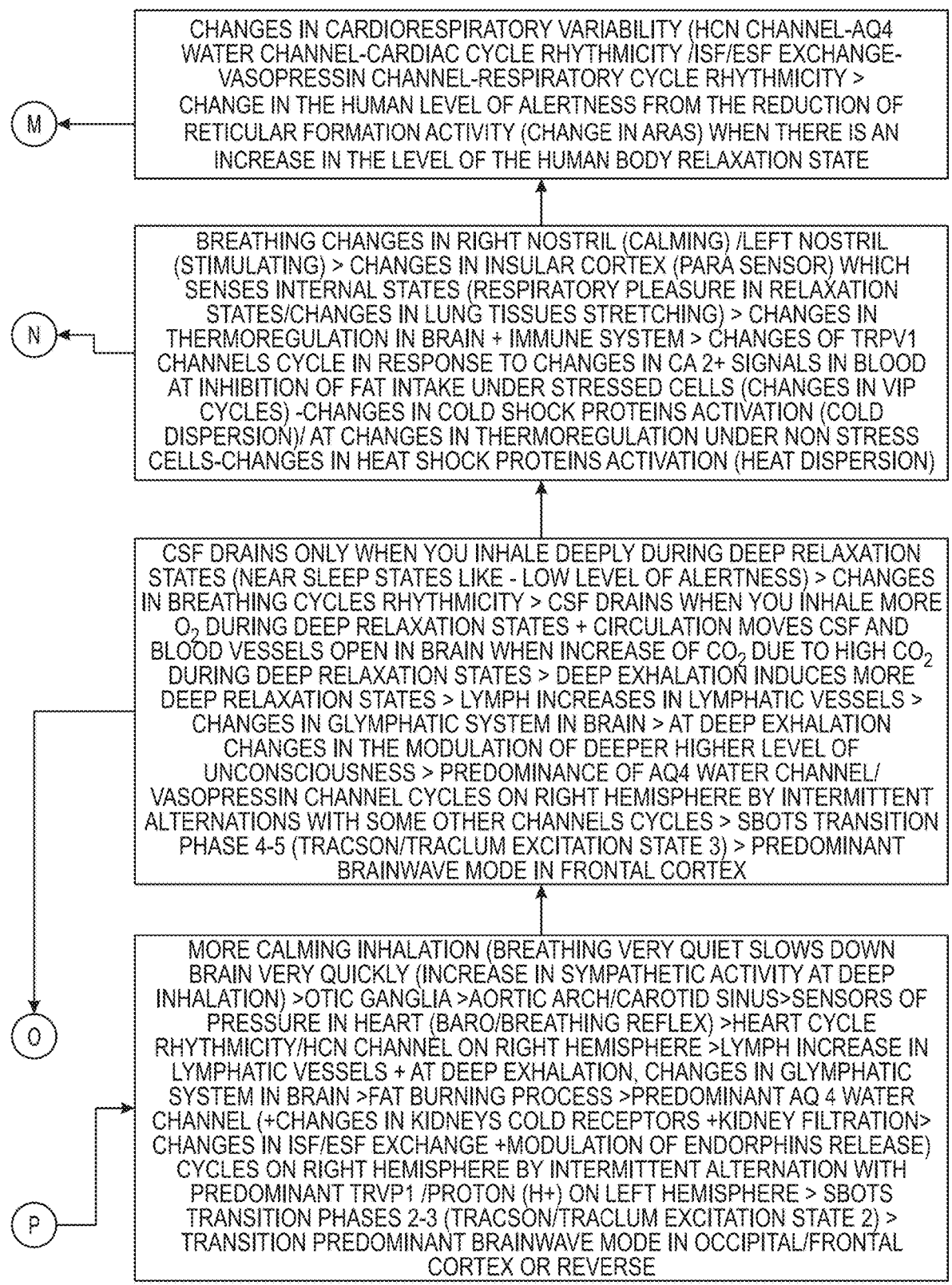

Using individualized SBOT sessions enhances the individual's subjective experienced feelings from induced changes including induced changes in the human mood center from induced changes in oxytocin (shown in FIG. 12A)—associated with anger management-, as well as vasopressin (associated with anxiety-panic management and described best in FIG. 32D) in the human brain tissues. These changes in the human mood states are a direct result of induced changes in the transitions of human subjective experienced feelings during the application of the SBOT techniques during the SBOT sessions. The sonoluminescent biophysical oscillations cause a response which translates into induced changes in the states of relaxation during the applications of the sonoluminescent biophysical oscillations on the human body. During the applied active methodology on the human body, there are induced changes in the activation of the alpha synuclein proteins which contribute to eventual potential regeneration of human brain tissues, induced changes in the activation of small heat shock proteins (sHSPs) such as mainly alpha beta crystallin or CRYAB which leads to eventual potential regeneration of the human body tissues including neurodegenerative tissues.

Alpha-A is preferentially restricted to the lens and alpha-B is expressed widely in many tissues and organs. Elevated expression of alpha-B crystallin occurs in many neurological debilitations; a missense mutation co-segregated in a family that has a desmin-related myopathy (DRM).

In addition, the SBOT treatment provides induced changes in HUNTINGTIN gene (HTT) expression which contribute to the regeneration of the central nervous system (CNS) which results in better human body movement capabilities including better coordination resulting in improvement of motor skills. These improvements are primarily the result of associated induced changes in the human frontal cortex activation, a part of the brain that controls thinking and emotions. Using the SBOT methodology therefore provides an ability to think/respond emotionally more positively, especially during the transitions phase 3-4 and 4-5 of the applied SBOT and in addition to induced changes which occur in the striatum (a part of the brain that coordinates movement). In addition, the striatum coordinates multiple aspects of cognition, including both motor and action planning, decision-making, motivation, reinforcement, and reward perception.

This improvement in cognitive ability is achieved via a complex mechanism which turns the light emission activation switch on and off and allows for capture and release on specific human body parts of hydrophobic patches found within red blood cell cellular membranes during general blood circulation. This process eventually transforms the induced light energy in most human body cells into metabolic energy during the applications of the SBOT treatment for human health improvement.

Human genes are segments of DNA that are organized by 23 pairs of chromosomes from each parent. DNA encodes proteins, known as the "workhorses" of the cell responsible for all the functions necessary for life. It is known that humans have ~20 000-25 000 genes in their genome and each individual has genes that vary by a few alleles. These genes/alleles can be represented by horizontal segments that connect ladder-like strands of DNA. Changes occur in these genes which are referred to as "SNPs" or single nucleotide polymorphisms and gene variants. SNPs are inherited over many generations influenced by the geography of our ancestors, epigenetic changes in diet, environment, and lifestyle. The epigenetic signals eventually are capable of being changed to assist our genome to function in a more optimal manner. DNA, however cannot be easily altered and normally remains fixed to maintain its integrity or repair during the application of SBOT. It is possible, over time with the use of SBOT to induce changes in some of the integrity/repair of DNA in some cells by reducing the stress level during states of relaxation, invoking human emotional transitions that assist with potential development of a sense of purpose in life, free form of spontaneous movements or self-expression changes so that degenerative tissues of individuals can be regenerated in response to these induced changes. As shown in FIG. 1 and then again in FIGS. 6A and 16, in many cases, the dominant human brain rhythms that exist in t h e frontal/occipital cortex of the brain can be reversed by intermittent applications resulting from induced changes in the interactions of the tracsons/chromophores on 7 sonoluminescent biophysical oscillations sites (see FIG. 6A and FIG. 16) on the human body. For each phase of the sonoluminescent biophysical oscillations which lead to induced changes in two main pathways of protein degradations in the human cells such as the autophagy cycle and the ubiquitin pathway (UPP), there are eventually potential induced changes in the expression of certain hereditary susceptibilities which have an influence on the human health and human tissue of many of the individuals that benefit from SBOT.

The Chromophores (2): How they Work and how they Interact with Tracsons During Applied Biophysical Oscillations on the Human Body In order to understand SBOT methodology, it is useful and informative to further understand the use of chromophores and how they interact with tracsons. As shown again in FIG. 3, the chromophores interact with the tracsons by intermittent repetitive applications on 7 sites of the sonoluminescent biophysical oscillations pathways over approximately 10 minutes for each phase of the sonoluminescent biophysical oscillations in response to the human body's reception and perception of specific sound/visual stimuli from tracsons/chromophores stimuli. As shown in FIG. 2, the tracsons/chromophores for the SBOT methodology also include a respective integration in between two fundamental notes played in music/in between two light-colors- and optionally-two images that causes transitions. The transitions occur over ~3-5 seconds by using intermittent repetitive applications that target approximately 4-10 notes played in the music composition, as well as 4-10 two light-colors and optionally showing 2 images, where the transitions require a duration of ~1-4 seconds for a period of 1-3 minutes during an approximate 10 minute induction time period in order to complete each phase of the SBOT process Further shown in FIG. 2 is how the human perception of chromophores which comes from specific stimuli as a result of the transitions of light-colors in between 2 light-colors and/or eventually in between 2 images in an audiovisual room that includes intermittent repetitive applications during each phase of the sonoluminescent biophysical oscillations results in induced changes in the human sensitivity to different color wavelengths reflected in the induction of different color gradients appearing in 2 light-colors/optional 2 image transitions. FIG. 1 and then again FIG. 6B provide information regarding the fact that resulting predominant tendencies are either skewed toward warm colors such as red-yellow-orange-green and/or toward cold colors such as blue-green-purple in the audiovisual room. These tendencies occur due to induced changes in the color filters used in one or more computer programs for the selection of light-colors/images-slide shows, in addition to the use of associative tools creating many and varying effects by inducing changes in the shaded and/or brightened portions between 2 light-colors/optional 2 images in each individual respectively.

As further described in FIG. 6B, when the absorption of blackness and/or the reflection of whiteness takes place this often leads to respectively induced changes in opacity/transparency in the light-colors/optional two images transitions as well as other induced changes in the proximal and/or distal human perception of light-colors/images transitions. This process allows the integration of chromophores with light colors/optional two images in the audiovisual room and the induction of specific stimuli including chromophores which are received and perceived by the human body during the application of SBOT methodology. In this manner, the chromophores induce some "eye jumps" or twitches which occur because of induced changes in the retinal edge displacement as a result of induced changes in human eye movements. The speed of the "eye jumps" is directly proportional to induced changes in the predominant human brain rhythms which causes induced changes in human sensitivity to color wavelengths of visible spectrum of light-colors in response to induction of chromophores when the human body is submitted to sonoluminescent biophysical oscillations in an audiovisual room. FIG. 6B also indicates that the integration of the chromophores in between two light-color/optional two image transitions provide for changes in the shaded and/or brightened portion of the light-colors of the visible spectrum, so that either blackness absorption or whiteness reflection takes place. In addition, there are induced changes in the opacity/transparency in the light intensity and colors of the visible spectrum in association with induced changes in the predominant color gradient either toward cold colors such as blue-green-violet and/or toward warm colors such as red-orange-yellow-green.

As previously described, the chromophores interact with the tracsons by intermittent repetitive applications on 7 sites of sonoluminescent biophysical oscillations pathways over ~10 minutes for each phase of the sonoluminescent biophysical oscillations from the human body's reception and perception of specific sound/visual stimuli from respective tracsons/chromophores stimuli and their respective integration in between two fundamental notesplayedinmusic/inbetweentwolight-colors/optionaltwoimagetransitionsover 3-5 seconds by intermittent repetitive applications that target approximately 4-10 notes played in the music composition/-4-10 two light-colors/optional two image transitions within 1-4 seconds over 1-3 minutes during-10 minutes which represents the induction time period for each phase of the sonoluminescent biophysical oscillations. As this SBOT process occurs, and as shown in FIG. 6A, it is also possible to obtain induced changes with an argon matrix creating induced changes in argon (from activation of the argon matrix at the speed of light in specific cerebrospinal fluid (CSF) filled cavities (made of 99 percent water)/photons (from its activation of the porphyrin photopigment of red blood cells at the speed of light in response to human body light-colors exposed in the audiovisual room. This occurs in association with the most recent individual exposure to sunlight and UV light that provides an energy gradient sequentially in specific cerebrospinal fluid (CSF) filled cavities such as the first central canal in the spinal cord. Once this Argon augmented process begins, each of the connected fluid-filled cavities in the center of the brain such as the fourth ventricle, third ventricle and the two lateral ventricles are affected.

Figure 7A:
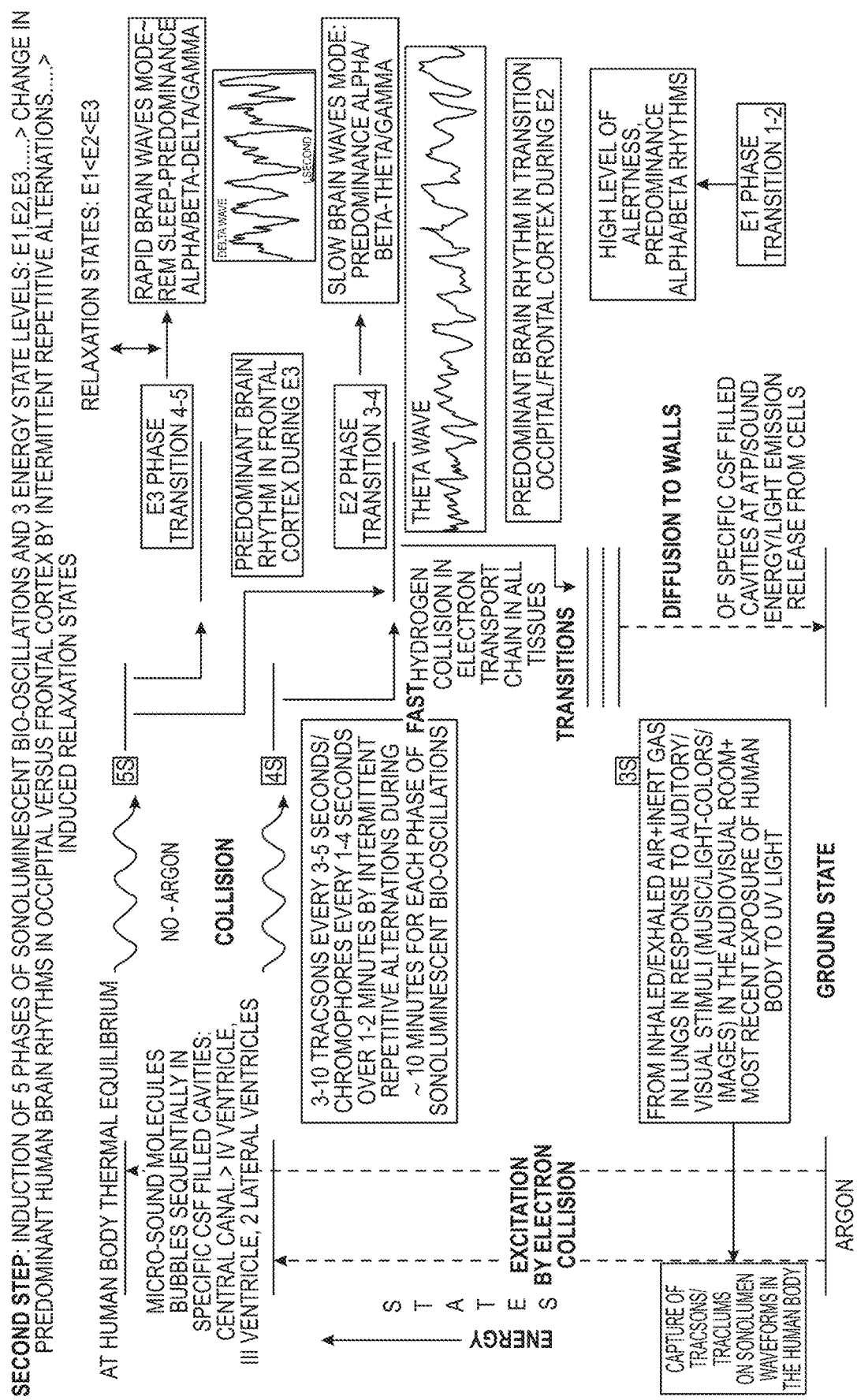
FIG. 7A is a schematic that describes the second step for the induction of 5 phases of SBOTs and 3 related energy state levels (−E1, E2, and E3) responsible for change in the human brain rhythms in the occipital and frontal cortex by alternating intermittent applications of the SBOTs to induce relaxation states that change the human state of health and allow healing to take place.
Figure 7B:
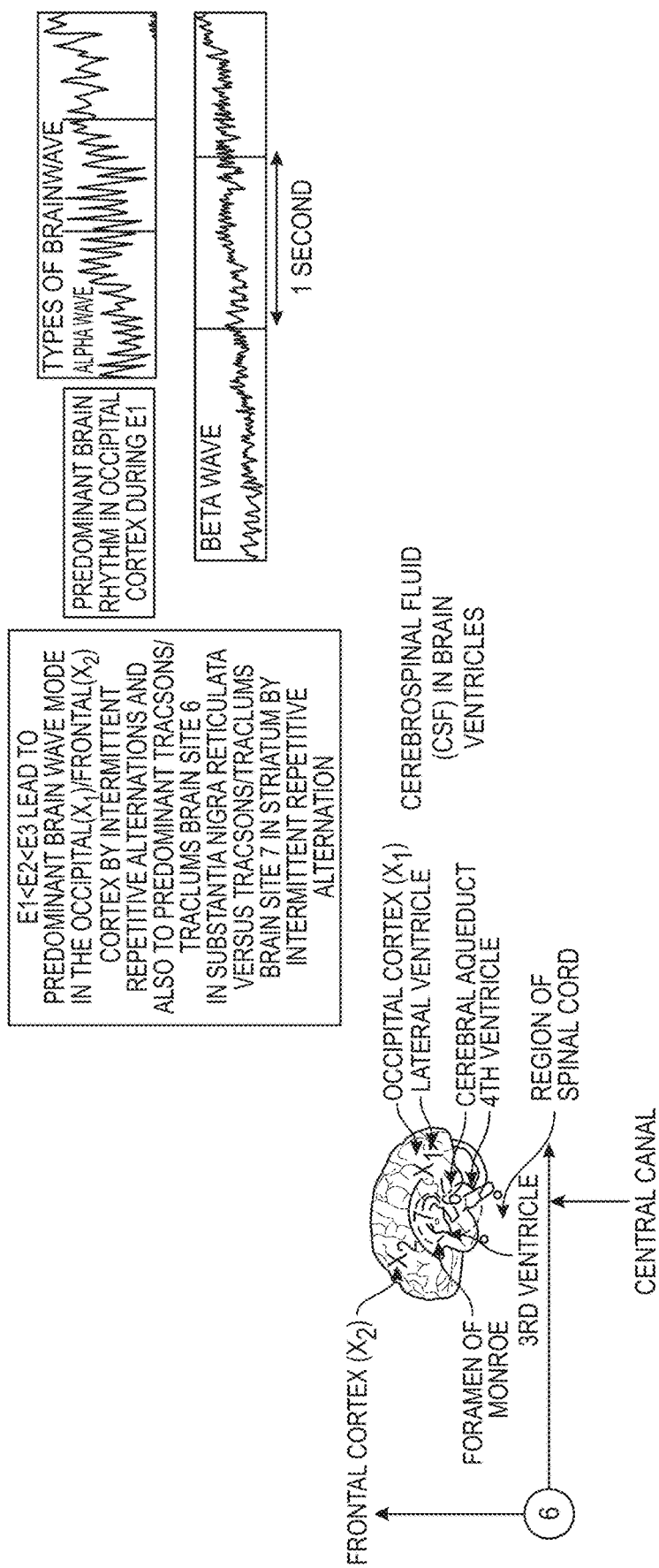
FIG. 7B is a schematic that shows a side view of the human brain and describes in detail how the changes in brain waves occur by implantation of the SBOT state of health improvements and specifically how the prefrontal cortex is affected.
Figure 7C:
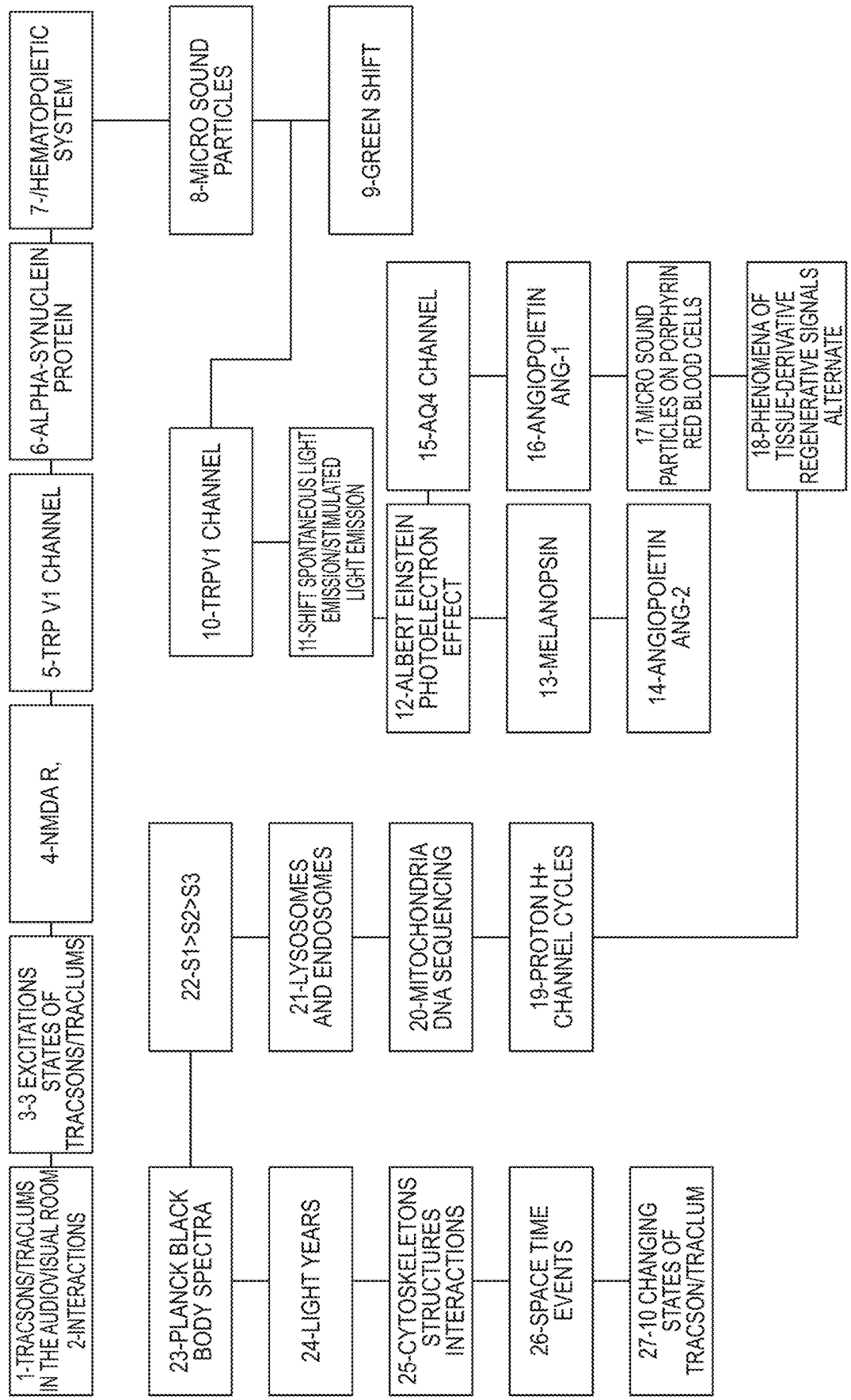
FIG. 7C describes the color shift experienced during SBOTs

FIG. 7A shows that this procedure is followed by induced changes in the activation of a hydrogen pump with the human cells that includes their activation of the mitochondrion of their electron transport chain. This process creates induced changes in hydrogen (from its activation along the electron transport chain)/photon (in association with the activation of induced changes in the proton gradient in response to induced changes in UV light absorption in the human cells via activation of photopigment flavin).

Figure 15A:
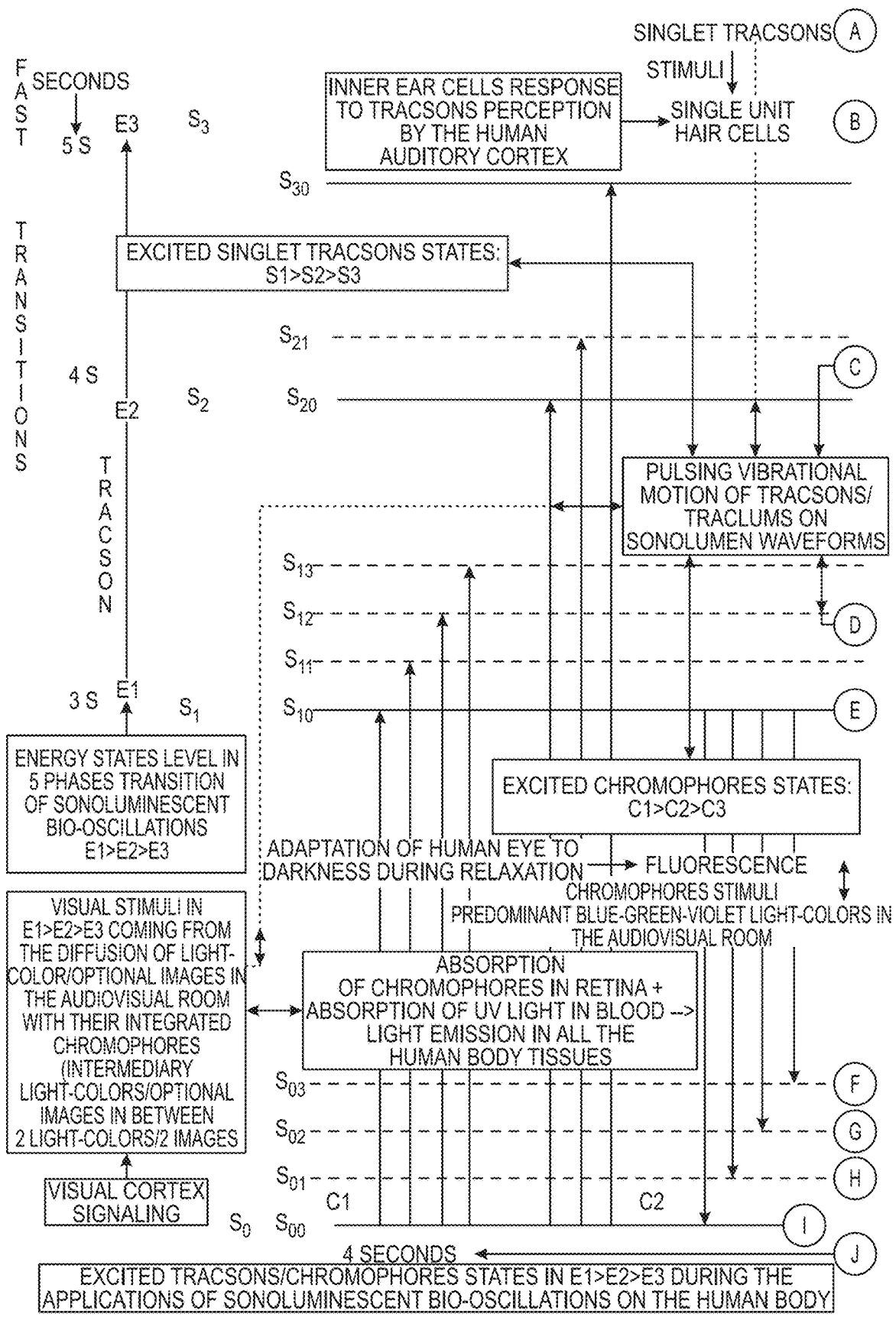
FIG. 15A is a schematic that illustrates how the excited tracsons are utilized to induce excitation of the traclums, including the induction of photofluorescence and the slow transition of excited chromophores, during the application of the SBOT state of health improvements.
Figure 15B:
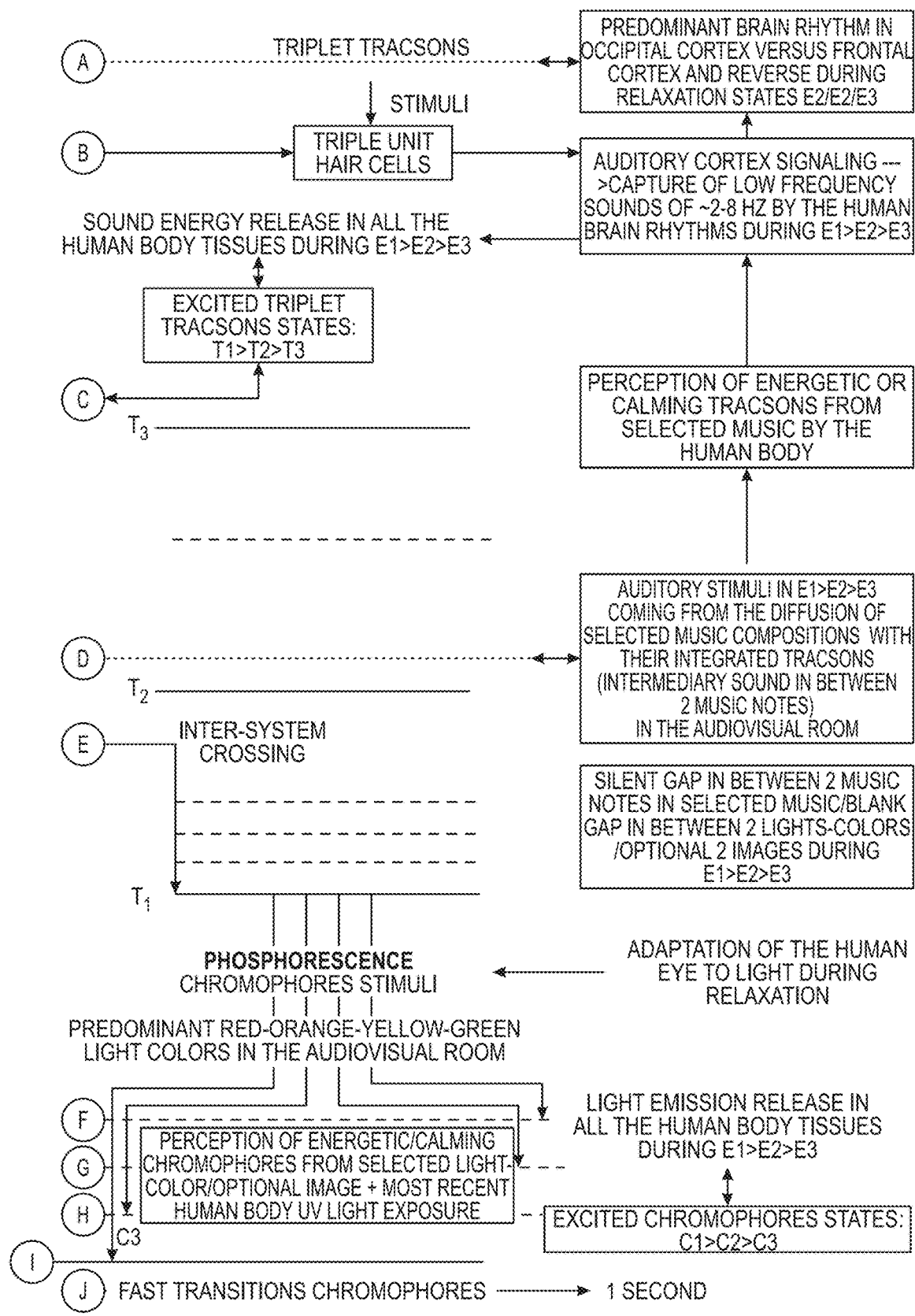
FIG. 15B is a schematic that further describes the process of FIG. 14A including the induction of photophosphorescence and the rapid (fast) transition of excited chromophores.

As also shown in FIG. 6A, this photopigment flavin is sensitive to blue-green light and by the use of intermittent repetitive applications of the light during relaxation states activation of the chromophore synthesis in all the cells in the human body respond. The human body perception of chromophores interacting with tracsons by intermittent repetitive applications over 10 minutes for each phase of the sonoluminescent biophysical oscillations and the induced changes in the predominant human brain rhythm over 10 minutes in occipital/frontal cortex and reverse) energy gradient leads to induced changes in the interactions of tracsons with chromophores on 7 sonoluminescent biophysical oscillations sites by intermittent repetitive applications over 10 minutes for each phase of the sonoluminescent biophysical oscillations. In addition, during this process, there are induced changes in the manifestation of the sonoluminescent biophysical oscillations flow and their elongations as 3D sonolumen waveforms in space-time by intermittent repetitive applications of tracson/chromophore interactions with zero energy on 7 sites of the sonoluminescent biophysical oscillations. FIG. 6A, illustrates that induced changes in argon-photon energy gradient/hydrogen-photon energy gradients consequently, predominantly in response to the human perception of newly sequentially induced chromophores interacting with tracsons on 7 sites of sonoluminescent biophysical oscillations by intermittent repetitive applications over 10 minutes for each phase of the sonoluminescent biophysical oscillations during application on the human body, both in active and receptive mode, induce changes in the human condition. These receptive mode induced changes occur in the activation of neuromelanin pigment (found primarily in the dopaminergic neurons of the human substantia nigra). This process also provides for the emergence of a primary player in the human neurodegenerative tissues)/retinal (in association with retinol-binding protein that represents a key molecule involved with vision and also a carotenoid constituent of visual pigments, responsible for converting the energy of light into metabolic energy). FIG. 15B is a schematic that shows how these induced changes lead to chromophore sensors that affect the human brain tissues with dominant sensitivity to color wavelengths such as yellow-orange-red-green, characteristic of phosphorescence as well as (as shown in FIG. 15A) adaptation to light and/or in response to predominant sensitivity to color wavelength such blue-green-purple, characteristic of fluorescence. These induced changes also provide for improved human body adaptation to darkness (again schematically shown in FIG. 15A) and in addition cause proximal/distal stimuli of the human perception of the transitions between 2 images during the induction of different relaxation states while the applications of the sonoluminescent-biophysical oscillations is ongoing. This process facilitates the dissolution of misfiled proteins in human brain tissues which is known to beat least one cause of brain tissue degeneration.

The chromophores have induced effects on the human body which can then be utilized to provide induced effects on the individual that is having the SBOT methodologies applied to them and described herein.

(1) FIG. 6A also indicates that the chromophores allow for induced changes in the activation of alpha-synuclein proteins in human brain tissues with cells that are in the stress and non-stressed condition (which contribute to the eventual regeneration of the human central nervous system). FIG. 2 illustrates that these alpha-synucleins are found mainly at the tips of nerve cells (neurons) in specialized structures known as presynaptic terminals within their relays on five tracsons/chromophores sites situated on the paravertebral sympathetic ganglions chain. These sites have a direct influence on one predominant tracson/chromophore site that exists in the occipital/frontal cortex of the brain and which can be treated by intermittent repetitive applications and from induced changes in the activation of chromophores interacting with tracsons on seven sites of the sonoluminescent bio-oscillations. By making these interactions cause changes, the induced changes in the human body results in adaptation to light/darkness and its sensitivity to predominant color wavelengths in the audiovisual room. These applications are as a result of the applied methodology of tracsons/chromophores on the human body using the SBOT methodologies to improve human tissue described herein. There are also induced changes in the alpha-synuclein activation in the pars reticulate portion of the substantia nigra in response to induced changes in the activation of the human thermo-receptors such as cold/warm sensations (from induced changes in cycles of the vanilloid family of transient receptor potential cation channels (TRPV) in the human brain tissues). It is known that TRP channels are highly calcium selective. There also induced changes in the active/passive human muscular activity (from induced changes in proton channel cycles in the brain tissues) during the application of the sonoluminescent biophysical oscillations which manifest during the induced changes in the predominant human brain rhythms. During induced changes in the human brain tissues with stressed and non-stressed cells, the induction of different levels of relaxation states can be achieved with the applied SBOT methodologies that contribute to the eventual potential regeneration of the human brain tissues.

(2) It is also possible to provide induced changes in the activation of sHSPs (small heat shock proteins) such as mainly in the form of alpha beta crystallin which acts as molecular chaperones and which are more prominent in glial cells than in neurons, and which prevent the aggregation of proteins after stress on neural cells. This activation of the sHSPs is limiting regarding the capacities for refolding stressed proteins and they also represent prominent constituents of inclusion bodies originating in glial filament inclusions such as in astrocytes and oligodendrocytes in neurodegenerative tissues. This activation of the sHSPs is also associated with induced changes of cytoskeleton proteins in neural cells during normal and stressful conditions.

The expression of alpha beta crystallin eventually may be modified during the application of sonoluminescent biophysical oscillations in response to induced changes in various cycles of channel activations including TRPV1 (vanilloid (capsaicin) receptor and noxious thermo-sensors that are distributed in the CNS and PNS) proton and water channels on brain tissues by intermittent repetitive alternation under stressed and non-stressed cell conditions. Many stimuli have been found to activate ion channels present on nociceptor terminals that act as molecular transducers to depolarize these neurons, thereby setting off nociceptive impulses along the pain pathways (Price, 2000; Costigan and Woolf, 2000). Among these ion channels are the members of the transient receptor potential (TRP) family. To date, the most studied member of the TRP family is the TRPV1 receptor. The induced changes in the predominant brain rhythms during the applications of the sonoluminescent biophysical oscillations on the human body in both an ATP-dependent and independent manner in the neural cells can occur due to the expression of alpha beta crystallin as well.

In addition, induced changes in the expression of alpha beta crystallin also affects major proteins in the composition of the human eye lens and also found in the cornea of the human eye, but also expressed widely in many tissues including muscle tissues as well as some other organs. These induced changes are in response to the human body light adaptation during the induced relaxation cycles that involve 5 different phases of the sonoluminescent biophysical oscillations. In summary, this process leads to eventual potential regeneration of human body tissues including neurodegenerative tissues.

sHSPs are also involved in the stabilization or elimination of associated proteins which are linked to neurodegenerative tissues and are components of filamentous inclusions found in a variety of defects in the Alpha-crystallin B chain gene/protein. This stabilization or elimination also provides for assistance with improving degenerative tissue including neurodegenerative tissue medical outcomes for individuals.

(3) In yet another embodiment it is possible to use SBOT to provide induced change in HUNTINGTIN gene (HTT) expression involved with the long term memory storage. The HTT gene provides instructions for making a protein called huntingtin. Although the exact function of this protein is unknown, it appears to play an important role in nerve cells (neurons) in the brain and is essential for normal development before birth. Huntingtin is found in many of the body's tissues, with the highest levels of activity in the brain. Within cells, this protein may be involved in chemical signaling, transporting materials, attaching (binding) to proteins and other structures, and protecting the cell from self-destruction (apoptosis). These HTT induced changes are often expressed in many tissues of the body with the highest level of expression seen in the brain. This allows for up regulation of the brain derived neurotrophic factor (BDNF) that also acts on certain neurons of the central nervous system and the peripheral nervous system. In addition, this provides support for the survival of existing neurons, and encourages the growth and differentiation of new neurons and synapses. There are also induced changes in HTT gene expression that contribute to the regeneration of the central nervous system during the applications of sonoluminescent-biophysical oscillations in response to induced changes in the human body muscular tone during the relaxation states.

This change includes the involvement of passive movements (from the holding of the human body posture in relaxation mode) so that induced changes in the expression of HSP 27, a chaperone of the sHSPs (small heat shock protein) group among alpha-crystallin, provides a response to stress put on muscle fibers. These induced changes occur due to the onset of activation of chloride ion channels on skeletal muscles under stress and in response to induced changes in the activation of different brain channels on brain tissues. This treatment is particularly effective for cells under stress and can be applied with intermittent repetitive applications that lead to better human body movement and coordination for improvement of motor skills.

Much of this SBOT technique and associated methodology is primarily in association with induced changes in the human frontal cortex activation, a part of the brain that controls thinking and emotions) and provides the ability to think and to respond emotionally more positively especially during the transitions phase 3-4 and 4-5 of applied sonoluminescent bio-oscillations.

In addition to induced changes which occur in the striatum (a part of the brain that coordinates movement) and in response to respectively induced changes regarding the level of serotonin in the gut, it is possible to better control stress during relaxation states in association with induced changes in the human body gastrointestinal motility and its associated lipid metabolism. This stress control mechanism is a complex mechanism that provides for turning the switch on and off for light emission activation and captures and releases specific human body hydrophobic patches found on red blood cells. This includes cellular membranes in the general circulation of the blood, a process which eventually transforms the induced light energy in most of the human body cells into metabolic energy during the applications of the sonoluminescent biophysical oscillations.

In response to specific visual stimuli from chromophores as a result of individual exposure in the audiovisual room during the applications of the sonoluminescent biophysical oscillations on the human body, the transmission of retinal image edge information from arbitrary light occurs. A portion of the left/shaded portion to the right in the human visual system transfers the edge imaged signals, and results in an "eye jump". The eye jump occurs from a retinal image displacement followed by a change in the eyes movement and the human brain rhythm. The retina edge represents the segment of the edge imaged on a portion of human retina that separates the light portion of human retina from the mixing of colors. Induced changes in edge information of the retina from induced changes in the shade (transparency/opacity) of light-colors-images and their color gradient either toward red-yellow-orange-green (warm color tendency) or toward blue-green-purple (cold color tendency) results in changes in human sensitivities to color wavelength in association with human adaptation to light/darkness during applications of the sonoluminescent biophysical oscillations.

Here, the induced changes in the chromophores interacting with tracsons by intermittent repetitive applications on 7 sonoluminescent biophysical oscillations sites from induced changes in the light/sound emission influence the tissues of the human body during the fixation in between the eye jump for each phase of the sonoluminescent biophysical oscillations. There is also generation of a package of information for the retina by intermittent repetitive applications such as overlap and change in the absorption of color wavelength and light emission oscillation on the retina from the opening and closing of the eyes and the induced changes in the speed of rapid eye movement during the induction of different states of relaxation for each of the five phases of the sonoluminescent biophysical oscillations.

SUMMARY OF THE INVENTION

As stated above, the present disclosure describes and is instructive regarding how to accomplish SBOT(s) that cause a response that includes regeneration of any tissue, organ (including skin), bone, ligaments, and/or muscle in or on the human body. It is especially beneficial for those individuals that are weakened or have a fragile constitution and/or deficient genetic predisposition and/or degenerative condition including atrophied tissues as well as post trauma factors. This includes help for individuals who become participants in SBOT experiencing symptoms associated with major accidents or deep frustration, emotional and/or physical abuses as well as traumatic experiences. SBOT can also be helpful for other issues that cause stress responses within human cells. The use of desired and/or necessary instruments and devices required for SBOT are provided for individuals that possess the same or similar conditions. More specifically, the present disclosure and associated embodiments provide one or more devices which together provide sonoluminescence biophysical oscillation technique(s) (SBOT(s)) to alleviate individualized debilitating symptoms exhibited by one or more humans comprising; at least one room that contains one or more sound emitting devices that include speakers that provide biophysical oscillations that initiate, sustain, and/or control transmission of harmonic and subharmonic sound(s) including music and/or individual musical notes that provide sound tracsons and also one or more light emission devices including projectors that provide light wave emission traclums that impart changes in color and/or colored wavelengths of light wherein the tracsons and the traclums supply auditory and visual stimuli that causes specific energy changes, wherein the specific energy changes create chromophore excitations wherein the chromophore excitations are applied to one or more external portions of one or more human bodies.

The SBOT(s) results in a change of regulation of Human Growth Hormone Factors (HGHF) to one or more individuals subjected to SBOT and are designated as participants.

Here the SBOT(s) results in a change of regulation of Human Growth Hormone (HGH) to one or more groups of participants.

In addition to sound and light and color changes leading to the chromophore excitations, creative participants are either provided or the participants themselves provide individualized activities that are utilized to further improve human health conditions the health conditions selected from one or more of a group consisting of, improvements in a vasopressin center for anxiety, pain, and analgesic issues, an oxytocin center, DNA and CNS (central nervous system) repair, and retinol/neuromelanine regeneration.

The SBOT(s) is delivered together with sound and light emitting devices that are activated, utilized, and controlled by one or more computer devices, wherein the computer devices are selected from one or more of a group consisting of: cellular phones, smart phones, laptops, networked computers, computer pads, televisions, radios, and transceivers, wherein the transceivers can be transmitters and/or receivers and either transmit or receive or transmit and receive energy within a confined indoor space that includes an indoor space designated to be an audiovisual room.

This embodiment allows for the energy to be sent or received from a selection of a form of energy, the form of energy selected from at least one of a group consisting of: optical, electrical, mechanical, radiative, solar, and wind energy.

In most embodiments, the form of energy is sent directly, as an energy signal or an energy wave that is transmitted to and received by a human body.

The devices here deliver SBOT(s) applied to improve one or more conditions associated with a human body selected from one or more of a group consisting of: human bones/skeletal structure, human tissues, human nerves, and human organs including human skin.

In at least one embodiment devices include at least one or more creative activities delivered to one or more individuals receiving SBOT(s) via a person, equipment and/or by utilizing a virtual equivalent thereof and wherein the creative activities include making and/or listening to music, drawing, sculpting, writing and painting wherein the individuals apply manual dexterity that includes an individual touching and/or playing musical instruments.

In some embodiments the devices include at least one or more creative activities delivered to one or more individuals wherein the creative activities include a patent's use together with administering SBOT(s) that utilizes intermediary objects wherein the intermediary objects are selected from at least one of a group consisting of: balloons, scarfs, floor chai, mats, and wheel chairs.

The devices include at least one or more creative activities delivered to one or more individuals wherein the creative activities are selected from at least one of a group consisting of: creative painting, drawing, hand modeling with clay and other substances that allow for hand modelling.

In at least one embodiment the devices include the at least one or more creative activities delivered to one or more individuals wherein the creative activities include administration of or participation with free form movements to/with one or more participants or group of participants.

In another embodiment the devices are capable of delivering i at least one or more creative activities delivered to one or more participants wherein the creative activities include creation of one or more images by one or more of the devices and/or computers/cameras such that the creative activities are received and in some case created by one or more participants to which SBOT is administered.

It is also desirable that the SBOT induces deep relaxation states in one or more participants by implementation of rotation and/or intermittent application(s) in a series of SBOT to provide a positive response to the participants.

In this and other embodiments the deep relaxation states are a result of directed and focused SBOT to a frontal cortex of a human brain and reversal of SBOT by intermittent applications over time to accomplish a positive response in a participant.

In this and additional embodiments the SBOT(s) are administered by a trained professional that is a trained medical professional or a person that has been trained to perform SBOT(s) and is not a trained medical professional.

In all embodiments it is possible that the SBOT is administered to an animal.

There are also additional embodiments that include both a system and a method that provides sonoluminescence biophysical oscillation technique(s) (SBOT(s)) to alleviate debilitating human conditions of individuals comprising; at least one room that contains one or more sound emitting devices that includes at least one speaker that provides biophysical oscillations that initiate, sustain, and/or control transmission of harmonic and subharmonic sound(s) including music and/or individual musical notes that provide sound tracsons and also one or more light emission devices including projectors that provide light wave emission traclums that impart changes in color and/or colored wavelengths of light wherein the tracsons and the traclums supply auditory and visual stimuli that causes specific energy changes, wherein the specific energy changes create chromophore excitations wherein the chromophore excitations are applied to one or more external portions of one or more human bodies.

Working Example: Use of Sonoluminescent Biophysical Oscillations (SBOTs) Combined with Massage for Pain Management SBOTs can be used for participants in birthing centers as well as in medical facilities including oncology departments and rehabilitation centers where there is need for better control of pain that minimizes or eliminates the use of analgesics and other pain killing drugs.

In this instance it is possible to combine the use of SBOTs represented as "sound massage" combined with light emission effects. The basic strokes using sonoluminescent biophysical oscillations massage for labor pain management consists of effleurages (a form of massage involving a circular stroking movement made with the palm of the hand) that are provided using sequential long and short gliding and lifting strokes during the alternating intermittent repetitions applied to the human body. These massage strokes applied during active SBOT sessions and the accompanying methodology using a similar program as described above that includes selection of music and image/light/colors for the 5 phases in order to lead to an increase in activation of receptors that enhance efficiency of masking sounds produced in response to the participant/parturient being able to withstand a higher threshold tracson associated with resonance perception. The effective response that is provided and amplified by touch is coordinated with the SBOT and the entire set of sessions can be performed in the audiovisual environment/room as available.

The mechanism of pain management occurs due to the temporal integration of simultaneous mechanical stimulation of the skin which has a basis that is similar to the stimulation provided by sound in hearing. The actual mechanism that alleviates pain is different for different types of receptors including Pacinian corpuscle receptors that are provided and activated such that temporal integration occurs within 100 ms (100 milliseconds). Additional skin receptors act as thermo-receptors which are basically adaptation receptors. These receptor cells mediate the sensation of pain regarding response to chemicals, heat, and cold.

As the massage strokes are provided along with the use of SBOTs there is also an increase in TRPV1 channel activation cycles/vasopressin water channel cycles that occur due to intermittent alternating repetitions. This also includes other channel cycles that affect the brain tissues. In addition the stimulation of the skin's thermo-receptors causes physiological changes induced via sound/colors and light massage on the participant's body. These changes involve activation of GABA/glycine inhibitors/cold receptors/warm receptors that all lead to the release of Glutamate.

It is useful to note that Glutamate is the most abundant excitatory neurotransmitter in the central nervous system (CNS) and provides for a deeper and faster induction of a state of relaxation for the recipient. Concurrently there are also induced changes in activation of NMDA (NMDA receptor is a glutamate and ion channel protein receptor that is activated when glycine and glutamate bind to it) leading to an increase of the newly generated vasopressin water channel cycles on the brain tissue. This response is due to the parturient's perception of the tracson resonance/chromatophore emissions. These emissions provide responses of a sedative/energetic nature while the participant is exposed to the audiovisual environment. This activity also leads to an increase in the inducement of endogenous opiates in the brain that act like a morphine pump. These changes are primarily based on interactions associated with endogenous cannabinoid system-cannabinoid receptors along with heat shock proteins and molecular chaperones. These connected mechanisms all provide for the ultimate objective—better control of pain during labor.

More specifically, to accomplish the pain management techniques described above, the massage strokes are applied with an open hand with at first, short lifting gliding strokes that are applied very gently to the back of the neck (known as the nape region). This region is strongly linked to the induction of tracson accumulation sites in the occipital cerebral cortex as well as to the forehead region. The forehead region is also linked to induced tracson accumulation sites that energize the frontal cerebral cortex. Next, long gliding lifting strokes are applied by intermittent alternating repetitions on right side/left side of the parturient's body. More specifically, first on the upper limbs and then the lower limbs. If possible, simultaneously the right side/left side of the upper limbs and then the lower limbs are massaged in a descending manner from the shoulder areas to the wrist on right side of the upper limb. This is followed by short gliding lifting strokes on the hands starting from the extremities of fingers toward the wrist onward toward the upper posterior portion of the hand. Next, short gliding lifting strokes are provided to the anterior portion of the palm of the hand accompanied by a slight squeeze of the fingers. This provides a very relaxing stretch in the fingers and in a similar way the entire process is applied to the left side of the upper limbs.

In addition, gliding lifting strokes are applied in a descending approach on the lower limbs starting from the hip and heading to the ankle on right side of the lower limbs. This is followed by descending short gliding and lifting strokes applied to the ankle that are then headed toward the toes on the posterior surface of the feet. The manual massage then follows along the anterior surface of the feet (sole of the foot) from the heel toward the toes accompanied by a slight squeeze of the toes. This procedure provides a very relaxing stretch in the toes. The same procedure is followed for stroking the left side of lower limbs. In some cases, it is possible and desirable to simultaneously provide this process on both sides on upper limbs first and then the lower limbs. This massage technique is especially useful and provides the greatest response during phase transitions 3-4 and 4-5 of the SBOTs (described in detail above).

In yet another embodiment of the same SBOT/manual massage applications, the massage portion begins with short gliding strokes on the forehead followed by the base of the neck during alternating intermittent repetitions of the SBOTs that act on the dominant parturient's brain rhythm in the occipital cerebral cortex. This process can also be reversed. It is also possible to apply long/short gliding strokes on the surface of the upper chest with very light pressure. This is followed by using the identical pattern to the abdomen, and then ascendant long gliding strokes are applied from the lower back region toward the upper back across the back muscles—also with very light pressure. Following the same ascending manner with short gliding strokes using more firm pressure than before and in a circular motion along the spinal cord together with the SBOTs provides the parturient a very relaxing sensation along the central canal in the spinal cord. This technique provides a response that is actuated by sound molecular bubbles (described above) that resonate as a result of the addition of the massage. This SBOT/massage combination releases tensions accumulated in each of the motor nerve roots that are associated with the paravertebral sympathetic ganglia relays and their meeting (or intersection) points where the 5 tracsons accumulation sites induce action by cortical tracson accumulation sites in the occipital cerebral cortex. Strokes are applied by intermittent alternating repetitions cycles on the parturient's human body structures during the 5 phases of the SBOT application utilizing the basic protocol of music-light/colors selection with slight changes in the choice of the original music composition. In so doing, this technique causes responses that emphasize the sense of touch by increasing the TRPV1 channel activation cycles/vasopressin water channel cycles acting on the parturient's brain tissues. Using the by intermittent alternating repetitions leads to sedative/energetic tracson—chromatophores effects on the parturient as required and induces an increase in the occipital-temporal-parietal cycles as the participant experiences a transition toward the parietal-frontal portion leading to faster induction of dominant brain rhythms in the frontal cerebral cortex at phase transitions 3-4/4-5. The resulting response is a faster (less time required) induction of deep states of relaxation for the parturient.

It should be noted that the massage strokes follow the pathways of SBOT which correspond to a response of the parturient's brain rhythm during deeper and faster levels of induced relaxation states akin to faster activation and generation of endogenous opiates as if a morphine pump was being employed.

In yet a further embodiment, the massage strokes are applied with an open hand using light/firm pressure with the light pressure similar to that used to apply a lotion or a cream on the face. The firm pressure used should be firm pressure applied by the entire hand and/or foot across muscles of the back to release the tensions of the overall body. These techniques along with the SBOT facilitate an increase in the occipital-temporal-parietal cycles that transition toward parietal-frontal portions allowing for faster induction of dominant brain rhythms in the frontal cerebral cortex at phase transitions 3-4/4-5. The result is that faster induction of deep states of relaxation for the parturient occurs by both further activation of the SBOTs as well as providing more of sound resonance activation that spreads to the extremities of the body by intermittent alternating repetitions including light emission. This provides the dominant parturient's brain rhythm response in the occipital cortex and induces change in the up-regulation of dominant brain rhythm in a specific cortical site. This allows for activation of the extremities of the feet through the toes and a higher threshold of activation of the thermo-receptors heavily concentrated on the soles of the feet.

By using massage on the feet followed by induced changes in the up-regulation of the dominant parturient's brain rhythm from the occipital cerebral cortex toward the frontal cerebral cortex (a reverse process is also possible) the extremities of the hands through the fingers are also affected. The response is felt by reaching a higher threshold that activates cold receptors in the joints of the fingers in association as well as activating cold receptors found in the aponeurosis of terminal motor roots along the spinal cord.

There are also some other organs affected by massage on the back utilizing very gentle circular motions with ascending strokes along the spinal cord from the lower back toward the upper back so on the parturient's body responds to sequential intermittent repetitive cycles during the 5 sequential phases of active SBOT. This all leads to the activation of glycine receptors on the forebrain and the release of Glutamate as well as generation of dominant parturient's brain rhythm cycles in the frontal cerebral cortex. There is therefore an increase of the dominant parturient's vasopressin channel cycles on the brain tissues as a result of an increase of the induction of endogenous opiates. This includes a response to an increase of TRPV1 channels cycles and activation of thermo-receptors in skin by the use of massage with some other channel cycles on the brain tissues accompanied by an enhanced induction of micro sound molecular bubbles that increase in concentration during flow on the argon matrix and sequentially on specific CSF filled cavities which are comprised of 99% water. As previously described, the CSF includes in a sequential order the central canal in the spinal cord, then the IV ventricle, then the III ventricles and then two lateral ventricles in the brain. All of these are affected during the 5 sequential phase applications of the SBOTs.

There is also TRPV1 activation for stressed and non-stressed cells that depends on the respective pH medium in which the cells reside. The cells may exude acid producing induced changes in the thermoregulation of the cells. In addition, activation of lipid-based ligands occurs which may linked to endogenous activators of TRPV1. This phenomenon is due to various fatty acid derivatives that activate TRPV1 endogenously produced in the central nervous system (CNS). Activation of TRPV1 using tones or sound is especially important for pain reduction during SBOTs. This is because sound alternating rotations induce sound analgesia. The use of the combination of SBOT/massage on the human body for better control of labor pain for the parturient provide an enhanced management of pain generated by many additional causes including post trauma, accidents, or from pain and aches in the body induced by stressful situations in cells that exhibit a stressed behavior. In addition weakened tissues are vulnerable because of a weakened immune system that is present due to exposure to and residence in medical facilities including birthing centers, rehabilitation facilities, hospitals, and clinics, where there is need for better management of pain as opposed to the use of pain killing drugs that can further depress the immune system and/or immune response. This working example indicates how the eventual minimum use of pain killers such as opioids can be avoided.

Signals that are endogenously produced also appear to be activated by tone/sound/sound resonance along the CNS TRPV1. This alters basal neurotransmission because TRPV1 resides in the hippocampus and involves activation of TRPV1-mediated interneurons LTD (Long term depression) activity. There is also a response to mGLUR1 activation follow by 12-HPETE formation which represents endogenously produced TRPV1 CNS ligands. These can include, for instance, C18 N-acylethanolamines, endovanilloid N-oleoylethanolamine, N-arachydonoyl, and anandamide (AEA)—all produced in the hippocampus by stimulation using the tracsons/chromatophore effects described in the protocols listed above. These techniques are used to induce changes in synaptic plasticity of the participant during exposure to SBOT.

There is also actually an increase in glutamate neurotransmission in response to mGLUR1 antagonists where TRPV1 antagonists alter increased activity in the rostral ventromedial medulla, suggesting that the interneurons are inhibited by TRPV1 via mGLUR1 during the process of applying sound or tones.

In other brain regions TRPV1 activated with tones such as in the substantia nigra in response to tonic anandamide release at activation of vasopressin water channel cycles accompanied by dominant activation of glycine receptors on the forebrain and glutamate release occurs during SBOTs. This includes proton channel cycle(s) activation and more induced changes in the activation of predominantly substantia nigra reticulata and the subsequent associated changes in substantia nigra pars compacta in substantia nigra. Here the TRPV1 channel cycles are activated by induced changes in the signals produced by endogenously lipid ligand in the central nervous system that is associated with the pH medium of the either stressed or non-stressed cells. This, as before, also involves thermoregulation of the participant's brain tissues in order that the participant's brain rhythm can change and respond accordingly. These brain rhythm changes help the recipient capture low frequency sounds as well as specific colored wavelengths induced by SBOTs As activation occurs, capture and release of gravitational sonoluminescent biophysical oscillations wavelengths form in the space-time continuum with a duality particles including the tracsons/chromatophores that pulse at the speed of light and which cause changes in the dominant brain rhythm associated with the occipital cerebral cortex of the participant.

Along with the ability to alleviate pain the use of SBOTs, the working example techniques described herein have also been found to induce changes in the activation of Kappa-opioid receptors in the nucleus accumbens in response to TRPV1 activation that inhibits glutamate and GABA release. This process utilizes different mechanisms linked to the intestinal cholesterol metabolism. Activation of the Kappa-opioid receptor inhibits fat intake inhibition that interacts with opioid (in response to activation of vasopressin water channel activation and anandamide release). This process helps modify stress related behavior during transition of the subjective feelings experienced by the participant in a present mode as they transition to the final mode. This is due to the eventual induction of γ-endorphins and their beneficial effects on the improvement of participant's social behavior. In addition, endogenous peptide opiates such as endorphins and beta-endorphins for modulation of pain are produced in certain neurons within the central nervous system and peripheral nervous system, which bind to opioid receptors. The overall response includes analgesia and sedation with a morphine pump-like effect that here additionally includes induction of some other endogenous peptides such as enkephalins involved in regulating nociception in the body. These responses include endogenous dynorphin signaling via the Kappa-opioid receptor (KOR) in the nucleus accumbens (NACC) at TRPV1 activation and fat intake inhibition.

It is to be understood that the is particular invention is not limited to the exact construction illustrated and described above, but that various changes and modifications may be made without departing from the spirit and scope of the invention as defined in the following claims.

What is claimed is:

1. One or more devices which together provide sonoluminescence biophysical oscillation technique(s) (SBOT(s)) to alleviate individualized debilitating symptoms exhibited by one or more humans comprising: at least one room that contains one or more sound emitting devices that include speakers that provide biophysical oscillations that initiate, sustain, and/or control transmission of harmonic and subharmonic sound(s) including music and/or individual musical notes that provide alternated pulsing sound wavelength frequencies and also one or more light emission devices including projectors that provide alternating pulsing light wave emission frequencies that impart changes in color and/or colored wavelengths of light, wherein said alternating pulsing sound wavelength frequencies and said alternating pulsing light wave emission frequencies supply auditory and visual stimuli that cause specific energy changes, wherein said specific energy changes create chromophore excitations, wherein said chromophore excitations are configured to be applied to one or more external portions of one or more human bodies.

2. The one or more devices of claim 1, wherein said SBOT(s) results in a change of regulation of Human Growth Hormone Factors (HGHF) to one or more individuals subjected to said provision of SBOT(s) and designated as participants.

3. The one or more devices of claim 1, wherein said provision of SBOT(s) results in a change of regulation of Human Growth Hormone (HGH) to one or more groups of participants.

4. The one or more devices of claim 1, wherein via an addition of sound and light and color changes leading to said chromophore excitations the one or more devices also allow creative participants an ability to provide or have provided for them individualized activities that are utilized to further improve human health conditions, said health conditions selected from one or more of a group consisting of: improvements in a vasopricin center for anxiety, pain, and analgesic issues, an oxytocin center, DNA and CNS (central nervous system) repair, and retinol/neuromelanine regeneration.

5. The one or more devices of claim 1, wherein said provision of SBOT(s) is delivered together with devices that emit sound and light and are activated, utilized, and controlled by one or more computer devices, wherein said computer devices are selected from one or more of a group consisting of: cellular phones, smart phones, laptops, networked computers, computer pads, televisions, radios, and transceivers, wherein said transceivers are transmitters and/or receivers and either transmit or receive or transmit and receive energy within a confined indoor space that includes an indoor space designated to be an audiovisual room.

6. The one or more devices of claim 5, wherein said energy is sent or received as a form of energy selected from at least one of a group of forms of energy consisting of: optical, electrical, mechanical, radiative, solar, and wind energy.

7. The one or more devices of claim 6, wherein said form of energy is sent directly, as an energy signal or an energy wave that is configured to be transmitted to and received by a human body.

8. The one or more devices of claim 1, wherein said one or more devices deliver SBOT(s) applied to improve one or more components associated with a human body selected from one or more of a group consisting of: human bones/skeletal structure, human tissues, human nerves, and human organs including human skin.

9. The one or more devices of claim 1, wherein said one or more devices deliver creative activities wherein said activities include making and/or listening to music for one or more individuals receiving SBOT(s) via a person, equipment and/or by utilizing a virtual equivalent thereof and wherein said individuals are further able to apply manual dexterity with an ability to listen to music, draw, and write.

10. The one or more devices of claim 1, wherein said one or more devices provide delivery of at least one or more creative activities to one or more individuals, wherein said creative activities include a patient's use together with administering SBOT(s).

11. The one or more devices of claim 1, wherein said one or more devices provide delivery of at least one or more creative activities to one or more individuals, wherein said creative activities are selected from at least one of a group consisting of: creative painting and drawing.

12. The one or more devices of claim 1, wherein said one or more devices are capable of delivering at least one or more creative activities delivered to one or more participants, wherein said creative activities include creation of one or more images by one or more of said one or more devices and/or computers/cameras such that said creative activities are received and created by one or more participants to which SBOT(s) is administered.

13. The one or more devices of claim 1, wherein said SBOT(s) induces deep relaxation states in one or more participants by implementation of rotation and/or intermittent application(s) in a series of SBOT(s) to provide a positive response to said participants.

14. The one or more devices of claim 13, wherein said deep relaxation states are a result of directed and focused SBOT(s) to a frontal cortex of a human brain and reversal of SBOT(s) by intermittent applications over time to accomplish a positive response and outcome in a participant.

15. A system that provides sonoluminescence biophysical oscillation technique(s) (SBOT(s)) to alleviate debilitating human conditions of individuals comprising: at least one room that contains one or more sound emitting devices that includes at least one speaker that provides biophysical oscillations that initiate, sustain, and/or control transmission of harmonic and subharmonic sound(s) including music and/or individual musical notes that provide alternated pulsing sound wavelength frequencies and also one or more light emission devices including projectors that provide alternating pulsing light wave emission frequencies that impart changes in color and/or colored wavelengths of light wherein said alternating pulsing sound wavelength frequencies and said alternating pulsing light wave emission frequencies supply auditory and visual stimuli that cause specific energy changes, wherein said chromophore excitations are configured to be applied to one or more external portions of one or more human bodies.

16. The system of claim 15, wherein said SBOT(s) results in a change of regulation of Human Growth Hormone Factors (HGHF).

17. The system of claim 15, wherein said provision of SBOT(s) results in a change of regulation of Human Growth Hormone (HGH) to one or more groups of participants.

18. The system of claim 15, wherein said SBOT(s) is delivered together with devices that emit sound and light and are activated, utilized, and controlled by one or more computer devices, wherein said computer devices are selected from one or more of a group consisting of cellular phones, smart phones, laptops, networked computers, computer pads, televisions, radios, and transceivers, wherein said transceivers are transmitters and/or receivers and either transmit or receive or transmit and receive energy.

19. The system of claim 18, wherein said energy is sent or received as a form of energy selected from at least one or more of a group of forms of energy consisting of optical, electrical, mechanical, radiative, solar, and wind energy.

20. The system of claim 19, wherein said form of energy is sent directly, as a signal or a wave or in a form of energy that can be transmitted and received by a human body.

21. The system of claim 15, wherein said system delivers SBOT(s) that is applied to improve one or more components associated with a human body selected from one or more of a group consisting of human bones/skeletal structure, human tissues, human nerves, and human organs including human skin.

22. The system of claim 15, wherein said system delivers creative activities wherein said activities include making and/or listening to music to one or more individuals with or without a person administering SBOT(s) and wherein said creative activities include making and/or listening to music that includes providing an individual with an improved ability to listen to music, draw, and write.

23. The system of claim 15, wherein said system provides delivery of at least one or more creative activities to one or more individuals, wherein said creative activities include a patient's use together with administering SBOT(s).

24. The system of claim 15, wherein said system provides delivery of at least one or more creative activities to one or more individuals, wherein said creative activities are selected from at least one of a group consisting of: creative painting and drawing.

25. The system of claim 15, wherein said system includes at least one or more creative activities delivered to one or more individuals, wherein said creative activities include creation of one or more images by one or more of said devices and/or computers/cameras that are received by one or more individuals to which SBOT(s) is administered.

26. The system of claim 15, wherein provision of said SBOT(s) induces deep relaxation states in one or more individuals by implementation of rotation and/or intermittent application(s) of said SBOT(s) and wherein said deep relaxation states are a result of directed and focused SBOT(s) treatment to a frontal cortex of a human brain that causes reversal by intermittent applications.

* * * * *